(12) United States Patent
Prockop et al.

(10) Patent No.: US 10,035,834 B2
(45) Date of Patent: Jul. 31, 2018

(54) MESENCHYMAL STEM CELLS, COMPOSITIONS, AND METHODS FOR TREATMENT OF CARDIAC TISSUE DAMAGE

(75) Inventors: Darwin J. Prockop, Philadelphia, PA (US); RyangHwa Lee, Round, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 12/487,373

(22) Filed: Jun. 18, 2009

(65) Prior Publication Data
US 2010/0278790 A1  Nov. 4, 2010

(51) Int. Cl.
| | | |
|---|---|---|
| A61K 38/17 | (2006.01) |
| C07K 14/435 | (2006.01) |
| C07K 14/525 | (2006.01) |
| C12N 5/0775 | (2010.01) |

(52) U.S. Cl.
CPC .......... C07K 14/525 (2013.01); C12N 5/0663 (2013.01); *C12N 2501/25* (2013.01); *C12N 2501/585* (2013.01)

(58) Field of Classification Search
CPC ............................... A61K 38/17; C07K 14/435
See application file for complete search history.

(56) References Cited

U.S. PATENT DOCUMENTS

| | | | |
|---|---|---|---|
| 5,386,013 A | 1/1995 | Lee et al. | |
| 6,313,091 B1 | 11/2001 | Wisniewski et al. | |
| 6,387,369 B1 | 5/2002 | Pittenger et al. | |
| 6,872,546 B1* | 3/2005 | Hastings et al. ............. 435/69.1 | |
| 2002/0045589 A1* | 4/2002 | Shen .................... C07K 14/811 514/44 R |
| 2004/0115199 A1 | 6/2004 | Halkier et al. | |
| 2007/0128719 A1 | 6/2007 | Tseng et al. | |
| 2007/0213255 A1 | 9/2007 | Hastings et al. | |

OTHER PUBLICATIONS

Chen et al, Nature Medicine 13(7):851-856, 2007; available online Jun. 17, 2007.*
WebMD, http://www.webmd.com/heart-disease/what-is-atherosclerosis; last accessed Apr. 19, 2012.*
Jacobs, Drug Discovery Today 12(23/24): 1040-1045, 2007.*
Wisniewski et al, J. Immunol. 156:1609-1615, 1996.*
Patti et al, Clinical Therapeutics 27(9): 1411-1419, 2005.*
Alisky, Medical Hypotheses 67:53-56, 2006.*
The Jackson Laboratory, Body Weight Information; http://jaxmice.jax.org/support/weight/000651.html; last visited Dec. 18, 2014.*
Giugliano et al, Am. J. Cardiology 91:1055-1059, 2003.*
Wu et al, J. Biomed Lab. Sci. 19(1):1-6, 2007.*
Simpson et al, J. Clin. Invest. 81:624-629, 1988.*
Getting et al, J. Biol. Chem. 52(27):51068-51076, 2002.*
Sugano et al, FASEB 18(7):911-913, 2004.*
Calvillo et al, Proc. Nat'l Acad. Sci. 100(8):4802-4806, 2003.*
Barbash, et al., "Systemic delivery of bone marrow-derived mesenchymal stem cells to the infarcted myocardium: feasibility, cell migration, and body distribution." 2003, Circulation 108:863-8.
Bardos et al., "Anti-inflammatory and chondroprotective effect of TSG-6 (tumor necrosis factor-alpha-stimulated gene-6) in murine models of experimental arthritis." 2001, Am J Pathol 159:1711-21.
Burt, et al., "Clinical applications of blood-derived and marrow-derived stem cells for nonmalignant diseases." 2008, JAMA 299(8):925-36.
Carvalho et al., "Heart failure alters matrix metalloproteinase gene expression and activity in rat skeletal muscle." 2006, Int J Exp Pathol 87:437-443.
Charwat, et al., "Role of adult bone marrow stem cells in the repair of ischemic myocardium: current state of the art." 2008, Exp Hematol 36(6):672-80.
Dimmeler, et al., "Aging and disease as modifiers of efficacy of cell therapy." 2008, Circ Res 102(11):1319-30.
Fang et al., "Differences in inflammation, MMP activation and collagen damage account for gender difference in murine cardiac rupture following myocardial infarction." 2007, J Mol Cell Cardiol 43:535-544.
Forteza et al., "TSG-6 potentiates the antitissue kallikrein activity of inter-alpha-inhibitor through bikunin release." 2007 Am J Respir Cell Mol Biol 36(1):20-31.
Gao et al., "The dynamic in vivo distribution of bone marrow-derived mesenchymal stem cells after infusion." 2001, Cells Tissues Organs. 169(1):12-20.
Getting et al., "The link module from human TSG-6 inhibits neutrophil migration in a hyaluronan- and inter-alpha-inhibitor-independent manner." 2002 J Biol Chem 277(52):51068-76.
Halkos et al., "Intravenous infusion of mesenchymal stem cells enhances regional perfusion and improves ventricular function in a porcine model of myocardial infarction." 2008, Basic Res Cardiol 103(6):525-36.
Heng et al., "Hyaluronan binding to link module of TSG-6 and to G1 domain of aggrecan is differently regulated by pH." 2008, J Biol Chem 283(47):32294-301.
Iso et al., "Multipotent human stromal cells improve cardiac function after myocardial infarction in mice without long-term engraftment." 2007, Biochem Biophys Res Commun 354:700-706.
Krause et al., "Intravenous delivery of autologous mesenchymal stem cells limits infarct size and improves left ventricular function in the infarcted porcine heart." 2007 Stem Cells Dev 16:31-37.
Lee et al., "A novel secretory tumor necrosis factor-inducible protein (TSG-6) is a member of the family of hyaluronate binding proteins, closely related to the adhesion receptor CD44." 1992, J Cell Biol 116:545-557.

(Continued)

*Primary Examiner* — Kevin K Hill
(74) *Attorney, Agent, or Firm* — Raymond J. Lillie

(57) ABSTRACT

The present invention provides compositions comprising mesenchymal stem cells (MSCs), and methods for their novel use in the repair of cardiac damage and treatment of inflammatory diseases. The invention also provides methods for using TSG-6 protein that is secreted by MSCs under certain conditions, for repair of cardiac damage and inflammatory disease. The compositions of the invention may be particularly useful in restoring cardiac function following cardiac damage, including, but not limited to, myocardial infarction, as well as in reducing symptoms of inflammatory disease.

3 Claims, 28 Drawing Sheets

(56) References Cited

OTHER PUBLICATIONS

Milner et al., "TSG-6: a pluripotent inflammatory mediator?" 2006, Biochem Soc Trans 34(pt 3):446-50.
Mindrescu et al., "Amelioration of collagen-induced arthritis in DBA/1J mice by recombinant TSG-6, a tumor necrosis factor/interleukin-1-inducible protein." 2000, Arthritis Rheum 43:2668-2677.
Mindrescu et al., "Reduced susceptibility to collagen-induced arthritis in DBA/1J mice expressing the TSG-6 transgene." 2002, Arthritis Rheum 46:2453-2464.
Moshal et al., "Targeted deletion of MMP-9 attenuates myocardial contractile dysfunction in heart failure." 2008, Physiol Res 57:379-384.
Ovechkin et al., "Role of matrix metalloproteinase-9 in endothelial apoptosis in chronic heart failure in mice." 2005, J Appl Physiol 99:2398-2405.
Paolocci et al., "Metalloproteinase inhibitor counters high-energy phosphate depletion and AMP deaminase activity enhancing ventricular diastolic compliance in subacute heart failure." 2006, J Pharmacol Exp Ther 317:506-513.
Schrepfer et al., "Stem cell transplantation: the lung barrier." 2007, Transplant Proc 39:573-6.
Segers et al., "Stem-cell therapy for cardiac disease." 2008, Nature 451(7181):937-42.
Szanto et al., "Enhanced neutrophil extravasation and rapid progression of proteoglycan-induced arthritis in TSG-6-knockout mice." 2004, Arthritis Rheum 50:3012-3022.
Wisniewski et al., "Cytokine-induced gene expression at the crossroads of innate immunity, inflammation and fertility: TSG-6 and PTX3/TSG-14." 2004, Cytokine Growth Factor Rev 15(2-3):129-46.
Wolf et al., "Stem cell therapy improves myocardial perfusion and cardiac synchronicity: new application for echocardiography." 2007, J Am Soc Echocardiogr 20:512-520.

\* cited by examiner

MI

MI + hMSCs

MI + scr siRNA

MI + TSG-6 siRNA

MI + rh TSG-6

MIILIYLYLFLLLWEDTQGWGFKDGIFHNSIWLERAAGVYHREARS

GKYKLTYAEAKAVCEFEGGHLATYKQLEAARKIGFHVCAAGWMAKGRVGYPIVKPGPN

CGFGKTGIIDYGIRLNRSERWDAYCYNPHAKECGGVFTDPKQIFKSPGFPNEYEDNQI

CYWHIRLKYGQRIHLSFLDFDLEDDPGCLADYVEIYDSYDDVHGFVGRYCGDELPDDI

ISTGNVMTLKFLSDASVTAGGFQIKYVAMDPVSKSSQGKNTSTTSTGNKNFLAGRFSHL

FIG. 19A

```
   1 cagtcacatt tcagccactg ctctgagaat tgtgagcag ccctaacag gctgttactt
  61 cactacaact gacgatatga tcatcttaat ttacttattt ctcttgctat gggaagacac
 121 tcaaggatgg ggattcaagg atggaatttt tcataactcc atatggcttg aacgagcagc
 181 cggtgtgtac cacagagaag cacggtctgg caaatacaag ctcacctacg cagaagctaa
 241 ggcggtgtgt gaatttgaag gcggccatct cgcaacttac aagcagctag aggcagccag
 301 aaaaattgga tttcatgtct gtgctgctgg atggatggct aagggcagag ttggataccc
 361 cattgtgaag ccagggccca actgtggatt tggaaaaact ggcattattg attatggaat
 421 ccgtctcaat aggagtgaaa gatgggatgc ctattgctac aacccacacg caaaggagtg
 481 tggtggcgtc tttacagatc caaagcaaat ttttaaatct ccaggcttcc caaatgagta
 541 cgaagataac caaatctgct actggcacat tagactcaag tatggtcagc gtattcacct
 601 gagttttttta gattttgacc ttgaagatga cccaggttgc ttggctgatt atgttgaaat
 661 atatgacagt tacgatgatg tccatggctt tgtgggaaga tactgtggag atgagcttcc
 721 agatgacatc atcagtacag gaaatgtcat gaccttgaag tttctaagtg atgcttcagt
 781 gacagctgga ggtttccaaa tcaaatatgt tgcaatggat cctgtatcca aatccagtca
 841 aggaaaaaat acaagtacta cttctactgg aaataaaaac ttttagctg gaagatttag
 901 ccacttataa aaaaaaaaa aaggatgatc aaaacacaca gtgtttatgt tggaatcttt
 961 tggaactcct tgatctcac tgttattatt aacatttatt tattatttt ctaaatgtga
1021 aagcaataca taatttaggg aaaattggaa aatataggaa actttaaacg agaaaatgaa
1081 acctctcata atcccactgc atagaaataa caagcgttaa cattttcata ttttttttctt
1141 tcagtcattt ttctatttgt ggtatatgta tatatgtacc tatatgtatt tgcatttgaa
1201 attttggaat cctgctctat gtacagtttt gtattatact ttttaaatct tgaactttat
1261 aaacattttc tgaaatcatt gattattcta caaaaacatg attttaaaca gctgtaaaat
1321 attctatgat atgaatgttt tatgcattat ttaagcctgt ctctattgtt ggaatttcag
1381 gtcattttca taaatattgt tgcaataaat atccttgaac acaaaaaaaa aaaaaaaaa
```

FIG. 19B

SEQUENCE LISTING

<160> NUMBER OF SEQ ID NOS: 20

<210> SEQ ID NO 1
<211> LENGTH: 21
<212> TYPE: DNA
<213> ORGANISM: Artificial
<220> FEATURE:
<223> OTHER INFORMATION: Alu Forward Primer

<400> SEQUENCE: 1

-continued catggtgaaa ccccgtctct a                                    21

<210> SEQ ID NO 2
<211> LENGTH: 19
<212> TYPE: DNA
<213> ORGANISM: Artificial
<220> FEATURE:
<223> OTHER INFORMATION: Alu Reverse Primer

<400> SEQUENCE: 2
gcctcagcct cccgagtag                                       19

<210> SEQ ID NO 3
<211> LENGTH: 20
<212> TYPE: DNA
<213> ORGANISM: Artificial
<220> FEATURE:
<223> OTHER INFORMATION: Alu Probe

<400> SEQUENCE: 3
attagccggg cgtggtggcg                                      20

<210> SEQ ID NO 4
<211> LENGTH: 24
<212> TYPE: DNA
<213> ORGANISM: Artificial
<220> FEATURE:
<223> OTHER INFORMATION: h/mGAPDH Forward Primer

<400> SEQUENCE: 4
cagcgacacc cactcctcca cctt                                 24

<210> SEQ ID NO 5
<211> LENGTH: 24
<212> TYPE: DNA
<213> ORGANISM: Artificial
<220> FEATURE:
<223> OTHER INFORMATION: h/mGAPDH Reverse Primer

<400> SEQUENCE: 5
catgaggtcc accaccctgt tgct                                 24

<210> SEQ ID NO 6
<211> LENGTH: 24
<212> TYPE: DNA
<213> ORGANISM: Artificial
<220> FEATURE:
<223> OTHER INFORMATION: TSG-6 Forward Primer

<400> SEQUENCE: 6
aagcacggtc tggcaaatac aagc                                 24

<210> SEQ ID NO 7
<211> LENGTH: 24
<212> TYPE: DNA
<213> ORGANISM: Artificial
<220> FEATURE:
<223> OTHER INFORMATION: TSG-6 Reverse Primer

<400> SEQUENCE: 7
atccatccag cagcacagac atga                                 24

<210> SEQ ID NO 8
<211> LENGTH: 25
<212> TYPE: DNA

```
<213> ORGANISM: Artificial
<220> FEATURE:
<223> OTHER INFORMATION: TSG-6 Probe

<400> SEQUENCE: 8
tttgaaggcg gccatctcgc aactt                                              25

<210> SEQ ID NO 9
<211> LENGTH: 24
<212> TYPE: DNA
<213> ORGANISM: Artificial
<220> FEATURE:
<223> OTHER INFORMATION: DIDO1 Forward Primer

<400> SEQUENCE: 9
atggtttcat ggcgattgtg tggg                                               24

<210> SEQ ID NO 10
<211> LENGTH: 24
<212> TYPE: DNA
<213> ORGANISM: Artificial
<220> FEATURE:
<223> OTHER INFORMATION: DIDO1 Reverse Primer

<400> SEQUENCE: 10
acttgcagaa tggtgcagtt tggg                                               24

<210> SEQ ID NO 11
<211> LENGTH: 24
<212> TYPE: DNA
<213> ORGANISM: Artificial
<220> FEATURE:
<223> OTHER INFORMATION: BMPR2 Forward Primer

<400> SEQUENCE: 11
acagaggttg gaaaccatcc cact                                               24

<210> SEQ ID NO 12
<211> LENGTH: 24
<212> TYPE: DNA
<213> ORGANISM: Artificial
<220> FEATURE:
<223> OTHER INFORMATION: BMPR2 Reverse Primer

<400> SEQUENCE: 12
agtgacctca ctgccaggct attt                                               24

<210> SEQ ID NO 13
<211> LENGTH: 24
<212> TYPE: DNA
<213> ORGANISM: Artificial
<220> FEATURE:
<223> OTHER INFORMATION: SMAD6 Forward Primer

<400> SEQUENCE: 13
acaagccact ggatctgtcc gatt                                               24

<210> SEQ ID NO 14
<211> LENGTH: 24
<212> TYPE: DNA
<213> ORGANISM: Artificial
<220> FEATURE:
<223> OTHER INFORMATION: SMAD6 Reverse Primer

<400> SEQUENCE: 14
agaattcacc cggagcagtg atga                                               24
```

<210> SEQ ID NO 15
<211> LENGTH: 24
<212> TYPE: DNA
<213> ORGANISM: Artificial
<220> FEATURE:
<223> OTHER INFORMATION: CSF1 Forward Primer

<400> SEQUENCE: 15
tcagatggag acctcgtgcc aaat                                            24

<210> SEQ ID NO 16
<211> LENGTH: 24
<212> TYPE: DNA
<213> ORGANISM: Artificial
<220> FEATURE:
<223> OTHER INFORMATION: CSF1 Reverse Primer

<400> SEQUENCE: 16
tatctctgaa gcgcatggtg tcct                                            24

<210> SEQ ID NO 17
<211> LENGTH: 24
<212> TYPE: DNA
<213> ORGANISM: Artificial
<220> FEATURE:
<223> OTHER INFORMATION: VCAM1 Forward Primer

<400> SEQUENCE: 17
ttgctcagat tggtgactcc gtct                                            24

<210> SEQ ID NO 18
<211> LENGTH: 24
<212> TYPE: DNA
<213> ORGANISM: Artificial
<220> FEATURE:
<223> OTHER INFORMATION: VCAM1 Reverse Primer

<400> SEQUENCE: 18
ttcgtcacct tcccattcag tgga                                            24

<210> SEQ ID NO 19
<211> LENGTH: 277
<212> TYPE: PRT
<213> ORGANISM: Homo sapiens

<400> SEQUENCE: 19

Met Ile Ile Leu Ile Tyr Leu Phe Leu Leu Leu Trp Glu Asp Thr Gln
1               5                   10                  15

Gly Trp Gly Phe Lys Asp Gly Ile Phe His Asn Ser Ile Trp Leu Glu
            20                  25                  30

Arg Ala Ala Gly Val Tyr His Arg Glu Ala Arg Ser Gly Lys Tyr Lys
        35                  40                  45

Leu Thr Tyr Ala Glu Ala Lys Ala Val Cys Glu Phe Glu Gly Gly His
    50                  55                  60

Leu Ala Thr Tyr Lys Gln Leu Glu Ala Ala Arg Lys Ile Gly Phe His
65                  70                  75                  80

Val Cys Ala Ala Gly Trp Met Ala Lys Gly Arg Val Gly Tyr Pro Ile
                85                  90                  95

Val Lys Pro Gly Pro Asn Cys Gly Phe Gly Lys Thr Gly Ile Ile Asp
            100                 105                 110

Tyr Gly Ile Arg Leu Asn Arg Ser Glu Arg Trp Asp Ala Tyr Cys Tyr

|  |  |  | 115 |  |  |  | 120 |  |  |  | 125 |  |
|---|---|---|---|---|---|---|---|---|---|---|---|---|
| Asn | Pro | His | Ala | Lys | Glu | Cys | Gly | Gly | Val | Phe | Thr | Asp | Pro | Lys | Gln |
|  |  |  | 130 |  |  |  | 135 |  |  |  | 140 |  |

Ile Phe Lys Ser Pro Gly Phe Pro Asn Glu Tyr Glu Asp Asn Gln Ile
145                 150                 155                 160

Cys Tyr Trp His Ile Arg Leu Lys Tyr Gly Gln Arg Ile His Leu Ser
                165                 170                 175

Phe Leu Asp Phe Asp Leu Glu Asp Asp Pro Gly Cys Leu Ala Asp Tyr
            180                 185                 190

Val Glu Ile Tyr Asp Ser Tyr Asp Asp Val His Gly Phe Val Gly Arg
        195                 200                 205

Tyr Cys Gly Asp Glu Leu Pro Asp Asp Ile Ile Ser Thr Gly Asn Val
    210                 215                 220

Met Thr Leu Lys Phe Leu Ser Asp Ala Ser Val Thr Ala Gly Gly Phe
225                 230                 235                 240

Gln Ile Lys Tyr Val Ala Met Asp Pro Val Ser Lys Ser Ser Gln Gly
                245                 250                 255

Lys Asn Thr Ser Thr Thr Ser Thr Gly Asn Lys Asn Phe Leu Ala Gly
            260                 265                 270

Arg Phe Ser His Leu
        275

<210> SEQ ID NO 20
<211> LENGTH: 1440
<212> TYPE: DNA
<213> ORGANISM: Homo sapiens

<400> SEQUENCE: 20

```
cagtcacatt tcagccactg ctctgagaat ttgtgagcag cccctaacag gctgttactt     60
cactacaact gacgatatga tcatcttaat ttacttattt ctcttgctat gggaagacac    120
tcaaggatgg ggattcaagg atggaatttt tcataactcc atatggcttg aacgagcagc    180
cggtgtgtac cacagagaag cacggtctgg caaatacaag ctcacctacg cagaagctaa    240
ggcggtgtgt gaatttgaag gcggccatct cgcaacttac aagcagctag aggcagccag    300
aaaaattgga tttcatgtct gtgctgctgg atggatggct aagggcagag ttggataccc    360
cattgtgaag ccagggccca actgtggatt tggaaaaact ggcattattg attatggaat    420
ccgtctcaat aggagtgaaa gatgggatgc ctattgctac aacccacacg caaaggagtg    480
tggtggcgtc tttacagatc caaagcaaat ttttaaatct ccaggcttcc caatgagta    540
cgaagataac caaatctgct actggcacat tagactcaag tatggtcagc gtattcacct    600
gagttttta gattttgacc ttgaagatga cccaggttgc ttggctgatt atgttgaaat    660
atatgacagt tacgatgatg tccatggctt tgtgggaaga tactgtggag atgagcttcc    720
agatgacatc atcagtacag gaaatgtcat gaccttgaag tttctaagtg atgcttcagt    780
gacagctgga ggtttccaaa tcaaatatgt tgcaatggat cctgtatcca aatccagtca    840
aggaaaaaat acaagtacta cttctactgg aaataaaaac tttttagctg gaagatttag    900
ccacttataa aaaaaaaaaa aaggatgatc aaaacacaca gtgtttatgt tggaatcttt    960
tggaactcct tgatctcac tgttattatt aacatttatt tattatttt ctaaatgtga   1020
aagcaataca taatttaggg aaaattggaa aatataggaa actttaaacg agaaaatgaa   1080
acctctcata atcccactgc atagaaataa caagcgttaa catttcata tttttttctt   1140
tcagtcattt ttctatttgt ggtatatgta tatatgtacc tatatgtatt tgcatttgaa   1200
```

```
-continued attttggaat cctgctctat gtacagtttt gtattatact ttttaaatct tgaactttat    1260
aaacattttc tgaaatcatt gattattcta caaaaacatg attttaaaca gctgtaaaat    1320
attctatgat atgaatgttt tatgcattat ttaagcctgt ctctattgtt ggaatttcag    1380
gtcattttca taaatattgt tgcaataaat atccttgaac acaaaaaaaa aaaaaaaaaa    1440
```

MESENCHYMAL STEM CELLS, COMPOSITIONS, AND METHODS FOR TREATMENT OF CARDIAC TISSUE DAMAGE

The invention was made with U.S. Government support under grant numbers HL073252, P40 RR 17447, P01 HL 075161 and 1R01HL080682-01A2 awarded by the National Heart, Lung, and Blood Institute of the National Institutes of Health. The United States Government has certain rights in the invention.

This application claims priority to U.S. Provisional Application Ser. No. 61/073,739, filed Jun. 18, 2008, herein incorporated by reference in its entirety for all purposes.

FIELD OF THE INVENTION

The present invention relates to compositions comprising mesenchymal stem cells (also called mesenchymal stromal cells, or MSCs), and to their novel uses for repair of cardiac damage and treatment of inflammatory diseases. The invention also relates to a protein (TSG-6) secreted by MSCs under certain conditions, and its novel use for repair of cardiac damage and treatment of inflammatory disease. The compositions of the invention may be particularly useful in restoring cardiac function following cardiac damage, including, but not limited to, myocardial infarction, as well as in reducing symptoms of inflammatory disease.

BACKGROUND OF THE INVENTION

There is currently tremendous optimism and enthusiasm for cell-based therapies for heart disease. However, cell therapy is in its early stages, and various questions remain. For example, the identification of those patients who benefit most from cell therapy, the optimal cell type and number for patient with acute and chronic diseases, the best time and way of cell delivery, and the mechanisms of action by which cells exhibit beneficial effects, need to be further evaluated."

As summarized in a recent review (Segers and Lee, 2008), there were 31 reports of clinical trials involving cell therapies in patients with MI. Of these, 14 reported statistically significant improvement in left ventricular ejection fraction, one noted decreased mortality, two did not provide sufficient data to evaluate, and 14 reported no significant improvement in ejection fraction. It is clear, however, that the significance of these results is extremely difficult to evaluate because a variety of different cells were used, including: bone marrow nucleated cells; circulating progenitor cells; CD133 hematopoietic stem cells; CD34 hematopoietic stem cells; skeletal myoblasts; MSCs; a combination of MSCs and endothelial progenitor cells; and unspecified bone marrow cells. The different studies also used significantly different criteria for selecting and evaluating patients, the nature of their controls, the number of patients enrolled, mean follow-up times, the number of cells administered, and the routes of administration. Therefore, the best that one can conclude at the moment is that cell-based therapies offer promise for patients with cardiac disease, but many aspects of the potential therapies require further study (see Segers and Lee, 2008; Dimmeler & Leri, 2008; Charwat et al., 2008; Burt et al., 2008). There is a need to better define the optimal cells, routes of administration and the mechanism by which MSCs can repair the heart. The technical problem underlying the present invention was therefore to overcome these prior art difficulties by identifying a suitable cell type for cell-based therapies for heart disease, and by identifying at least one cell-based factor responsible for improved outcomes in heart disease. The solution to this technical problem is provided by the embodiments characterized in the claims.

SUMMARY OF THE INVENTION

As indicated herein, the inventors have made considerable progress on several of the aforementioned goals as they relate to cell therapy with the stem/progenitors cells from bone marrow, referred to as mesenchymal stem cells or multipotent mesenchymal stromal cells (in either case, "MSCs"). In particular, the inventors have discovered surface epitopes that define a sub-population of MSCs (defined as RS-MSCs) that demonstrate decreased propensity to generate lethal pulmonary emboli, increased engraftment into infarcted hearts of mice, and more efficient differentiation than preparations of MSCs currently employed by most investigators in the field. The inventors demonstrate herein that after intravenous (IV) infusion of human MSCs into mice, MSCs entrapped in the lungs are activated to express extremely high levels of a pluripotent anti-inflammatory gene known as "TNFα stimulated gene 6" (TSG-6). TSG-6 is also known as "tumor necrosis factor-alpha-induced protein 6," or TNFAIP6, and its expression is also induced by interleukin-1 (IL1) and lipopolysaccharide (LPS). The expression of TSG-6 by MSCs inhibits deleterious inflammatory responses to infarction, and the functional improvements in mice with myocardial infarction (MI) are due in large part to the activation of MSCs and their expression of TSG-6. Thus, the inventors provide an explanation for the paradoxical observations reported by many others, wherein IV infusions of MSCs improve the function after myocardial infarction (MI) even though most of the infused cells are trapped in the lungs. Moreover the data suggest that at least some of the beneficial effects of cell-based therapies for MI can be obtained via: 1) infusions comprising MSCs activated by pre-incubation with TNFα, IL1, and/or LPS to express elevated levels of TSG-6; 2) infusions comprising MSCs engineered to express elevated levels of TSG-6 (e.g., transfected MSCs over-expressing TSG-6); and 3) infusions comprising recombinant TSG-6 (e.g., recombinant human TSG-6). As used herein, "infusion" contemplates both intravenous and intracardiac infusion, unless specifically modified.

Thus, in one embodiment, the invention provides a method of treating cardiac damage comprising administering to a mammal in need thereof a plurality of MSCs, wherein said MSCs are pre-activated MSCs, and further wherein said pre-activated MSCs express elevated levels of TSG-6. The invention also provides a method of treating cardiac damage comprising administering to a mammal in need thereof a plurality of MSCs, wherein said MSCs over-express TSG-6. Also provided is a method of treating cardiac damage comprising administering to a mammal in need thereof recombinant human TSG-6. The invention additionally provides an MSC, wherein said MSC has been transfected to over-express TSG-6. The invention further provides a pharmaceutically-acceptable preparation of MSCs, wherein said MSCs have been pre-activated with one or more of the following: TNFα; IL1, or LPS.

More specifically, the invention contemplates selecting and isolating TSG-6 positive cells from the population of MSCs pre-activated with one or more cytokines (e.g. so as to isolate an enriched population, i.e. a population with a reduced number of TSG-6 negative cells). In one embodiment, positive selection is achieved with an antibody to TSG-6 (e.g. an immobilized antibody for cell capture, a fluorescent antibody for cell sorting, etc.).

The invention further provides a purified population of mesenchymal stem cells (MSCs) that has been contacted with one or more ligands under conditions to express increased levels of TSG-6 protein. In a preferred embodiment, the contacting comprises in vitro treatment. In a further embodiment, the ligand comprises a cytokine, chemokine, and/or LPS.

The invention also provides a purified population of mesenchymal stem cells (MSCs) that has been contacted with one or more of TNF-alpha, IL1, and LPS under conditions to express increased levels of TSG-6 protein. In a more preferred embodiment, the purified population comprises purified rapidly self-renewing mesenchymal stem cells (RS-MSCs).

The invention also provides a purified population of rapidly self-renewing mesenchymal stem cells (RS-MSCs) that has been contacted with one or more of TNF-alpha, IL1, and LPS under conditions to express increased levels of TSG-6 protein.

The invention further provides a population of transgenic mesenchymal stem cells (MSCs) that (a) comprises a heterologous nucleotide sequence encoding TSG-6 protein, and (b) expresses the TSG-6 protein. In one preferred embodiment, the population is purified. In an alternative embodiment, the population of transgenic mesenchymal stem cells (MSCs) comprises transgenic rapidly self-renewing mesenchymal stem cells (RS-MSCs) that (a) comprise a heterologous nucleotide sequence encoding TSG-6 protein, and (b) express the TSG-6 protein. In yet a further embodiment, the transgenic rapidly self-renewing mesenchymal stem cells (RS-MSCs) are purified.

Also provided herein is a population of transgenic rapidly self-renewing mesenchymal stem cells (RS-MSCs) that (a) comprises a heterologous nucleotide sequence encoding TSG-6 protein, and (b) expresses the TSG-6 protein.

The invention additional provides a pharmaceutical composition comprising a population of any of the cells described herein.

The invention further provides a method for purifying rapidly self-renewing mesenchymal stem cells (RS-MSCs), comprising a) providing a first population of cells comprising RS-MSCs, b) contacting the population of cells with one or both of (i) an antibody that specifically binds to PODXL and (ii) an antibody that specifically binds to CD49f, and c) isolating cells that bind to the one or both of the antibodies, thereby producing a population of purified RS-MSCs. In one embodiment, the method further comprises d) contacting the population of purified RS-MSCs with one or more of TNF-alpha, IL1, and LPS under conditions to produce a contacted population of cells that expresses increased levels of TSG-6 protein compared to TSG-6 protein levels expressed by the population of purified RS-MSCs. In yet another embodiment, the increased levels of TSG-6 protein are from 10 fold to 500 fold. In a further embodiment, the method further comprises d) transfecting the population of purified RS-MSCs with a nucleotide sequence that encodes TSG-6 protein. The invention further contemplates a purified population of rapidly self-renewing mesenchymal stem cells (RS-MSCs) produced by any of the methods described in this paragraph.

The invention also provides a method for reducing one or more symptoms of cardiac muscle cell necrosis in a mammalian subject comprising a) providing i) a mammalian subject in need of reducing one or more symptoms of cardiac muscle cell necrosis, and ii) a composition comprising purified tumor necrosis facto-alpha stimulated gene 6 (TSG-6) protein, and b) administering a therapeutically effective amount of the composition to the mammalian subject, thereby reducing one or more symptoms of the cardiac muscle cell necrosis. Without limiting the route of administration, in one embodiment, administering is selected from the group consisting of intramuscular administration into cardiac muscle and intravenous administration. In a further embodiment, the TSG-6 protein is purified from a transgenic cell that (a) comprises a heterologous nucleotide sequence encoding TSG-6 protein, and (b) expresses the TSG-6 protein.

The invention also provides a method for reducing one or more symptoms of cardiac muscle cell necrosis in a mammalian subject comprising a) providing i) a mammalian subject in need of reducing one or more symptoms of cardiac muscle cell necrosis, and ii) a population of purified mesenchymal stem cells (MSCs) that has been contacted with one or more chemokine, cytokine and LPS under conditions to express increased levels of TSG-6 protein, and b) administering a therapeutically effective amount of the population of purified mesenchymal stem cells (MSCs) to the mammalian subject, thereby reducing one or more symptoms of the cardiac muscle cell necrosis. In a particular embodiment, the population of purified mesenchymal stem cells (MSCs) comprises purified rapidly self-renewing mesenchymal stem cells (RS-MSCs). In a further embodiment, the step of administering is selected from the group consisting of intramuscular administration into cardiac muscle and intravenous administration.

In addition, the invention provides a method for reducing one or more symptoms of cardiac muscle cell necrosis in a mammalian subject comprising a) providing i) a mammalian subject in need of reducing one or more symptoms of cardiac muscle cell necrosis, ii) a population of transgenic mesenchymal stem cells (MSCs) that (a) comprises a heterologous nucleotide sequence encoding TSG-6 protein, and (b) expresses the TSG-6 protein, and b) administering a therapeutically effective amount of the population of transgenic mesenchymal stem cells (MSCs) to the mammalian subject, thereby reducing one or more symptoms of the cardiac muscle cell necrosis. In one embodiment, the population of transgenic mesenchymal stem cells (MSCs) comprises purified rapidly self-renewing mesenchymal stem cells (RS-MSCs). In a further embodiment, the step of administering is selected from the group consisting of intramuscular administration into cardiac muscle and intravenous administration.

The invention also provides a method for reducing one or more symptoms of sterile inflammation in a mammalian subject comprising a) providing i) a mammalian subject in need of reducing one or more symptoms of sterile inflammation in a tissue, and ii) a population of purified mesenchymal stem cells (MSCs) that has been contacted with one or more of TNF-alpha, IL1, and LPS under conditions to express increased levels of TSG-6 protein, and b) administering a therapeutically effective amount of the population of purified mesenchymal stem cells (MSCs) to the mammalian subject, thereby reducing one or more symptoms of the sterile inflammation in the tissue. In one embodiment, the population of purified mesenchymal stem cells (MSCs) comprises purified rapidly self-renewing mesenchymal stem cells (RS-MSCs). In a further embodiment, the step of administering is selected from the group consisting of intramuscular administration into cardiac muscle and intravenous administration. In another embodiment, the tissue comprises cardiac muscle tissue, and administering is selected from the group consisting of intramuscular administration into the cardiac muscle tissue and intravenous administration. In another embodiment, the subject has, or is at risk of having, a sterile inflammatory disease.

Also provided is a method for reducing one or more symptoms of sterile inflammation in a mammalian subject comprising a) providing i) a mammalian subject in need of reducing one or more symptoms of sterile inflammation in a tissue, ii) a population of transgenic mesenchymal stem cells (MSCs) that (a) comprises a heterologous nucleotide sequence encoding TSG-6 protein, and (b) expresses the TSG-6 protein, and b) administering a therapeutically effective amount of the population of transgenic mesenchymal stem cells (MSCs) to the mammalian subject, thereby reducing one or more symptoms of the sterile inflammation in the tissue. In one embodiment, the population of transgenic mesenchymal stem cells (MSCs) comprises purified rapidly self-renewing mesenchymal stem cells (RS-MSCs). In another embodiment the tissue comprises cardiac muscle tissue, and administering is selected from the group consisting of intramuscular administration into the cardiac muscle tissue and intravenous administration. In an alternative embodiment, the subject has, or is at risk of having, a sterile inflammatory disease.

The invention also provides a method for reducing one or more symptoms of sterile inflammation in a mammalian subject comprising a) providing i) a mammalian subject in need of reducing one or more symptoms of sterile inflammation in a tissue, and ii) a composition comprising purified tumor necrosis facto-alpha stimulated gene 6 (TSG-6) protein, and b) administering a therapeutically effective amount of the composition to the mammalian subject, thereby reducing one or more symptoms of the sterile inflammation in the tissue. In one embodiment, the tissue comprises cardiac muscle tissue, and administering is selected from the group consisting of intramuscular administration into the cardiac muscle tissue and intravenous administration. In an alternative embodiment, the subject has, or is at risk of having, a sterile inflammatory disease. In a further embodiment, the TSG-6 protein is purified from a transgenic cell that comprises a heterologous nucleotide sequence encoding TSG-6 protein, and that expresses the TSG-6 protein.

The invention additionally provides a method for detecting sterile inflammation in a tissue in a mammalian subject comprising a) providing a mammalian subject in need of reducing one or more symptoms of sterile inflammation in a tissue, and b) detecting an increase in serum level of two or more (including three, four, five and six) of plasmin activity, macrophage chemoattractant protein-1 (MCP-1), macrophage inflammatory protein-1 alpha (MIP-1 alpha), beta thromboglobulin, soluble ST2 receptor, C-reactive protein (CRP), and natriuretic peptide compared to a control mammalian subject lacking the sterile inflammation in the tissue. In one embodiment, the tissue comprises cardiac muscle tissue. In another embodiment, the method further comprises c) administering to the subject a therapeutically effective amount of one or more of i) a composition comprising purified tumor necrosis factor-alpha stimulated gene 6 (TSG-6) protein, ii) a population of purified mesenchymal stem cells (MSCs) that has been contacted with one or more of TNF-alpha, IL1, and LPS under conditions to express increased levels of TSG-6 protein, and ii) a population of transgenic mesenchymal stem cells (MSCs) that comprises a heterologous nucleotide sequence encoding TSG-6 protein and expresses the TSG-6 protein, wherein the administering produces a treated subject, and d) detecting, in the treated subject, a reduction in serum level of two or more of the plasmin activity, MCP-1, MIP-1alpha, beta thromboglobulin, soluble ST2 receptor, CRP, and natriuretic peptide, compared to the serum level that is detected in step b).

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements.

FIG. 1 shows the use of microarrays as a preliminary screen for useful surface epitopes.

FIG. 3 shows FACScans of changes in the epitopes in MSCs with expansion in culture.

FIG. 5, Top Left: Intravenously infused hMSCs were cleared from blood in less than 5 minutes (min). Total recovery of Alu sequences for seven other tissues are indicated by lower curve and numbers inserted. FIG. 5, Top Right: hMSCs infused into the left ventricle of the heart were also cleared in less than 5 min. FIG. 5, Bottom Left: Tissue distribution of human Alu sequences 15 min after IV infusion of hMSCs, a breast cancer cell line (MDAMB-231), and human WBCs. FIG. 5, Bottom Right: Distribution 15 min after IC infusion of hMSCs and the cancer cell line.

FIG. 6 shows the tissue distribution (expressed as % of infused cells) of IV infused hMSCs ($2 \times 10^6$).

FIG. 8, Top Left: Real time RT-PCR assays of hMSCs (Passage 2 and 3) and fibroblasts incubated in serum-free medium with 10 ng/ml TNFα. FIG. 8, Top Right: Western blots of cell lysates. Some of the TSG-6 was recovered in larger molecular forms apparently because of its tight binding to hyaluronan and other proteins. FIG. 8, Middle Left: ELISA assays of medium from hMSCs and fibroblasts (Fibros). FIG. 8, Middle Right: Western blots of conditioned medium (first four lanes) and loading control (second four lanes, Coomassie stained). FIG. 8, Bottom Left: Real-time RT-PCR assays of TSG-6 of hMSCs after transduction with siRNA to TSG-6. FIG. 8, Bottom Right: ELISA assays for TSG-6 in medium from samples in FIG. 8, Bottom Left.

FIG. 9 FIG. 9 shows the effects of IV hMSCs in mice with MI. Permanent MI was induced in mice and $2 \times 10^6$ hMSCs or 100 micrograms recombinant TSG-6 were infused into a tail vein after 1 hour. Serum or hearts were collected 48 hr later.

FIG. 19 shows (A) the TSG-6 amino acid sequence (SEQ ID NO: 19) and (B) nucleotide sequence encoding *Homo sapiens* tumor necrosis factor, alpha-induced protein 6 (TSG-6) (TNFAIP6) (GenBank No. NM_007115) (SEQ ID NO: 20).

DEFINITIONS

Figure 1A:
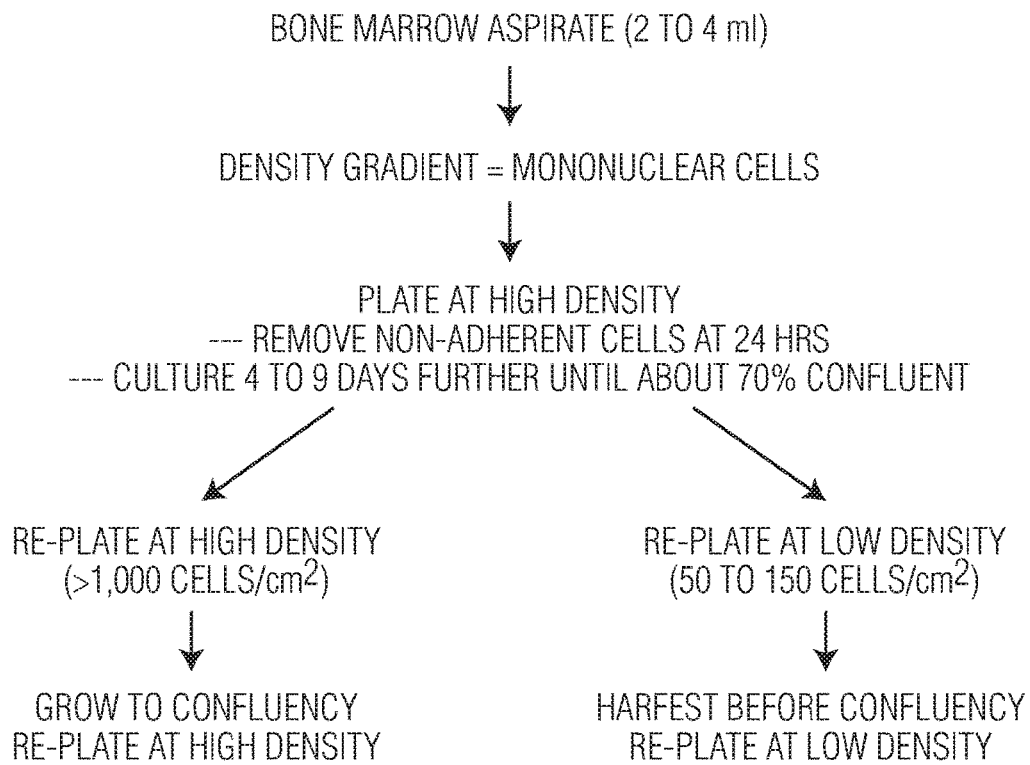
FIG. 1A is a schematic of two protocols used to prepare human MSCs. High density cultures are employed by many investigators; low density cultures are designed to retain RS-MSCs.

To facilitate understanding of the invention, a number of terms are defined below.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

The terms "cells" and "population of cells" interchangeably refer to a plurality of cells, i.e., more than one cell. The population may be a pure population comprising one cell type. Alternatively, the population may comprise more than one cell type. In the present invention, there is no limit on the number of cell types that a cell population may comprise.

"Mesenchymal stem cell," "MSC," "bone marrow stromal cells" and "multipotent stromal cell," are interchangeably used to refer to a cell derived from bone marrow (reviewed in Prockop, 1997), peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005). MSCs are characterized by their ability to adhere to plastic tissue culture surfaces (Friedenstein et al.; reviewed in Owen & Friedenstein, 1988), and by being an effective feeder layers for hematopoietic stem cells (Eaves et al., 2001). In addition, MSCs can be differentiated both in culture and in vivo into osteoblasts and chondrocytes, into adipocytes, muscle cells (Wakitani et al., 1995) and cardiomyocytes (Fukuda and Yuasa, 2006), into neural precursors (Woodbury et al., 2000; Deng et al., 2001, Kim et al., 2006; Mareschi et al., 2006; Krampera et al., 2007). Mesenchymal stem cells (MSCs) may be purified using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007).

"Rapidly self-renewing mesenchymal stem cell," "RS-MSC" and "type I mesenchymal stem cell" are interchangeably used to refer to an early progenitor cell. They are typically spindle shaped and are present in early-passage MSCs plated at low density. Rapidly self-renewing mesenchymal stem cells (RS-MSCs) may be purified from bone marrow cells and/or from a purified population of mesenchymal stem cells (MSCs) using methods described herein (e.g., binding to one or more of antibody that specifically binds to PODXL, and antibody that specifically binds to CD49f).)

"Slowly replicating mesenchymal stem cell," "type II mesenchymal stem cell" and "SR-MSC" are interchangeably used to refer to an early progenitor cell. The cells are larger in size than RS-MSC, and are present in early-passage MSCs plated at low density. Typically, SR-MSCs arise from RS-MSCs as the cultures expand to confluency.

The terms "reduce," "inhibit," "diminish," "suppress," "decrease," and grammatical equivalents (including "lower," "smaller," etc.) when in reference to the level of any molecule (e.g., amino acid sequence such as PODXL protein, CD49f protein, TSG-6 protein, MCP-1, MIP-1 alpha, beta thromboglobulin, soluble ST2 receptor, CRP, natriuretic peptide, antibody that specifically binds to PODXL, antibody that specifically binds to CD49f protein, antibody that specifically binds to TSG-6 protein, etc., and nucleic acid sequence such as those encoding any of the polypeptides described herein), cell (e.g., bone marrow cell, mesenchymal stem cell (MSC), rapidly self-renewing mesenchymal stem cell (RS-MSC), slowly replicating mesenchymal stem cell (SR-MSC), etc.), and/or phenomenon (e.g., plasmin activity, symptom of a disease, cell proliferation, cell differentiation, cell engraftment, cell death, cell apoptosis, cell viability, cell survival, binding to a molecule, affinity of binding, expression of a nucleic acid sequence, transcription of a nucleic acid sequence, enzyme activity, etc.) in a first sample (or patient) relative to a second sample (or in a treated patient), mean that the quantity of molecule, cell, and/or phenomenon in the first sample (or patient) is lower than in the second sample (or in a treated patient) by any amount that is statistically significant using any art-accepted statistical method of analysis. In one embodiment, the reduction may be determined subjectively, for example when a patient refers to their subjective perception of disease symptoms, such as pain, fatigue, difficulty in breathing, clarity of vision, nausea, etc. In another embodiment, the quantity of molecule, cell, and/or phenomenon in the first sample is lower by any numerical percentage from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100% lower than the quantity of the same molecule, cell and/or phenomenon in a second sample.

The terms "increase," "elevate," "raise," and grammatical equivalents (including "higher," "greater," etc.) when in reference to the level of any molecule (e.g., amino acid sequence such as PODXL protein, CD49f protein, TSG-6 protein, MCP-1, MIP-1alpha, beta thromboglobulin, soluble ST2 receptor, CRP, natriuretic peptide, antibody that specifically binds to PODXL, antibody that specifically binds to CD49f protein, antibody that specifically binds to TSG-6 protein, etc., and nucleic acid sequence such as those encoding any of the polypeptides described herein), cell (e.g., bone marrow cell, mesenchymal stem cell (MSC), rapidly self-renewing mesenchymal stem cell (RS-MSC), slowly replicating mesenchymal stem cell (SR-MSC), etc.), and/or phenomenon (e.g., plasmin activity, symptom of a disease, cell proliferation, cell differentiation, cell engraftment, cell death, cell apoptosis, cell viability, cell survival, binding to a molecule, affinity of binding, expression of a nucleic acid sequence, transcription of a nucleic acid sequence, enzyme activity, etc.) in a first sample (or patient) relative to a second sample (or treated patient), mean that the quantity of the molecule, cell and/or phenomenon in the first sample (or patient) is higher than in the second sample (or in a treated patient) by any amount that is statistically significant using any art-accepted statistical method of analysis. In one embodiment, the increase may be determined subjectively, for example when a patient refers to their subjective perception of disease symptoms, such as pain, fatigue, difficulty in breathing, clarity of vision, nausea, etc. In another embodiment, the quantity of molecule, cell, and/or phenomenon in the first sample is higher by any numerical percentage, such as at least 10% greater than, at least 25% greater than, at least 50% greater than, at least 75% greater than, and/or at least 90% greater than the quantity of the same molecule, cell and/or phenomenon in a second sample. In yet a further embodiment, the quantity of molecule, cell, and/or phenomenon in the first sample is higher by any numerical amount from 5 fold to 1000 fold, including from 5 fold to 500 fold, 10 fold to 400 fold, from 20 fold to 300 fold, from 30 fold to 200 fold, from 40 fold to 200 fold, from 50 fold to 200 fold.

"Cardiac infarction," "myocardial infarction," "MI," "acute myocardial infarction," and "AMI" are commonly known as a heart attack, which occurs when the blood supply to part of the heart is interrupted causing myocardial muscle cell necrosis. This is most commonly due to occlusion (blockage) of a coronary artery following the rupture of a vulnerable atherosclerotic plaque. The resulting ischemia (restriction in blood supply) and oxygen shortage, if left untreated for a sufficient period of time, can cause damage and/or death (infarction) of heart muscle tissue (myocardium).

The terms "treating," "treatment" and grammatical equivalents when in reference to a disease (e.g., cardiac infarction, cardiac muscle cell necrosis, inflammation, etc.) encompasses delaying and/or reducing the level of one or more objective symptoms and/or one or more subjective symptoms.

"Tumor necrosis factor-alpha stimulated gene 6 protein," "TSG-6 protein," "TNF-α stimulated gene 6 protein," and "TNFAIP6 protein" are used interchangeably to refer to a secretory protein that contains a hyaluronan-binding domain, and thus is a member of the hyaluronan-binding protein family. The hyaluronan-binding domain is known to be involved in extracellular matrix stability and cell migration. This protein has been shown to form a stable complex with inter-alpha-inhibitor (I alpha I), and thus enhance the serine protease inhibitory activity of I alpha I, which is important in the protease network associated with inflammation. The expression of this gene can be induced by tumor necrosis factor alpha and interleukin-1. The expression can also be induced by mechanical stimuli in vascular smooth muscle cells, and is found to be correlated with proteoglycan synthesis and aggregation. TSG-6 protein is exemplified by the homo sapiens amino acid sequence of FIG. 19A, which is encoded by the nucleotide sequence of FIG. 19B (GenBank No. NM_007115). Recombinant purified human TSG-6 protein is commercially available (R&D Systems, Inc., Minneapolis, Catalog #2104-TS-050). Antibodies that specifically bind to TSG-6 are commercially available (ELISA, monoclonal antibody specific for TSG-6 (clone A38.1.20; Santa Cruz Biotechnology, Inc., Catalog #BAF2104; biotinylated anti-human TSG-6 (TSG-6 Biotinylated PAb Detection Antibody; R&D Systems, Inc., Minneapolis).

"PODXL," "podocalyxin-like 2," "endoglycan," "PODLX2," "Podocalyxin-like protein 2 precursor," and "UNQ1861/PRO3742" are interchangeably used, and are exemplified by GenBank Accession no. NM_015720, encoded by mRNA (GenBank) AF219137. Antibodies that specifically bind to PODXL are known in the art, including FITC Labeled anti-Human PCLP1 (Cat. #M084-4, MBL International Corporation, Woburn, Mass.).

"CD49f" "alpha6-integrin" "integrin, alpha 6" and "ITGA6" protein product is the integrin alpha chain alpha 6. Integrins are integral cell-surface proteins composed of an alpha chain and a beta chain. A given chain may combine with multiple partners resulting in different integrins. For example, alpha 6 may combine with beta 4 in the integrin referred to as TSP180, or with beta 1 in the integrin VLA-6. Integrins are known to participate in cell adhesion as well as cell-surface mediated signaling. Two transcript variants encoding different isoforms have been found for this gene. The amino acid sequence and nucleotide sequence of the exemplary homo sapiens integrin, alpha 6 (ITGA6), transcript variant 2, are described in GenBank Accession No. NM_000210. Homo sapiens chromosome 2, reference assembly, complete sequence is described in GenBank Accession No. NC_000002.11. Antibodies that specifically bind to CD49f are known in the art including PE-Cy5 Rat anti-Human CD49f (Cat. #551129, BD PharMingen/BD Biosciences.

DETAILED DESCRIPTION OF THE INVENTION

The present invention provides compositions comprising mesenchymal stem cells (MSCs), and methods for their novel use in the repair of cardiac damage and treatment of inflammatory diseases. The invention also provides methods for using TSG-6 protein, that is secreted by MSCs under certain conditions, for repair of cardiac damage and treatment of inflammatory disease. The compositions of the invention may be particularly useful in restoring cardiac function following cardiac damage, including, but not limited to myocardial infarction, as well as in reducing symptoms of inflammatory disease. The inventors disclose herein: (i) the identification of new epitopes that can—for the first time—provide quantitative data on the RS-MSC content of preparations of MSCs; (ii) that RS-MSCs are more clonogenic, have a greater potential to differentiate in culture, and more effective engraft into MI heart and other tissues in mice than the confluent cultures of MSCs (SR-MSCs) employed by most other investigators; (iii) that heart function in MI mice improves after IV infusions of hMSCs because the cells trapped in the lung are activated to secrete large amounts of the multifunctional anti-inflammatory protein TSG-6 that inhibits serine proteinases in the injured heart; and (iv) that some of the protective effects of hMSCs in MI can be reproduced by systemic infusion of rhTSG-6.

The invention is further described under (A) Mesenchymal stromal cells (MSCs), (B) Intravenous hMSCs improve myocardial infarction in mice because cells embolized in the lung are activated to secrete the anti-inflammatory protein TSG-6, (C) Preactivated mesenchymal stem cells (MSCs), and/or preactivated rapidly self-renewing mesenchymal stem cells (RS-MSCs), that overexpress TSG-6 protein, (D) Transgenic mesenchymal stem cells (MSCs), and/or transgenic rapidly self-renewing mesenchymal stem cells (RS-MSCs), that overexpress TSG-6 protein, (E) Pharmaceutical Compositions, (F) Methods for purifying RS-MSCs, (G) Methods for treating cardiac muscle damage by administering preactivated MSCs and/or preactivated RS-MSCs, (H) Methods for treating cardiac muscle damage by administering transgenic MSCs and/or transgenic RS-MSCs, (I) Methods for treating cardiac muscle damage by administering TSG-6 protein, (J) Methods for treating sterile inflammation using preactivated MSCs and/or preactivated RS-MSCs, (K) Methods for treating sterile inflammation using transgenic MSCs and/or transgenic RS-MSCs, (L) Methods for treating sterile inflammation by administering TSG-6 protein, and (M) Methods for detecting inflammation using biomarkers.

A. Mesenchymal Stromal Cells (MSCs)

Initial experiments carried out over a century ago suggested that blood-borne cells from bone marrow of mammals may participate in tissue repair and regeneration (reviewed in Prockop, 1997). Some of the first direct evidence for bone marrow cells that might contribute to the repair of multiple tissues were published over 40 years ago by Friedenstein et al. (reviewed in Owen & Friedenstein, 1988) who demonstrated that a small fraction of cells from bone marrow that adhere to tissue culture surfaces can be differentiated both in culture and in vivo into osteoblasts and chondrocytes. Later, the same plastic adherent cells from bone marrow were found to be effective feeder layers for hematopoietic stem cells (see Eaves et al., 2001). The initial observations by Friedenstein et al. were confirmed and extended by a large number of subsequent investigators (Castro-Malaspina et al., 1980; Mets and Verdonk, 1981; Piersma et al., 1983; Owen and Friedenstein, 1988; Caplan, 1990; Prockop, 1997). The further work demonstrated that the cells can also differentiate in culture into adipocytes, muscle cells (Wakitani et al., 1995) and cardiomyocytes (Fukuda and Yuasa, 2006). Initial reports by the inventors that MSCs can differentiate into neural precursors (Woodbury et al., 2000; Deng et al., 2001) were criticized as inconclusive, but there have been persistent reports by other laboratories that MSCs can differentiate in culture to cells that display the electrophysiological properties of neural cells (Kim et al., 2006; Mareschi et al., 2006; Krampera et al., 2007). In addition, cells with properties very similar to bone marrow MSCs were identified in a large number of tissues, including peripheral blood (Kuznetsov et al., 2001), adipose tissue (Guilak et al., 2004), umbilical cord blood (Rosada et al., 2003), synovial membranes (De Bari et al., 2001), and periodontal ligament (Seo et al., 2005). The results suggested the presence of an extensive network of MSC-like stem/progenitor cells in many tissues. This network probably comprises the first responders to injury but then can be replenished by MSCs from the bone marrow in time of need.

Bone marrow MSCs have attracted attention in efforts to develop cell therapies (Caplan, 1990; Prockop, 1997; Prockop et al., 2003; Caplan, 2005), because they are readily obtained from patients and expanded in culture. The first clinical trial with MSCs was in patients with severe osteogenesis imperfecta (Horwitz et al., 1999; 2002), a disease of brittle bones caused by mutations in the genes for type I collagen (Prockop, 1985; Prockop & Kivirrikko, 1995). The trial was designed on the basis of data from experiments in a transgenic mouse model developed in our laboratory (Pereira et al., 1998). Subsequent trials were in patients with mucopolysaccharidoses (Koc et al., 2002), and then in patients with graft-versus-host disease (GVHD), which capitalized on the ability of the cells to suppress immune reactions (Aggarwal & Pittenger, 2005; Ringden et al., 2006). The recent explosion of new clinical trials with MSCs is prompted largely by three biotech companies that successfully launched initial public offerings (IPOs) within the last year and a half. The first of these companies, Osiris Therapeutics (Baltimore, Md.), has announced clinical trials in arthritis, heart disease, Crohn's disease (Phase III), and type 1 diabetes (Phase II) and graft-versus-host-disease (Phase III). Other groups have announced trials a broader range of diseases including stroke.

Although MSCs originally attracted interest because of their stem-like properties to differentiate into multiple cellular phenotypes, more recent observations presented a paradox: the cells frequently repair injured tissues without much evidence of either engraftment or differentiation. For example, in the first clinical trial in which MSCs were used to treat children with severe osteogenesis imperfecta (Horwitz et al., 1999, 2002), children improved in growth rates and other symptoms. However, assays of tissues from the children revealed that less than 1% of the donor MSCs had engrafted. Similar observations of functional improvement were made subsequently in a series of animal models for diseases, including parkinsonism, spinal cord injury, stroke, and myocardial infarction (reviewed in Prockop et al., 2003; Prockop, 2007; Caplan & Dennis, 2006). In myocardial infarction, for example, some investigators have observed differentiation of MSCs into cardiomyocytes following MI (Fukuda & Yuasa, 2006). Most, though, reported improved function with little long term engraftment of MSCs into infarcted heart (see Mishra, 2008), an observation the inventors confirmed after IV infusion of human MSCs into immunodeficient mice with MI (Iso et al., 2007). Therefore, there has been a paradigm shift in the explanations as to how MSCs can repair injured tissues. There is now renewed interest in the early observations that MSCs provide effective feeder layers for hematopoietic cells (see Eaves et al., 2001), because they secrete a variety of cytokines and chemokines (see Zacharek et al., 2007; Schinkothe et al. 2008; Penolazzi et al., 2007).

The paradigm shift has been supported by recent evidence that MSCs respond to cross-talk with injured tissues to enhance repair via a number of different mechanisms, including: 1) enhanced proliferation and differentiation of tissue-endogenous stem/progenitor cells; 2) rescue of ischemic cells by transfer of mitochondria or mitochondrial DNA; 30 suppression of excessive inflammatory responses; and 4) suppression of excessive immune reactions.

The inventors observed that injection of human MSCs into the dentate gyrus of the hippocampus of mice enhanced proliferation, migration and neural differentiation of the endogenous neural stem cells of the mouse (Muñoz et al, 2005). Without limiting the invention to a particular mechanism, such stimulation of tissue-endogenous stem/progenitor cells may in part explain the inventors' subsequent observations that intracardiac infusions of hMSCs lowered plasma sugar and increased mouse insulin in immunodeficient mice in which diabetes was induced with streptozotocin (Lee et al., 2006a).

The inventors also observed that after human MSCs were cocultured with a line of pulmonary epithelial cells with non-functional mitochondria (A549 $\rho^0$ cells), rescued clones of the A549 $\rho^0$ cells with full mitochondrial function were recovered (Spees et al., 2006). Genetic assays indicated that the rescued clones had received mitochondrial DNA from the MSCs without any transfer of genomic DNA or other evidence of cell fusion. Without limiting the invention to a particular mechanism, since loss of functional mitochondria is an early consequence of ischemia, MSCs may in part rescue ischemic injury to myocardium or other tissues since one of the earliest events in ischemic injury is loss of mitochondrial function.

Persistent chronic inflammation is now recognized as a contributing factor in a wide variety of diseases ranging from parkinsonism (Tansey et al., 2007; McGeer and McGeer 2007) to diabetes (Theuma and Fonseca 2004; Shoelson et al., 2007). A series of recent reports have emphasized that inflammatory responses to tissue injury in mammals are frequently excessive, and require cell mediators to actively suppress the responses and thereby improve tissue repair (Schwab et al., 2007; Serhan et al., 2008). One class of inflammation suppressors comprises the lipids referred to as lipoxins, resolvins and protectins (Sehran et al., 2008). A series of recent reports, though, indicate that MSCs provide another mechanism for suppressing inflammation because they can be activated to secrete peptides and proteins that modulate both inflammation and immune responses. Secretion by MSCs of the interleukin 1 (IL1) receptor antagonist apparently explained the improvements observed with administration of MSCs in a lung model of fibrosis induced by bleomycin (Ortiz et al., 2007). Intratracheal administration of MSCs suppressed inflammation and prolonged survival of mice by expression of MIP-1 and other cytokines after acute lung inflammation was induced with LPS (Gupta et al., 2007). As indicated in below, the inventors have observed that when human MSCs are infused intravenously into mice, most of the cells are trapped in the lungs and activated to secrete the pluripotent anti-inflammatory protein TSG-6 (Getting et al. 2002; Wisniewski and Vilcek 2004; Forteza et al., 2007; Milner et al., 2006).

A series of reports demonstrated that MSCs suppressed mixed lymphocyte reactions in culture, produced improvements in an animal model for multiple sclerosis (Gerdoni et al., 2007), and improved patients with graft versus host disease (Aggarwal & Pittenger, 2005; Le Blanc & Ringden, 2007). Recently, the mechanisms of immune suppression by MSCs were defined (Ren et al., 2008): MSCs are activated by IFNγ, together with one of three other pro-inflammatory cytokines to attract T lymphocytes. The MSCs then secrete nitrous oxide to suppress the T lymphocytes. The inventors recently observed that human MSCs injected into the hippocampus of mice after transient global ischemia are activated to reduce neurological deficits and neuron death by suppressing both inflammatory and immune reactions (Ohtaki et al., 2008).

A number of investigators have independently observed that MSCs can produce beneficial effects by IV administration both in animal models (Pereira et al., 1998; Akiyama et al., 2002; Chen et al., 2003; Nomura et al., 2005; Wu et al., 2008), and in patients (Horwitz et al., 1999, 2002; Koc et al., 2002; Ringden et al., 2006). The results are surprising, since it has been convincingly demonstrated that most MSCs that are infused IV are rapidly trapped in the lung (Gao et al., 2001; Schrepfer et al., 2007). Trapping of MSCs in the lung is not in itself unexpected, since it also occurs with polymorphonuclear (PMN) cells (Hogg et al., 1994), metastatic tumors (MacDonald et al., 2002), and probably hematopoietic stem cells (Dooner et al., 2004). However, it was not clear how MSCs trapped in the lung could enhance repair of the heart, brain and other tissues. Hence, the present inventors' observations on the effects of IV infusions into mice with MI (as presented below) represent a significant advance.

B. Intravenous hMSCs Improve Myocardial Infarction in Mice Because Cells Embolized in Lung are Activated to Secrete the Anti-Inflammatory Protein TSG-6

Data herein show data obtained using quantitative assays for human DNA and mRNA, which were used to examine the paradox that intravenously (IV) infused human multipotent stromal cells (hMSCs) can enhance tissue repair without significant engraftment. After $2 \times 10^6$ hMSCs were IV infused into mice, most of the cells were trapped as emboli in lung. The cells in lung disappeared with a half-life of about 24 hr but <1,000 cells appeared in 6 other tissues. The hMSCs in lung up-regulated expression of multiple genes with a large increase in the anti-inflammatory protein TSG-6. After myocardial infarction, IV hMSCs but not hMSCs transduced with TSG-6 siRNA decreased inflammatory responses, reduced infarct size, and improved cardiac function. IV administration of recombinant TSG-6 also reduced inflammatory responses and reduced infarct size. The results suggest improvements in animal models and patients after IV infusions of MSCs are at least in part explained by activation of MSCs to secrete TSG-6.

The inventors first developed assays to provide quantitative data on the fate of human cells infused into mice. The inventors then demonstrated that IV infused human MSCs (hMSCs) produced functional improvement in mice with myocardial infarction (MI) at least in part because the cells trapped as emboli in lung are activated to express the anti-inflammatory factor TNF-α induced protein 6 (TNAIP6 or TSG-6).

The hMSCs trapped in mouse lung after IV infusion underwent major changes in their patterns of gene expression in response to the injury to the lung produced by micro-embolization of the cells in the pulmonary vasculature (Furlani et al., 2009; Lee et al., 2009). The up-regulation of the human TSG-6 was of special interest because of the anti-inflammatory effects of the protein (Milner et al., 2006; Wisniewski and Vilcek, 2004), and because excessive inflammatory responses contribute to the pathological changes produced by MI (Ovechkin et al., 2005; Paolocci et al., 2006; Carvalho et al., 2006; Fang et al., 2007; Moshal et al., 2008). Therefore the results suggested a possible explanation for the observations that IV infusions of MSCs improved cardiac function in models for MI (Halkos et al., 2008; Iso et al., 2007; Krause et al., 2007; Wolf et al., 2007). In the mouse model for MI, knock down of TSG-6 expression in hMSCs largely negated the improvements in inflammatory responses, infarct size and cardiac function produced by IV fusions of hMSCs. In addition, IV infusions of rhTSG-6 largely duplicated the therapeutic effects of the hMSCs on inflammatory responses and infarct size. Therefore the results indicated that the hMSCs that were trapped in the lung were activated to secrete TSG-6, and the TSG-6 suppressed the excessive inflammatory response to LAD so as to decrease the proteolytic damage to the heart and the subsequent fibrotic scarring and decrease in cardiac function. The 1,500 or so of hMSCs transiently appeared in the infracted heart after infusion of $10^6$ hMSCs may also have contributed to the anti-inflammatory effects.

The up-regulation of TSG-6 was detected by the cross-species strategy of infusing hMSCs into NOD/scid mice. Similar strategies of using hMSCs in animal models previously proved useful, because the hMSCs provided numerous endogenous markers for the cells and no obvious cross-species artifacts were encountered (Hwang et al., 2008; Lu et al., 2009; Bai et al., 2009; Gonzalez-Rey et al., 2009; Sasportas et al., 2009), apparently because of the immune modulatory effects of the cells (Uccelli et al., 2008). Also, the strategy of using hMSCs avoids the technical difficulties of isolating mouse MSCs (Baddoo et al., 2003; Gnecchi and Melo, 2009; Peister et al., 2004; Sung et al., 2008), and the marked tendency of mouse MSCs to develop genomic instability and become tumorgenic as they are expanded in culture (Sung et al., 2008; Tolar et al., 2007). Permanent LAD ligation in mice does not mimic human MI as closely as ischemia and reperfusion models in larger animals. However, permanent LAD ligation in NOD/scid mice provided a useful model for testing the effects on hMSCs because the mice retained the excessive inflammatory responses to MI (Iso et al., 2007).

TSG-6 is a 30 kDa glycoprotein (Heng et al., 2008; Milner et al., 2006) that was shown to produce three distinct anti-inflammatory effects (Milner et al., 2006; Wisniewski and Vilcek, 2004). (a) It inhibits the inflammatory network of proteases primarily by increasing the inhibitory activity of inter-α-inhibitor; (b) it binds to fragments of hyaluronan and thereby blunt their pro-inflammatory effects; (c) it inhibits neutrophil infiltration into sites of inflammation. In transgenic mice, inactivation of the gene increased inflammatory responses (Szanto et al., 2004) and over-expression of the gene decreased inflammatory responses (Mindrescu et al., 2002). Also, administration of the recombinant protein improved arthritis in several murine models (Bardos et al., 2001; Mindrescu et al., 2000). Although TSG-6 was originally discovered by screening cDNA libraries from fibroblasts incubated with TNF-α (Lee et al., 1992), the results here demonstrated that hMSCs produced far more TSG-6 in response to TNF-α than dermal fibroblasts.

The hMSCs trapped in lung secreted additional cardio-protective factors in addition to TSG-6. The effects of rhTSG-6 on infarct size in the mice were slightly less than the effects of IV infusions of hMSCs. MSCs in culture and in response to chemokines or injured cells secrete large amounts of therapeutic factors such as TGF-β, HGF, IL-4, IL-10, PGE2 and stanniocalcin-1 (Caplan, 2009; Gnecchi et al., 2008; Block et al., 2009; Ohtaki et al., 2008). TSG-6 may however play a key role in many beneficial effects of MSCs. Inflammatory responses to sterile tissue injury are frequently excessive and require active suppression (Schwab et al., 2007). Also, chronic inflammation plays a key role in diseases such as diabetes, stroke, Alzheimer's disease and parkinsonism (Bergsbaken et al., 2009; McCombe and Read, 2008; Shoelson et al., 2006; Theuma and Fonseca, 2004). Therefore secretion of TSG-6 by MSCs trapped as emboli in lung may in part explain the therapeutic effects observed after IV infusions of MSCs in animal models for these and other diseases (Uccelli et al., 2008; Ezquer et al., 2008; Parr et al., 2007). Secretion of TSG-6 may also play a role in therapies for heart disease with other cells such as skeletal myoblasts, fetal myoblasts and ES cells (Jolicoeur et al., 2007).

C. Preactivated Mesenchymal Stem Cells (MSCs), and/or Preactivated Rapidly Self-Renewing Mesenchymal Stem Cells (RS-MSCs), that Over-Express TSG-6 Protein In one embodiment, the invention provides a purified population of mesenchymal stem cells (MSCs) that has been contacted with one or more ligand selected from the group consisting of pro-inflammatory chemokine, pro-inflammatory cytokine (e.g., TNF-alpha and IL1), and LPS, under conditions to express increased levels of TSG-6 protein. In a particular embodiment, the purified population of mesenchymal stem cells (MSCs) comprises purified rapidly self-renewing mesenchymal stem cells (RS-MSCs). Each of these cell populations is useful in the below described methods for reducing one or more symptoms of cardiac muscle cell necrosis and/or sterile inflammation in a tissue.

The terms "purified," "isolated," and grammatical equivalents thereof as used herein, refer to the reduction in the amount of at least one undesirable component (such as cell type, protein, and/or nucleic acid sequence) from a sample, including a reduction by any numerical percentage of from 5% to 100%, such as, but not limited to, from 10% to 100%, from 20% to 100%, from 30% to 100%, from 40% to 100%, from 50% to 100%, from 60% to 100%, from 70% to 100%, from 80% to 100%, and from 90% to 100%. Thus purification results in an "enrichment," i.e., an increase in the amount of a desirable cell type, protein and/or nucleic acid sequence in the sample. For example, mesenchymal stem cells (MSCs) may be purified from bone marrow cells using methods known in the art (Wakitani et al., 1995; Fukuda and Yuasa, 2006; Woodbury et al., 2000; Deng et al., 2001; Kim et al., 2006; Mareschi et al., 2006; Krampera et al., 2007). In another example, rapidly self-renewing mesenchymal stem cells (RS-MSCs) may be purified from bone marrow cells and/or from a purified population of mesenchymal stem cells (MSCs) using methods described herein (e.g., binding to one or more of antibody that specifically binds to PODXL, and/or antibody that specifically binds to CD49f).

"Cytokine" is a category of signaling molecule (protein, peptide, glycoprotein) that is involved in cellular communication. "Pro-inflammatory cytokine" refers to a cytokine produced predominantly by activated immune cells, such as microglia, and is involved in the amplification of inflammatory reactions. Pro-inflammatory cytokines are exemplified by IL-1alpha, IL-1beta, IL-6, TNF-alpha, and TGF-beta. Other pro-inflammatory mediators include LIF, IFN-gamma, OSM, CNTF, TGF-beta, GM-CSF, IL11, IL12, IL17, IL18, and IL8.

"Chemokine" and "pro-inflammatory chemokine" interchangeably refer to a molecule that chemoattracts inflammatory cells, and that contains a polypeptide comprising at least two (preferably at least three) cysteine residues that are involved in forming the molecule's 3-dimensional shape. Chemokines include CC chemokines, CXC chemokines, C chemokines, and CX3C chemokines. "CC chemokines" (also referred to as "β-chemokines") have two adjacent cysteines near their amino terminus, and include those that have four cysteines (C4-CC chemokines), and six cysteines (C6-CC chemokines). CC-chemokine are exemplified by RANTES, AOP-RANTES, CAP-RANTES, HEY-Gly$^1$-RANTES, HEA-Gly$^1$-RANTES, NNY-RANTES, NNA-RANTES, DDY-RANTES, PSC-RANTES, P1-RANTES, P2-RANTES, C1,C5-RANTES, L-RANTES, Met-RANTES, MIP-1α, MIP-1αP, AOP-MIP-1α, MIP-1β, vMIP-II. In "CXC chemokines" (also referred to as "α-chemokines") the two N-terminal cysteines are separated by one amino acid ("X"). CXC chemokines include chmokines with the motif glutamic acid-Leucine-Arginine (ELR) immediately before the first cysteine of the CXC motif (ELR-positive) (exemplified by CXCL1, CXCL2, CXCL3, CXCL5, CXCL6, CXCL8), and those without an ELR motif (ELR-negative). Chemokines with an ELR sequence motif have been found to chemoattract and activate primarily neutrophils. Chemokines without the ELR sequence motif appear to chemoattract and activate monocytes, dendritic cells, T-cells, NK-cells, B-lymphocytes, basophils, and eosinophils. "C chemokines" (also known as "γ chemokines") have only two cysteines; one N-terminal cysteine and one cysteine downstream. "$CX_3C$ chemokines" (also known as "δ-chemokines") have three amino acids between the two cysteines.

The inventors have demonstrated that isolated preparations of RS-MSCs are far more clonogenic and have greater potential to differentiate in culture than more mature MSCs from more confluent cultures that the inventors have defined as "SM-MSCs" (Smith et al., 2004) and that are currently employed by most investigators. The inventors have demonstrated that the sub-population of MSCs obtained by serum-starvation of cultures (pre-RS-MSCs) are very early progenitor cells with enhanced expression of Oct-4 and other embryonic genes (Pochampally et al., 2004). The inventors have defined Dkk-1 derived synthetic peptides that inhibit Wnt signaling and therefore provide a means of recovery and manipulation in culture of early precursor sub-populations of MSCs (Gregory et al., 2005). The inventors have established that the sub-population of MSCs defined as RS-MSCs are engrafted preferentially after IV infusion into immunodeficient mice, and that they migrate more efficiently to cytokines that attract stem cells because of their expression of CXCR4 and CX3R1, the receptors for SDF-1 and fractalkine (Lee et al., 2006).

The inventors used ex vivo co-culture experiments to demonstrate that both cell fusion and differentiation without evidence of cell fusion occurred when MSCs were co-cultured with heat-shocked pulmonary epithelial cells or cardiac endothelial cells (Spees et al., 2003). The inventors used ex vivo co-culture experiments to demonstrate the surprising finding that MSCs could rescue cells with non-functional mitochondria by transfer of either intact mitochondria or mitochondrial DNA (Spees et al., 2003). The inventors used experiments with chick embryos to demonstrate that rat MSCs can differentiate into early cardiomyocytes without evidence of cell fusion (Pochampally et al., 2004).

Friedenstein et al. (Owen and Friedenstein, 1998) originally identified MSCs by their ready adherence to tissue culture surfaces, an isolation technique subsequently followed by most investigators. Numerous attempts were made to develop more specific procedures for isolation and characterization of the cells by preparing antibodies to surface epitopes on MSCs (see Simmons and Torok-Storb, 1991; Haynesworth et al., 1992; Gronthos et al., 2003; Anjos-Afonso Bonnet 2007; Gang et al., 2007; Battula et al., 2007; Martinez et al., 2007). Although the published antibodies to MSCs are useful, none distinguish two major sub-populations that are present in early-passage human MSCs plated at low density: (a) spindle-shaped and rapidly self-renewing cells referred to as type I cells (Mets and Verdunk, 1982) or "RS-MSCs" (Colter et al., 2002), and (b) larger, slowly replicating type II cells or "SR-MSCs" that arise from type I or RS-MSCs as the cultures expand to confluency.

Thus, in one embodiment, the invention provides a purified population of rapidly self-renewing mesenchymal stem cells (RS-MSCs) that has been contacted with one or more of ligands, such as TNF-alpha, IL1, and LPS under conditions to express increased levels of TSG-6 protein. These cells are useful in the below described methods for reducing one or more symptoms of cardiac muscle cell necrosis and/or sterile inflammation in a tissue.

D. Transgenic Mesenchymal Stem Cells (MSCs), and/or Transgenic Rapidly Self-Renewing Mesenchymal Stem Cells (RS-MSCs), that Over-Express TSG-6 Protein In a further embodiment, the invention provides a population of transgenic mesenchymal stem cells (MSCs) that (a) comprises a heterologous nucleotide sequence encoding TSG-6 protein, and (b) expresses the TSG-6 protein. In a particular embodiment, the population of transgenic mesenchymal stem cells (MSCs) is purified. In a further embodiment, the population of transgenic mesenchymal stem cells (MSCs) comprises transgenic rapidly self-renewing mesenchymal stem cells (RS-MSCs) that (a) comprise a heterologous nucleotide sequence encoding TSG-6 protein, and (b) express the TSG-6 protein. Each of these cell populations is useful in the below described methods for reducing one or more symptoms of cardiac muscle cell necrosis and/or sterile inflammation in a tissue.

The invention also provides a population of transgenic rapidly self-renewing mesenchymal stem cells (RS-MSCs) that (a) comprises a heterologous nucleotide sequence encoding TSG-6 protein, and (b) expresses the TSG-6 protein. These cells are useful in the below described methods for reducing one or more symptoms of cardiac muscle cell necrosis and/or sterile inflammation in a tissue.

The term "transgenic" when used in reference to a cell refers to a cell which contains a transgene, or whose genome has been altered by the introduction of a "transgene." Transgenic cells may be produced by several methods including the introduction of a "transgene" comprising nucleic acid (usually DNA) into a target cell or integration of the transgene into a chromosome of a target cell by way of human intervention, using methods known in the art such as vectors (e.g., plasmids, linear DNA, encapsidated virus, etc.)

The term "transgene" as used herein refers to any nucleic acid sequence that is introduced into the cell by experimental manipulations. A transgene may be an "endogenous DNA sequence" or a "heterologous DNA sequence." The term "endogenous DNA sequence" refers to a nucleotide sequence that is naturally found in the cell into which it is introduced so long as it does not contain some modification (e.g., a point mutation, the presence of a selectable marker gene, etc.) relative to the naturally occurring sequence. The terms "heterologous DNA sequence" and "foreign DNA sequence" interchangeably refer to a nucleotide sequence that is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence that contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

Vectors (i.e., plasmids, linear DNA, encapsidated virus, etc.) may be introduced into cells using techniques well known in the art. The term "introducing" a nucleic acid sequence into a cell refers to the introduction of the nucleic acid sequence into a target cell to produce a "transformed" or "transgenic" cell. Methods of introducing nucleic acid sequences into cells are well known in the art. For example, where the nucleic acid sequence is a plasmid or naked piece of linear DNA, the sequence may be "transfected" into the cell using, for example, calcium phosphate-DNA co-precipitation, DEAE-dextran-mediated transfection, polybrene-mediated transfection, electroporation, microinjection, liposome fusion, lipofection, protoplast fusion, and biolistics. Alternatively, where the nucleic acid sequence is encapsidated into a viral particle, the sequence may be introduced into a cell by "infecting" the cell with the virus.

Transformation of a cell may be stable or transient. The terms "transient transformation" and "transiently transformed" refer to the introduction of one or more nucleotide sequences of interest into a cell in the absence of integration of the nucleotide sequence of interest into the host cell's genome. Transient transformation may be detected by, for example, enzyme-linked immunosorbent assay (ELISA) that detects the presence of a polypeptide encoded by one or more of the nucleotide sequences of interest. Alternatively, transient transformation may be detected by detecting the activity of the protein encoded by the nucleotide sequence of interest. The term "transient transformant" refer to a cell that has transiently incorporated one or more nucleotide sequences of interest.

In contrast, the terms "stable transformation" and "stably transformed" refer to the introduction and integration of one or more nucleotide sequence of interest into the genome of a cell. Thus, a "stable transformant" is distinguished from a transient transformant in that, whereas genomic DNA from the stable transformant contains one or more heterologous nucleotide sequences of interest, genomic DNA from the transient transformant does not contain the heterologous nucleotide sequence of interest. Stable transformation of a cell may be detected by Southern blot hybridization of genomic DNA of the cell with nucleic acid sequences that are capable of binding to one or more of the nucleotide sequences of interest. Alternatively, stable transformation of a cell may also be detected by the polymerase chain reaction of genomic DNA of the cell to amplify the nucleotide sequence of interest.

"Gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

E. Pharmaceutical Compositions

The invention additionally provides a pharmaceutical composition comprising the purified MSCs, and/or purified RS-MSCs, and/or transgenic MSCs that express TSG-6, and/or transgenic RS-MSCs that express TSG-6, and/or purified TSG-6.

The terms "pharmaceutical" and "physiologically tolerable" composition interchangeably refer to a composition that contains pharmaceutically acceptable molecules, i.e., molecules that are capable of administration to or upon a subject and that do not substantially produce an undesirable effect such as, for example, adverse or allergic reactions, dizziness, gastric upset, toxicity and the like, when administered to a subject. Preferably also, the pharmaceutically acceptable molecule does not substantially reduce the activity of the invention's compositions. Pharmaceutical molecules include, but are not limited to, excipients and diluents.

An "excipient" is an inactive substance used as a carrier for the invention's compositions that may be useful for delivery, absorption, bulking up to allow for convenient and accurate dosage of the invention's compositions. Excipients include, without limitation, antiadherents, binders (e.g., starches, sugars, cellulose, modified cellulose such as hydroxyethyl cellulose, hydroxypropyl cellulose and methyl cellulose, lactose, sugar alcohols such as xylitol, sorbital and maltitol, gelatin, polyvinyl pyrrolidone, polyethylene glycol), coatings (e.g., shellac, corn protein zein, polysaccharides), disintegrants (e.g., starch, cellulose, crosslinked polyvinyl pyrrolidone, sodium starch glycolate, sodium carboxymethyl cellulosemethylcellulose), fillers (e.g., cellulose, gelatin, calcium phosphate, vegetable fats and oils, and sugars, such as lactose), diluents, flavors, colors, glidants (e.g., silicon dioxide, talc), lubricants (e.g., talc, silica, fats, stearin, magnesium stearate, stearic acid), preservatives (e.g., antioxidants such as vitamins A, E, C, selenium, cystein, methionine, citric acids, sodium citrate, methyl paraben, propyl paraben), sorbents, sweetners (e.g., syrup). In a particular embodiment, the excipient comprises HEC (hydroxyethylcellulose), which is a nonionic, water-soluble polymer that can thicken, suspend, bind, emulsify, form films, stabilize, disperse, retain water, and provide protective colloid action.

Exemplary "diluents" include water, saline solution, human serum albumin, oils, polyethylene glycols, aqueous dextrose, glycerin, propylene glycol or other synthetic solvents.

F. Methods for Purifying RS-MSCs

The invention provides a method for purifying rapidly self-renewing mesenchymal stem cells (RS-MSCs), comprising a) providing a first population of cells comprising RS-MSCs, b) contacting the population of cells with one or both of (i) an antibody that specifically binds to PODXL and (ii) an antibody that specifically binds to CD49f, and c) isolating cells that bind to the one or both of the antibodies, thereby producing a population of purified RS-MSCs.

For example, FIG. 3. shows the changes in the epitopes in MSCs with expansion in culture, and that cell populations enriched for $PODXL^{hi}/CD49F^{hi}$ cells demonstrate increased clonogenicity and differentiation potential compared to the MSC cells population from which they are isolated.

The term "antibody" encompasses any immunoglobulin (e.g., IgG, IgM, IgA, IgE, IgD, etc.) obtained from any source (e.g., humans, rodents, non-human primates, caprines, bovines, equines, ovines, etc.). Included within this definition are polyclonal antibody, monoclonal antibody, and chimeric antibody. Methods for making monoclonal antibodies are known (See e.g., Harlow and Lane, Antibodies: A Laboratory Manual, Cold Spring Harbor Laboratory Press, Cold Spring Harbor, N.Y.; Köhler and Milstein, Nature, 256:495-497 (1975); PCT/US90/02545, Kozbor et al., Immunol. Today, 4:72 (1983), Cole et al., in Monoclonal Antibodies and Cancer Therapy, Alan R. Liss, Inc., pp. 77-96 (1985). Methods for making a "chimeric antibody" that contains portions of two different antibodies, typically of two different species are also standard in the art. See, e.g.: U.S. Pat. No. 4,816,567 to Cabilly et al.; U.S. Pat. No. 4,978,745 to Shoemaker et al.; U.S. Pat. No. 4,975,369 to Beavers et al.; and U.S. Pat. No. 4,816,397 to Boss et al.

The terms "specific binding," "binding specificity," and grammatical equivalents thereof when made in reference to the binding of a first molecule (such as a polypeptide, glycoprotein, nucleic acid sequence, etc.) to a second molecule (such as a polypeptide, glycoprotein, nucleic acid sequence, etc.) refer to the preferential interaction between the first molecule with the second molecule as compared to the interaction between the second molecule with a third molecule. Specific binding is a relative term that does not require absolute specificity of binding; in other words, the term "specific binding" does not require that the second molecule interact with the first molecule in the absence of an interaction between the second molecule and the third molecule. Rather, it is sufficient that the level of interaction between the first molecule and the second molecule is higher than the level of interaction between the second molecule with the third molecule. "Specific binding" of a first molecule with a second molecule also means that the interaction between the first molecule and the second molecule is dependent upon the presence of a particular structure on or within the first molecule. For example, if a second molecule is specific for structure "A" that is on or within a first molecule, the presence of a third nucleic acid sequence containing structure A will reduce the amount of the second molecule which is bound to the first molecule.

Antibodies that specifically bind to PODXL are known in the art, including FITC Labeled anti-Human PCLP1 (Cat. #M084-4, MBL International Corporation, Woburn, Mass.). Antibodies that specifically bind to CD49f are known in the art including PE-Cy5 Rat anti-Human CD49f (Cat. #551129, BD PharMingen/BD Biosciences.

Figure 8:
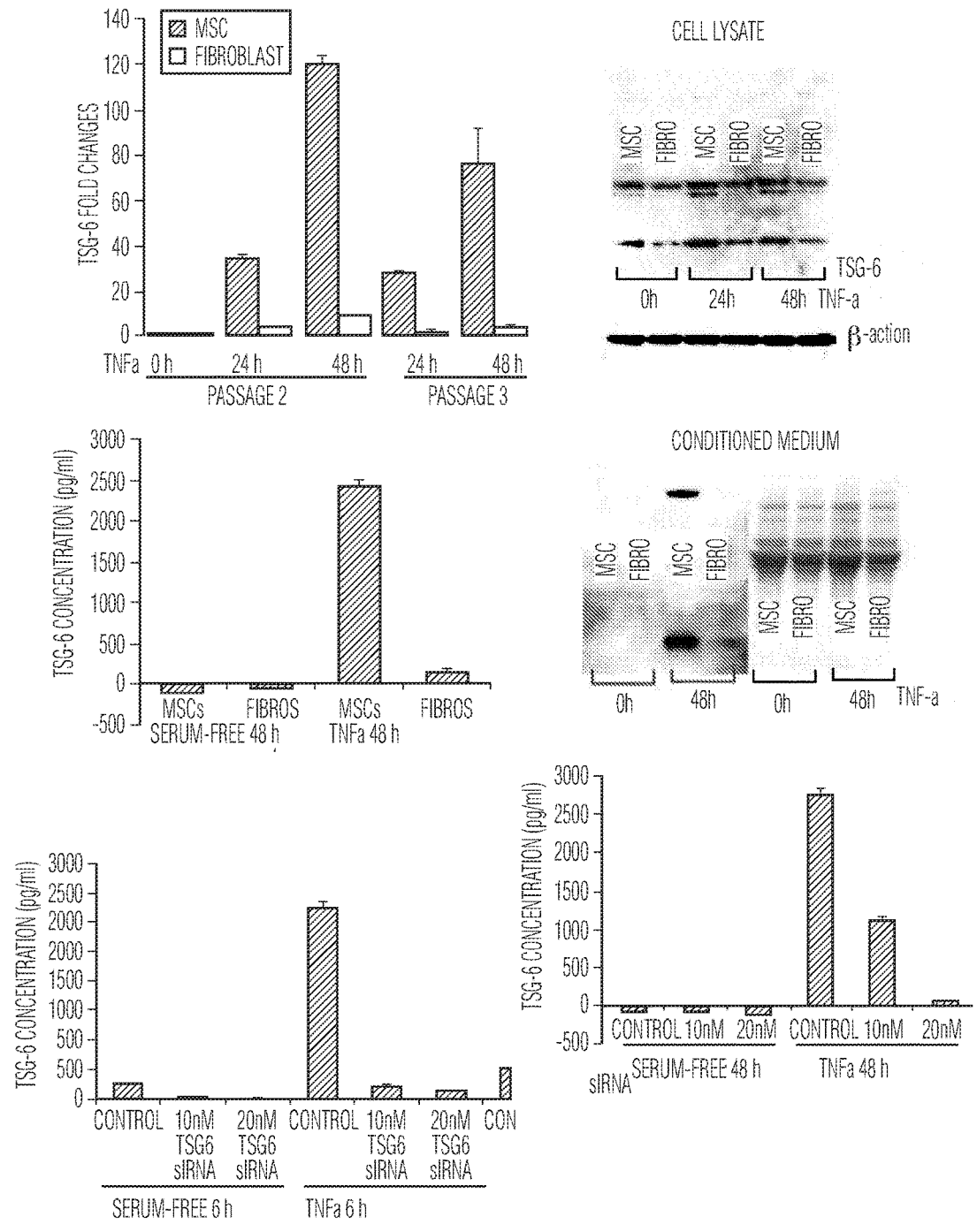
FIG. 8 shows expression of TSG-6.

In a particular embodiment, the methods further include step d) contacting the population of purified RS-MSCs with one or more of TNF-alpha, IL1, and LPS under conditions to produce a contacted population of cells that expresses increased levels of TSG-6 protein compared to TSG-6 protein levels expressed by the population of purified RS-MSCs. In a more preferred embodiment, the increased levels of TSG-6 protein are from 10 fold to 500 fold. In yet a further embodiment, the increased levels of TSG-6 protein is higher by any numerical amount from 5 fold to 1000 fold, including from 5 fold to 500 fold, 10 fold to 400 fold, from 20 fold to 300 fold, from 30 fold to 200 fold, from 40 fold to 200 fold, from 50 fold to 200 fold. For example, FIG. 8 shows increased expression of 60-fold to 120-fold.

In an alternative embodiment, the methods comprise step d) transfecting the population of purified RS-MSCs with a nucleotide sequence that encodes TSG-6 protein (e.g., sequences of FIG. 19).

The invention further contemplates a purified population of rapidly self-renewing mesenchymal stem cells (RS-MSCs) produced by the methods described herein.

G. Methods for Treating Cardiac Muscle Damage by Administering Preactivated MSCs and/or Preactivated RS-MSCs In a particular embodiment, the invention provides a method for reducing one or more symptoms of cardiac muscle cell necrosis in a mammalian subject comprising a) providing i) a mammalian subject in need of reducing one or more symptoms of cardiac muscle cell necrosis, and ii) a population of purified mesenchymal stem cells (MSCs) that has been contacted with one or more of TNF-alpha, IL1, and LPS under conditions to express increased levels of TSG-6 protein, and b) administering a therapeutically effective amount of the population of purified mesenchymal stem cells (MSCs) to the mammalian subject, thereby reducing one or more symptoms of the cardiac muscle cell necrosis. In a particular embodiment, the population of purified mesenchymal stem cells (MSCs) comprises purified rapidly self-renewing mesenchymal stem cells (RS-MSCs).

"Subject" "and "animal" interchangeably refer to any multicellular animal, preferably a mammal, e.g., humans, non-human primates, murines, ovines, bovines, ruminants, lagomorphs, porcines, caprines, equines, canines, felines, ayes, etc.). Thus, mammalian subjects include mouse, rat, guinea pig, hamster, ferret and chinchilla.

"Subject in need of" reducing one or more symptoms of a disease, e.g., cardiac muscle cell necrosis, inflammation, etc., includes a subject that exhibits and/or is at risk of exhibiting one or more symptoms of the disease. For Example, subjects may be at risk based on family history, genetic factors, environmental factors, etc. This term includes animal models of the disease, such as the mouse models described herein.

As used herein the terms "therapeutically effective amount" and "protective amount" of a composition (e.g., cells, nucleotide sequence, protein sequences, etc.) with respect to cardiac muscle cell necrosis and/or myocardial infarction, interchangeably refer to, in one embodiment, an amount of the composition that delays, reduces, palliates, ameliorates, stabilizes, prevents and/or reverses one or more symptoms of the disease compared to in the absence of the composition of interest. It is not necessary that all symptoms be completely eliminated. The term "delaying" symptoms refers to increasing the time period during which symptoms are detectable. The term "eliminating" symptoms refers to 100% reduction of one or more symptoms. A pharmaceutically effective amount may be determined using in vitro and in vivo assays known in the art and disclosed herein, as well as clinical trials. The amount depends, for example, on the route of administration, patient weight (e.g. milligrams of drug per kg body weight). These factors and their relationship to determining this amount are well known to skilled practitioners in the medical, veterinary, and other related arts. This amount and the method of administration can be tailored to achieve optimal efficacy but will depend on such factors as weight, diet, concurrent medication and other factors that those skilled in the art will recognize. The dosage amount and frequency are selected to create an effective level of the composition without substantially harmful effects. When administered orally or intravenously, the dosage of the polypeptides will generally range from 0.001 to 1000 mg/Kg/day, more preferably from 0.01 to 100 mg/Kg/day, and most preferably from 0.1 to 10 mg/Kg/day.

"Symptoms of myocardial muscle cell necrosis" and "symptoms of cardiac infarction" are used to refer to objective and/or subjective symptoms. Objective symptoms are exemplified by increased plasmin activity in serum (FIG. 9A), increased cardiac tissue levels of one or more of plasminogen activator (tPA), urokinase (uPA), pro-matrix metalloproteinase 9 (pro-MMP9), active MMP9 (FIGS. 9B and 9C), and cardiac muscle cell death. Symptoms may also include subjective symptoms such as chest pain, shortness of breath, nausea, vomiting, palpitations, sweating, anxiety, feeling of indigestion, fatigue, etc.

"Necrosis" refers to the premature death of cells and living tissue. Necrosis is typically caused by external factors, such as infection, toxins, trauma, reduced blood supply, etc. This is in contrast to apoptosis, which is a naturally occurring cause of cellular death.

The term "administering" refers to introducing a polypeptide, introducing a nucleic acid sequence encoding a polypeptide, and/or introducing a host cell that expresses a polypeptide. Polypeptides may be administered to a subject using methods known in the art (e.g., Erickson et al., U.S. Pat. No. 6,632,979; Furuta et al., U.S. Pat. No. 6,905,839; Jackobsen et al., U.S. Pat. No. 6,238,878; Simon et al., U.S. Pat. No. 5,851,789), including those for administering bacteria (Bellinger et al., U.S. Pat. No. 6,964,856) and for administering antisense (de la Monte et al., U.S. Pat. No. 7,291,454; Smith et al., WO 90/09180; Squinto et al., WO 93/00909), and oligonucleotides (Inoyue et al., U.S. Pat. No. 5,272,065). The polypeptides, nucleic acid sequences and/or cells may be administered prophylactically (i.e., before the observation of disease symptoms) and/or therapeutically (i.e., after the observation of disease symptoms). Administration also may be concomitant with (i.e., at the same time as, or during) manifestation of one or more disease symptoms. Also, the invention's compositions may be administered before, concomitantly with, and/or after administration of another type of drug or therapeutic procedure (e.g., surgery). Methods of administering the invention's compositions include, without limitation, administration in parenteral, oral, intraperitoneal, intranasal, topical (e.g., rectal, and vaginal), and sublingual forms. Parenteral routes of administration include, for example, subcutaneous, intravenous, intramuscular, intrasternal injection, and infusion routes.

In a particular embodiment, the route of administration is selected from the group consisting of intramuscular administration into cardiac muscle and intravenous administration.

H. Methods for Treating Cardiac Muscle Damage by Administering Transgenic MSCs and/or Transgenic RS-MSCs The invention provides a method for reducing one or more symptoms of cardiac muscle cell necrosis in a mammalian subject comprising a) providing i) a mammalian subject in need of reducing one or more symptoms of cardiac muscle cell necrosis, ii) a population of transgenic mesenchymal stem cells (MSCs) that (a) comprises a heterologous nucleotide sequence encoding TSG-6 protein, and (b) expresses the TSG-6 protein, and b) administering a therapeutically effective amount of the population of transgenic mesenchymal stem cells (MSCs) to the mammalian subject, thereby reducing one or more symptoms of the cardiac muscle cell necrosis.

In one embodiment, the population of transgenic mesenchymal stem cells (MSCs) comprises purified rapidly self-renewing mesenchymal stem cells (RS-MSCs).

Without intending to limit the route of administration to any particular route, in one embodiment, the route of administration is selected from the group consisting of intramuscular administration into cardiac muscle and intravenous administration.

I. Methods for Treating Cardiac Muscle Damage by Administering TSG-6 Protein

The invention also provides a method for reducing one or more symptoms of cardiac muscle cell necrosis in a mammalian subject comprising a) providing i) a mammalian subject in need of reducing one or more symptoms of cardiac muscle cell necrosis, and ii) a composition comprising purified tumor necrosis factor-alpha stimulated gene 6 (TSG-6) protein, and b) administering a therapeutically effective amount of the composition to the mammalian subject, thereby reducing one or more symptoms of the cardiac muscle cell necrosis.

Purified recombinant TSG-6 protein, is commercially available (R&D Systems, Inc., Minneapolis, Catalog #2104-TS-050). In another embodiment, TSG-6 protein may be purified from a transgenic cell that (a) comprises a heterologous nucleotide sequence encoding TSG-6 protein, and (b) expresses the TSG-6 protein.

Any cell that may be transformed to express a heterologous nucleotide sequence may be used to express TSG-6 protein. Such cells include human and non-human eukaryotic animal cells. In one embodiment, the cell is a human eukaryotic animal cell as exemplified by U937 cells (macrophage), ATCC #crl 1593.2; A-375 cells (melanoma/melanocyte), ATCC #crl-1619; KLE cells (uterine endometrium), ATCC #crl-1622; T98G cells (glioblastoma), ATCC #crl-1690; CCF-STTG1 cells (astrocytoma), ATCC #crl-1718; HUV-EC-C cells (vascular endothelium), ATCC #CRL-1730; UM-UC-3 cells (bladder), ATCC #crl-1749; CCD841-CoN cells (colon, ATCC #crl-1790; SNU-423 cells (hepatocellular carcinoma), ATCC #crl-2238; WI38 cells (lung, normal), ATCC #crl-75; Raji cells (lymphoblastoid), ATCC #ccl-86; BeWo cells (placenta, choriocarcinoma), ATCC #ccl-98; HT1080 cells (fibrosarcoma), ATCC #ccl-121; MIA PaCa2 cells (pancreas), ATCC #crl-1420; CCD-25SK cells (skin fibroblast), ATCC #crl-1474; ZR75-30 cells (mammary gland), ATCC #crl-1504; HOS cells (bone osteosarcoma), ATCC #crl-1543; 293-SF cells (kidney), ATCC #crl-1573; LL47 (MaDo) cells (normal lymphoblast), ATCC #ccl-135; and HeLa cells (cervical carcinoma), ATCC #ccl-2.

In another embodiment, the cell is a non-human eukaryotic animal cell exemplified by, but not limited to, yeast cells (AH109), LM cells (mouse fibroblast), ATCC #ccl-1.2; NCTC 3526 cells (rhesus monkey kidney), ATCC #ccl-7.2; BHK-21 cells (golden hamster kidney), ATCC #ccl-10; MDBK cells (bovine kidney), ATCC #ccl-22; PK 15 cells (pig kidney), ATCC #ccl-33; MDCK cells (dog kidney), ATCC #ccl-34; PtK1 cells (kangaroo rat kidney), ATCC #ccl-35; Rk 13 cells (rabbit kidney), ATCC #ccl-37; Dede cells (Chinese hamster lung fibroblast), ATCC #ccl-39; Bu (IMR31) cells (bison lung fibroblast), ATCC #ccl-40; FHM cells (minnow epithelial), ATCC #ccl-42; LC-540 cells (rat Leydig cell tumor), ATCC #ccl-43; TH-1 cells (turtle heart epithelial), ATCC #ccl-50; E. Derm (NBL-6) cells (horse fibroblast), ATCC #ccl-57; MvLn cells (mink epithelial), ATCC #ccl-64; Ch1 Es cells (goat fibroblast), ATCC #ccl-73; P1 I Nt cells (raccoon fibroblast), ATCC #ccl-74; Sp I k cells (dolphin epithelial), ATCC #ccl-78; CRFK cells (cat epithelial), ATCC #ccl-94; Gekko Lung 1 cells (lizard-gekko epithelial), ATCC #ccl-111; Aedes Aegypti cells (mosquito epithelial), ATCC #ccl-125; ICR 134 cells (frog epithelial), ATCC #ccl-128; Duck embryo cells (duck fibroblast), ATCC #ccl-141; DBS Fcl-1 cells (monkey lung fibroblast), ATCC #ccl-161.

J. Methods for Treating Sterile Inflammation Using Preactivated MSCs and/or Preactivated RS-MSCs The invention also provides a method for reducing one or more symptoms of inflammation, including, but not limited to, sterile inflammation in a mammalian subject comprising a) providing i) a mammalian subject in need of reducing one or more symptoms of sterile inflammation in a tissue, and ii) a population of purified mesenchymal stem cells (MSCs) that has been contacted with one or more of TNF-alpha, IL1, and LPS under conditions to express increased levels of TSG-6 protein, and b) administering a therapeutically effective amount of the population of purified mesenchymal stem cells (MSCs) to the mammalian subject, thereby reducing one or more symptoms of the sterile inflammation in the tissue. In one embodiment, the population of purified mesenchymal stem cells (MSCs) comprises purified rapidly self-renewing mesenchymal stem cells (RS-MSCs). In another embodiment, the subject has, or is at risk of having, a sterile inflammatory disease. Inflammation can also be due to an autoimmune response.

"Inflammation" "inflammatory" and grammatical equivalents when in reference to a disease refer to the complex biological response of vascular tissues to harmful stimuli, such as pathogens, damaged cells, or irritants. It is a protective attempt by the organism to remove the injurious stimuli as well as initiate the healing process for the tissue.

Inflammation can be acute or chronic. Acute inflammation is the initial response of the body to harmful stimuli and is achieved by the increased movement of plasma and leukocytes from the blood into the injured tissues. A cascade of biochemical events propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

Inflammation is not a synonym for infection by a pathogen. Thus, "sterile inflammation" refers to inflammation that is not caused by a pathogen (e.g., bacteria, virus, etc.), but which is caused in response to an injury or abnormal stimulation caused by a physical, chemical, or biologic molecule (protein, DNA, etc.); these reactions include the local reactions and resulting morphologic changes, destruction or removal of the injurious material, and responses that lead to repair and healing. One underlying theme in inflammatory disease is a perturbation of the cellular immune response that results in recognition of proteins, such as host proteins (antigens), as foreign. Thus the inflammatory response becomes misdirected at host tissues with effector cells targeting specific organs or tissues often resulting in irreversible damage. The self-recognition aspect of autoimmune disease is often reflected by the clonal expansion of T-cell subsets characterized by a particular T-cell receptor (TCR) subtype in the disease state. Often, inflammatory disease is also characterized by an imbalance in the levels of T-helper (Th) subsets (i.e., Th1 cells versus Th2 cells).

Sterile inflammatory disease and conditions may be systemic (e.g., lupus) or localized to particular tissues or organs.

Examples of sterile inflammatory diseases include, without limitation, myocardial infarction (MI), diabetes, stroke, Alzheimer's disease, multiple sclerosis, parkinsonism, nephritis, cancer, inflammatory diseases involving acute or chronic inflammation of bone and/or cartilage in a joint, anaphylactic reaction, asthma, conjunctivitis, systemic lupus erythematosus, pulmonary sarcoidosis, ocular inflammation, allergy, emphysema, ischemia-reperfusion injury, fibromyalagia, and inflammatory cutaneous disease selected from psoriasis and dermatitis, or an arthritis selected from rheumatoid arthritis, gouty arthritis, juvenile rheumatoid arthritis, and osteoarthritis.

"Symptoms of inflammation" and "symptoms of sterile inflammation" are interchangeably used to refers to objective and/or subjective symptoms. Objective symptoms are exemplified by increased serum levels of one or more (including two, three, four, five, six, and seven) of plasmin activity (Example 11, FIGS. 9 and 16), macrophage chemoattractant protein-1 (MCP-1), macrophage inflammatory protein-1 alpha (MIP-1alpha), beta thromboglobulin, soluble ST2 receptor, C-reactive protein (CRP), and natri- uretic peptide compared to a control mammalian subject lacking inflammation in the tissue. Subjective symptoms include pain.

In one embodiment, where inflammation is in cardiac muscle tissue, the route of administration is selected from the group consisting of intramuscular administration into cardiac muscle and intravenous administration.

K. Methods for Treating Sterile Inflammation Using Transgenic MSCs and/or Transgenic RS-MSCs The invention also provides a method for reducing one or more symptoms of sterile inflammation in a mammalian subject comprising a) providing i) a mammalian subject in need of reducing one or more symptoms of sterile inflammation in a tissue, ii) a population of transgenic mesenchymal stem cells (MSCs) that (a) comprises a heterologous nucleotide sequence encoding TSG-6 protein, and (b) expresses the TSG-6 protein, and b) administering a therapeutically effective amount of the population of transgenic mesenchymal stem cells (MSCs) to the mammalian subject, thereby reducing one or more symptoms of the sterile inflammation in the tissue.

In one embodiment, the population of transgenic mesenchymal stem cells (MSCs) comprises purified rapidly self-renewing mesenchymal stem cells (RS-MSCs). In another embodiment, the tissue comprises cardiac muscle tissue and the route of administration is selected from the group consisting of intramuscular administration into the cardiac muscle tissue and intravenous administration. In a further embodiment, the subject has, or is at risk of having, a sterile inflammatory disease.

L. Methods for Treating Sterile Inflammation by Administering TSG-6 Protein

The invention further provides a method for reducing one or more symptoms of sterile inflammation in a mammalian subject comprising a) providing i) a mammalian subject in need of reducing one or more symptoms of sterile inflammation in a tissue, and ii) a composition comprising purified tumor necrosis factor-alpha stimulated gene 6 (TSG-6) protein, and b) administering a therapeutically effective amount of the composition to the mammalian subject, thereby reducing one or more symptoms of the sterile inflammation in the tissue.

In another embodiment, the tissue comprises cardiac muscle tissue and the route of administration is selected from the group consisting of intramuscular administration into the cardiac muscle tissue and intravenous administration. In a further embodiment, the subject has, or is at risk of having, a sterile inflammatory disease. In a further embodiment, the TSG-6 protein is purified from a transgenic cell that comprises a heterologous nucleotide sequence encoding TSG-6 protein, and that expresses the TSG-6 protein.

M. Methods for Detecting Inflammation Using Biomarkers

The invention additionally provides methods for detecting sterile inflammation in a tissue in a mammalian subject comprising a) providing a mammalian subject in need of reducing one or more symptoms of sterile inflammation in a tissue, and b) detecting an increase in serum level of one or more (including two, three, four, five, six and seven) of plasmin activity, macrophage chemoattractant protein-1 (MCP-1), macrophage inflammatory protein-1 alpha (MIP-1alpha), beta thromboglobulin, soluble ST2 receptor, C-reactive protein (CRP), and natriuretic peptide compared to a control mammalian subject lacking the sterile inflammation in the tissue. In one embodiment, the tissue comprises cardiac muscle tissue.

The levels of the biomarkers used in the invention's methods may be determined using standard techniques. For example, methods for detection of plasmin activity are described herein (Example 11, FIGS. 9 and 16); MCP-1 and MIP-1alpha may be assayed using a commercial ELISA kit from Leinco Technologies, Inc., St. Louis, Mo.; Beta thromboglobulin may be assayed using the commercial ELISA kit (ASSERACHROM B-TG) from DIAGNOSTICA STAGO, Inc., Parsippany, N.J.; ST2 may be assayed using the commercial ELISA kit from MBL, Woburn, Mass., and CRP may be assayed by Quest Diagnostics. Additional methods for detecting the levels of the biomarkers are known in the art: Macrophage chemoattractant protein-1 (MCP-1) (Aukrust et al. (1998) Circulation 97:1136-1143); macrophage inflammatory protein-1 alpha (MIP-1alpha) (Aukrust et al. (1998)); beta thromboglobulin: (Riza et al. (2004) Coron Artery Dis.; 15:265-8); soluble ST2 receptor (Weinberg et al. (2002) Circulation 106:2961-2966), C-reactive protein (CRP) (Pye et al. (1990) Br Heart J 63:228-230); and natriuretic peptide ((Weinberg et al. (2002).

In a further embodiment, the method further comprises c) administering to the subject a therapeutically effective amount of one or more of i) a composition comprising purified tumor necrosis factor-alpha stimulated gene 6 (TSG-6) protein, ii) a population of purified mesenchymal stem cells (MSCs) of Claim 1, and ii) a population of transgenic mesenchymal stem cells (MSCs) of Claim 4, wherein the administering produces a treated subject, and d) detecting, in the treated subject, a reduction in serum level of two or more of the plasmin activity, MCP-1, MIP-1alpha, beta thromboglobulin, soluble ST2 receptor, CRP, and natriuretic peptide compared to the serum level that is detected in step b).

EXPERIMENTAL

The following examples serve to illustrate certain preferred embodiments and aspects of the present invention and are not to be construed as limiting the scope thereof.

Example 1

Isolation of RS-MSCs Using PODXL and CD49f Epitope Expression

Figure 1B:
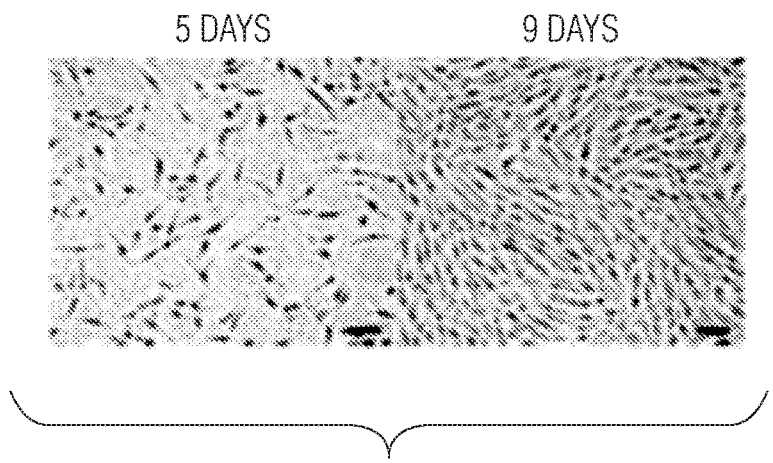
FIG. 1B shows phase-contrast photomicrographs of viable MSCs from Passage 1/donor 1 plated at 100 cells/cm2 and incubated for 5 or 9 days to generate Passage 2 MSCs.
Figure 1C:
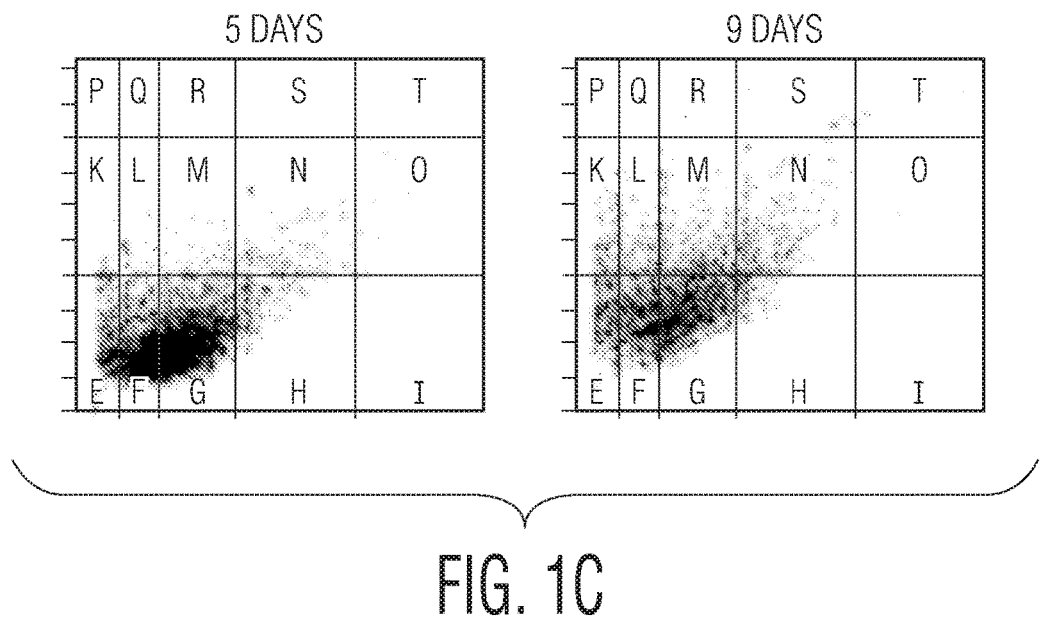
FIG. 1C shows an assay by forward and side scatter of light of MSCs from FIG. 1B. Vertical and horizontal lines were generated with microbeads to standardize the assay. The inventors previously used the assay to distinguish RS-MSCs from SM-MSCs but it was not highly reproducible (Smith et al., 2004).
Figure 1D:
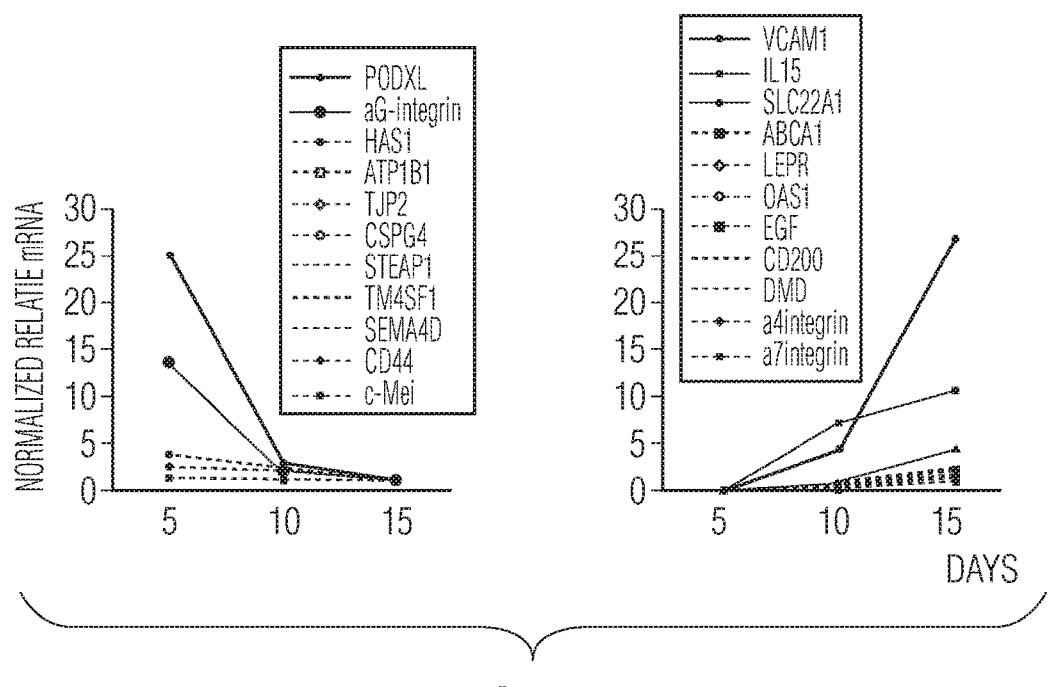
FIG. 1D shows microarray assays of mRNAs from viable hMSCs from Passage 1/donor 6 plated at 100 cells/cm2 and incubated for 5 days to about 50% confluency, 10 days to 100% confluency and 15 days to over-confluency. The values were normalized to mRNA signals on day 15 (left panel) or on day 5 (right panel).
Figure 2A:
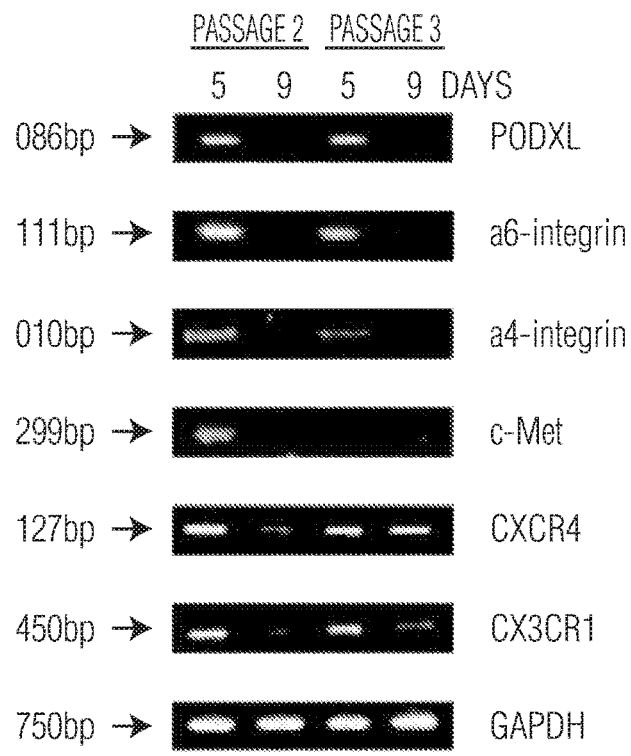
FIG. 2A shows RT-PCR assays.

Recently, the inventors searched for antibodies to surface proteins that identify early progenitors in cultures of MSCs (FIGS. 1A and 1B). As an initial strategy, the inventors queried microarray data for changes in transcripts for surface proteins as hMSCs plated at low density and the cultures expanded. The results demonstrated that the steady-state levels of over 10 transcripts decreased (>2-fold) and an almost equal number increased (FIG. 2D). The two of the transcripts with the largest decreases coded for proteins previously shown to be linked to cell motility and tumor progression: PODXL (Furness and McNagny, 2006); and α6-integrin (CD49f) (Lipscomb and Mercurio 2005).

Figure 2B:
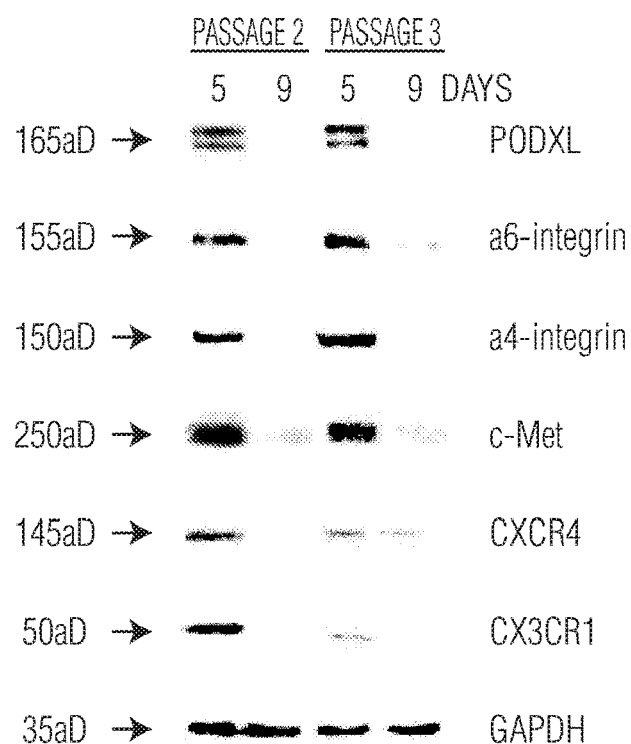
FIG. 2B shows Western blot assays. (C) shows assays by immunocytochemistry. Bar=200 μm. Nuclei were labeled with DAPI (9-day columns, Passages 2 and 3).
Figure 2C:
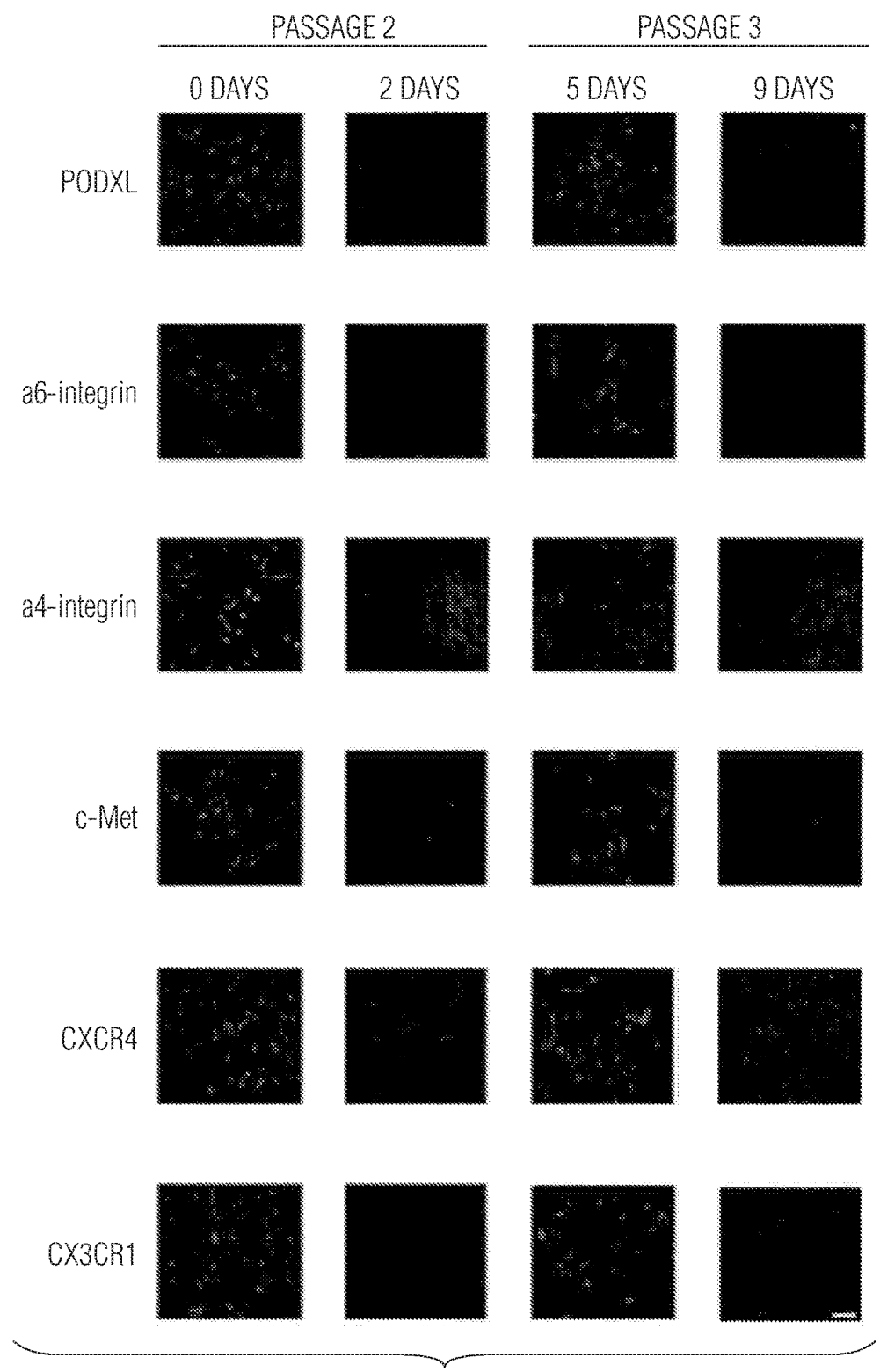
FIG. 2 shows assays of cultures of viable MSCs Passage 1/donor 5 that were plated at 100 cells/cm$^2$ and incubated for 5 days or 9 days to generate Passage 2 MSCs. To prepare Passage 3 MSCs, 9-day cultures were lifted with trypsin/EDTA and re-plated at 100 cells/cm$^2$ for incubation for 5 or 9 days.

The inventors then used commercial antibodies to follow expression of PODXL, α6-integrin (CD49f), and several other epitopes related to cell trafficking and motility as cultures of MSCs were expanded (FIGS. 2 and 3). By the variety of assays indicated, antibodies to PODXL and α6-integrin (CD49f) most consistently distinguished early progenitor RS-MSCs from later stage SR-MSCs. Of special interest was that although the epitopes disappeared as the cultures of Passage 2 cells approached confluency after culture for 9 days, they were again expressed if the cells were re-plated at low density and incubated for 5 days to generate Passage 3 cells. A similar pattern was observed with several other epitopes (α6-integrin, c-Met, CXCR4, and CX3CR1), but these proved less reliable either because they were cleaved and internalized by the trypsinization required to lift the cells from cultures (not shown), or because the results were not as consistent among different preparations of MSCs (FIG. 3). Also of interest was the observation that there was an increase instead of a decrease with expansion of two epitopes previously used to identify MSCs (FIGS. 3D and 3E): STRO-1 (Simmons and Torok-Storb, 1991) and GD2 (Martinez et al., 2007).

To demonstrate the increased clonogenicity and differentiation potential of $PODXL^{hi}/CD49f^{hi}$ MSCs, MSCs were plated at 100 cells/cm². The cultures were expanded for 5 days to obtain MSCs that were $PODXL^{hi}/CD49f^{hi}$ and for 9 days to obtain MSCs that were $PODXL^{lo}/CD49f^{lo}$. Two sub-populations were then re-plated at 1 cell/cm² to assay colony forming units (CFU-Fs). The $PODXL^{hi}/CD49f^{hi}$ cells were more highly clonogenic with CFU-F values of 90%±6.0 SD versus 48%±5 SD for $PODXL^{lo}/CD49f^{lo}$ cells (n=4; p<0.1). In addition, the $PODXL^{hi}/CD49f^{hi}$ cells more efficiently differentiated into mineralizing cells and adipocytes: absorbance of extracted Alizarin Red S after incubation in osteogenic medium 0.16 OD units±0.05 SD versus 0.65±0.029 (n=4; p<0.01) and extracted Oil Red O after incubation in adipogenic medium 0.70 OD units±0.14 SD versus 0.06 OD units±0.012 SD (n=4; p<0.01).

Example 2

More Efficient Engraftment of RS-MSCs into the Hearts of Mice Following MI

Figure 4:
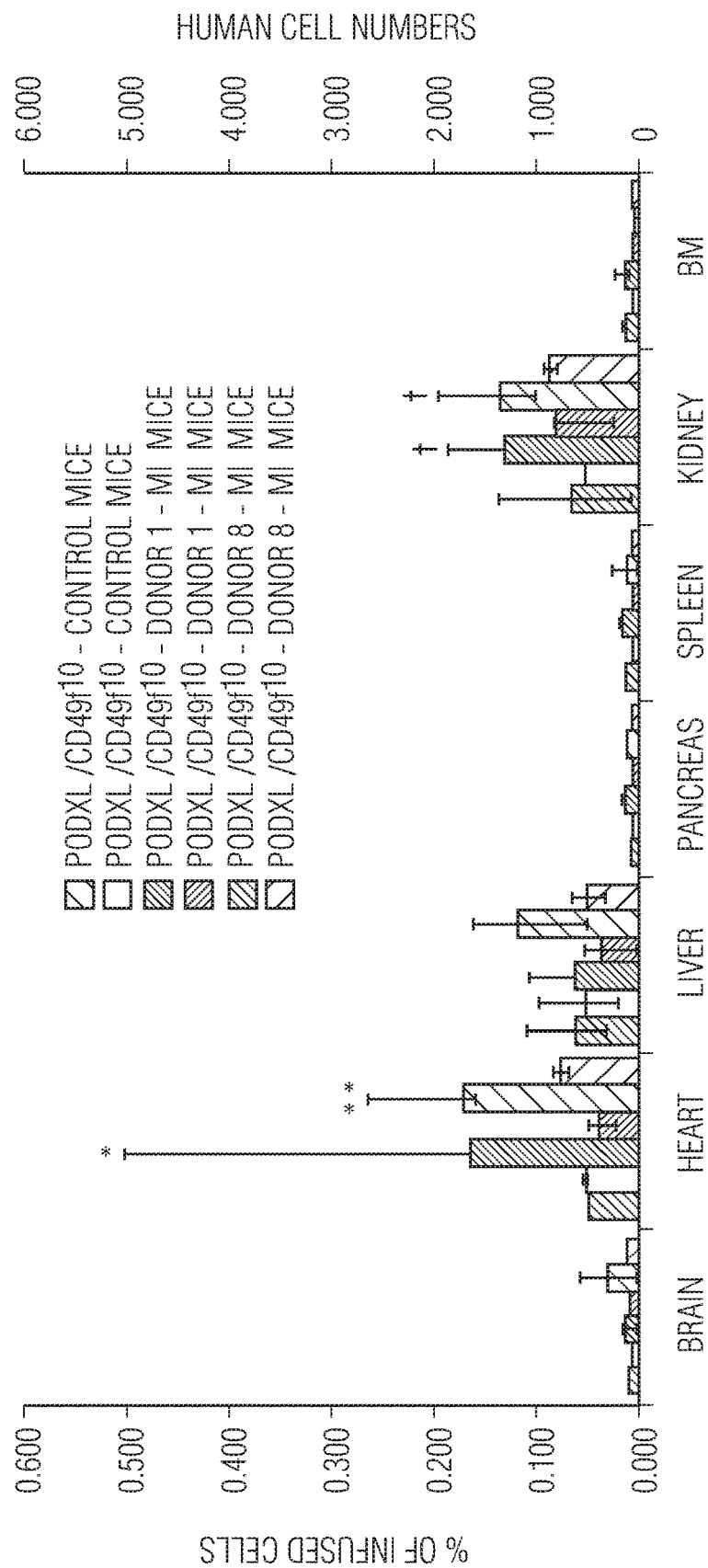
FIG. 4 shows tissue distributions (expressed as % injected cells) of intravenously infused MSCs. One million Passage 2 MSCs (donor 1 and donor 8) that were either PODXL$^{hi}$/CD49f$^{hi}$ or PODXL$^{lo}$/CD49f$^{lo}$ were infused intravenously into control mice or mice with myocardial infarctions (MI). Tissues were recovered one day after the MSC infusions. Values from real-time PCR assays for human Alu sequences are expressed either as % of infused human cells or as human cell numbers. Error bars: range of values; n=4 to 6. Asterisk: $p<0.05$ versus PODXL$^{hi}$/CD49f$^{hi}$ in control mice and $p<0.05$ versus PODXL$^{lo}$/CD49f$^{lo}$ in MI mice by non-parametric Mann-Whitney test; the Kolmogorov-Smirnov test indicated the data were not normally distributed. Double asterisk: $p<0.05$ versus PODXL$^{hi}$/CD49f$^{hi}$ in control mice and $p<0.05$ verse PODXL$^{lo}$/CD49f$^{lo}$ in MI mice by two-tailed Student's t-test. Cross: p<0.05 versus PODXL$^{lo}$/CD49f$^{lo}$ in MI mice by two-tailed Student's t-test.
Figure 5A:
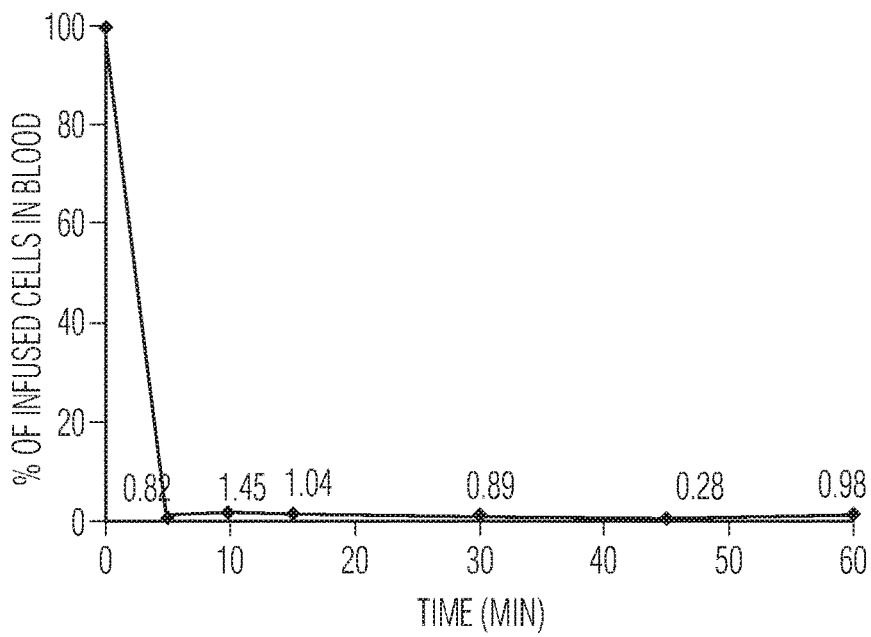
FIG. 5 shows the tissue distribution of infused hMSCs, cancer cells, and human WBCs.
Figure 5B:
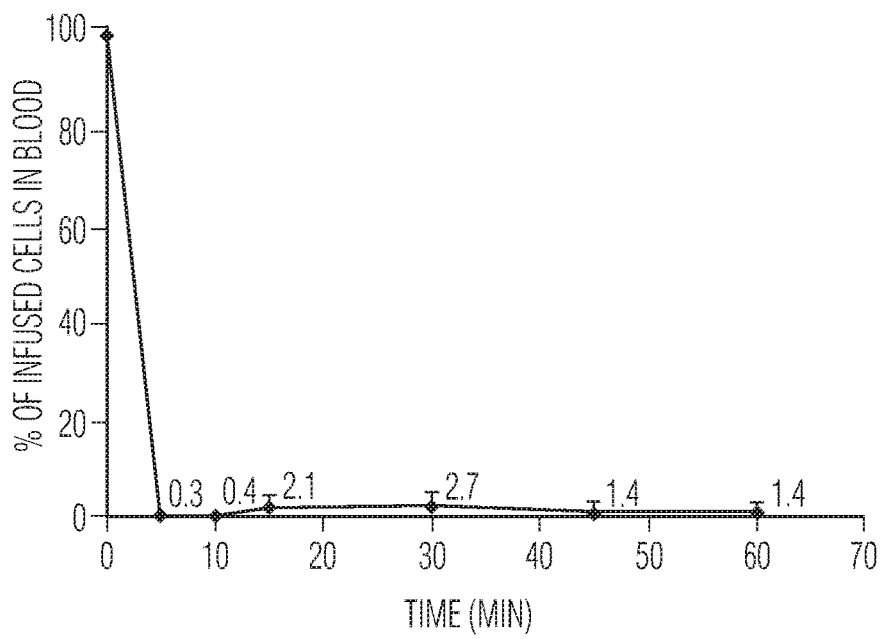
Figure 5C:
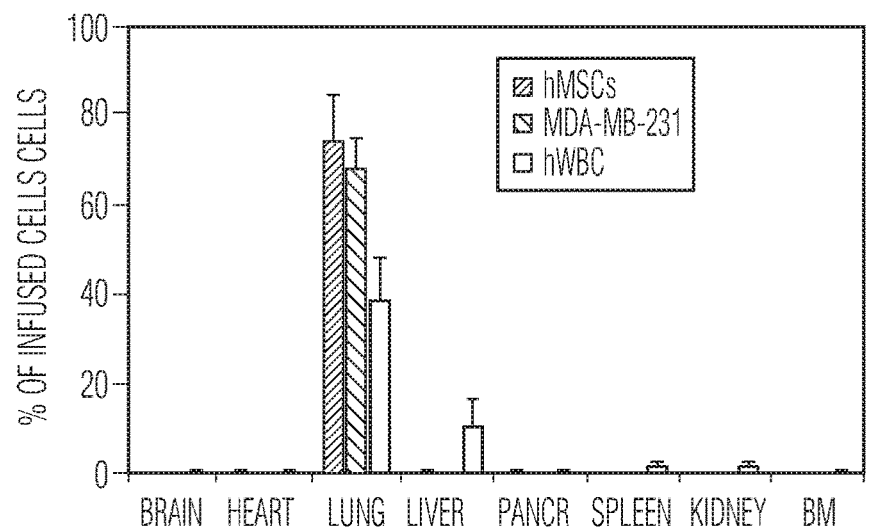
Figure 5D:
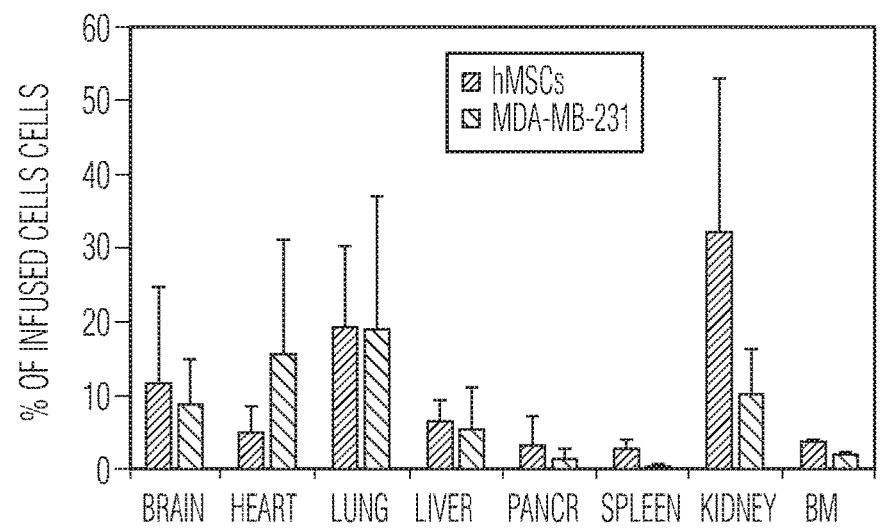
Figure 6A:
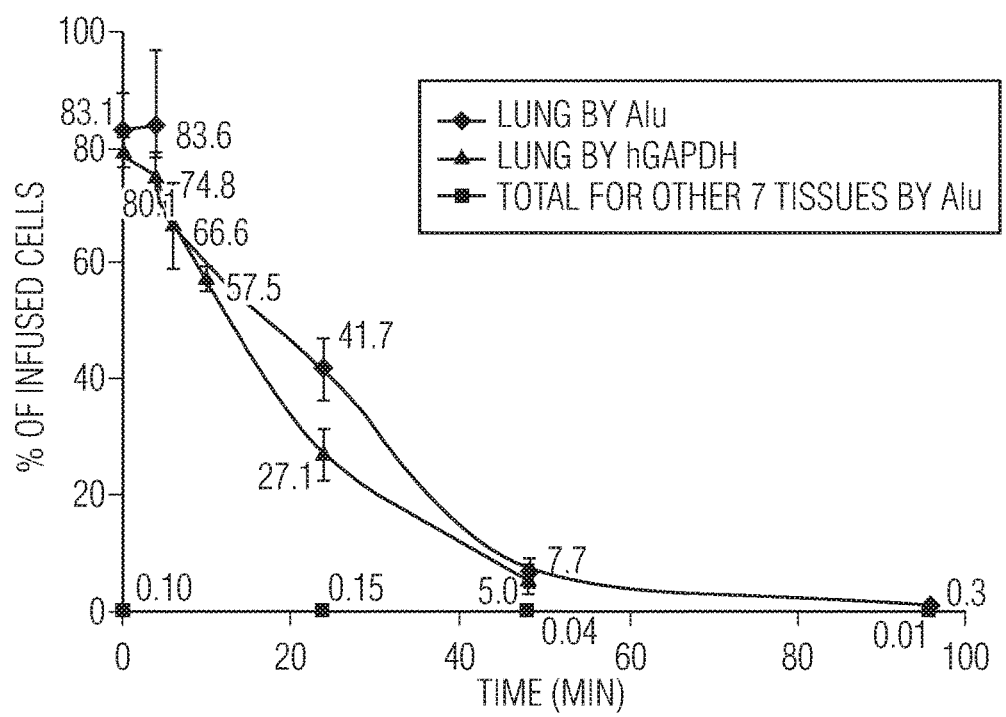
FIG. 6A: Assays for Alu sequences and human mGAPDH demonstrating that over 80% of infused cells are trapped in lung and then gradually disappear over about 50 hr.
Figure 6B:
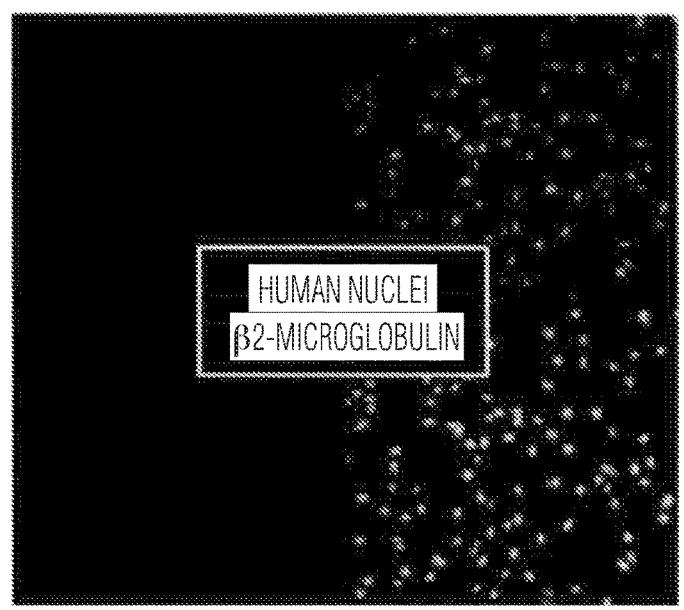
FIG. 6B: Immunohistochemistry results demonstrating presence of human cells in lung (human β2-microglobulin+) 15 min after IV infusion of hMSCs.
Figure 6C:
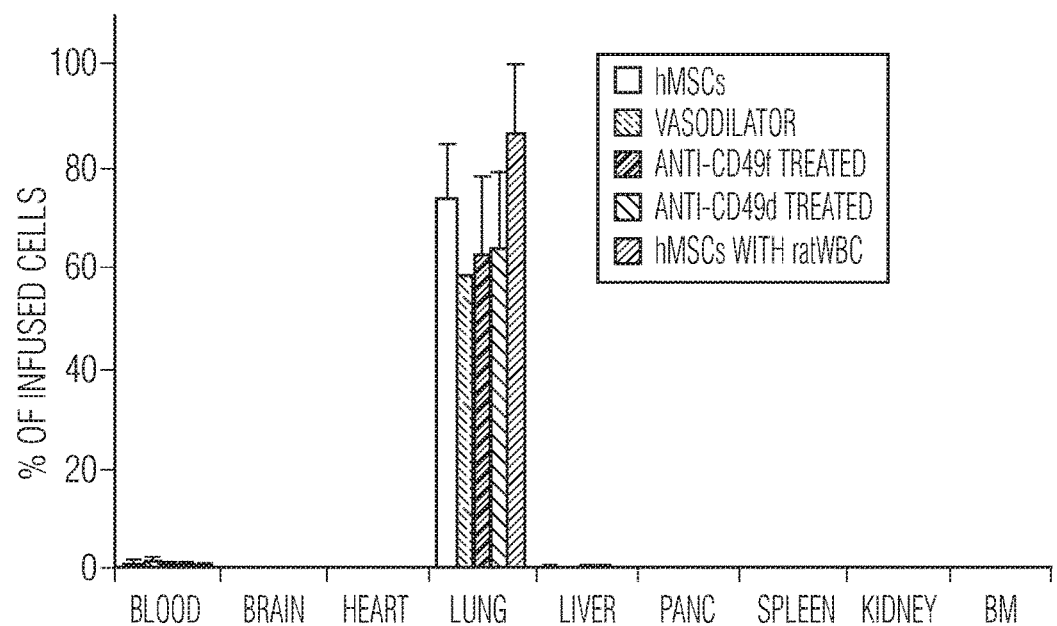
FIG. 6C: Tissue distribution of human Alu sequences 15 min after IV administration of hMSCs ($10^6$) without and with prior administration of a vasodilator, or with prior incubation of the cells with antibodies to CD49f or CD49d, or infusion together with human WBCs ($10^6$).
Figure 6D:
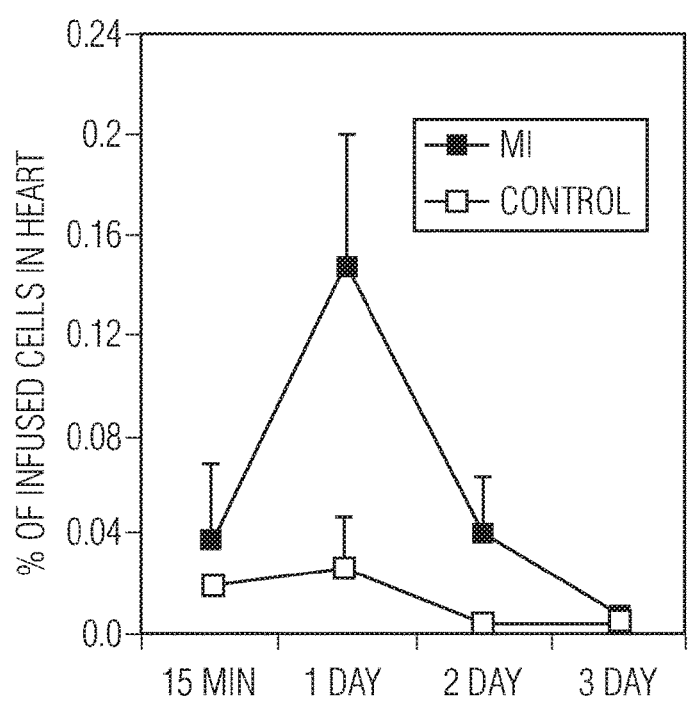
FIG. 6D: Delayed appearance of hMSCs infused IV one day after MI.

The inventors employed an improved PCR assay (see below) for human Alu to compare the engraftment of RS-MSCs ($PODXL^{hi}/CD49f^{hi}$) into mice with MIs. As indicated in FIG. 4, the RS-MSCs engrafted more efficiently into the hearts with MI. The cells also engrafted more efficiently into kidney, apparently as a result of secondary damage to the kidney, as reflected by an increase in serum creatinine levels (0.53 mg/dcl±0.08 SD vs 1.08±0.14 SD; n=4).

Figure 3A:
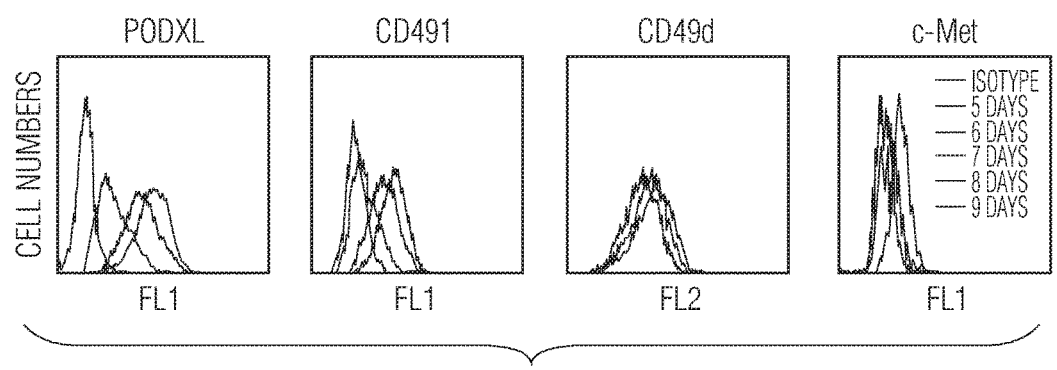
FIG. 3A shows Viable Passage 1/donor 4 MSCs plated at 100 cells/cm$^2$ and incubated for 5, 6, 7, 8, or 9 days. Cells were lifted with trypsin/EDTA.
Figure 3B:
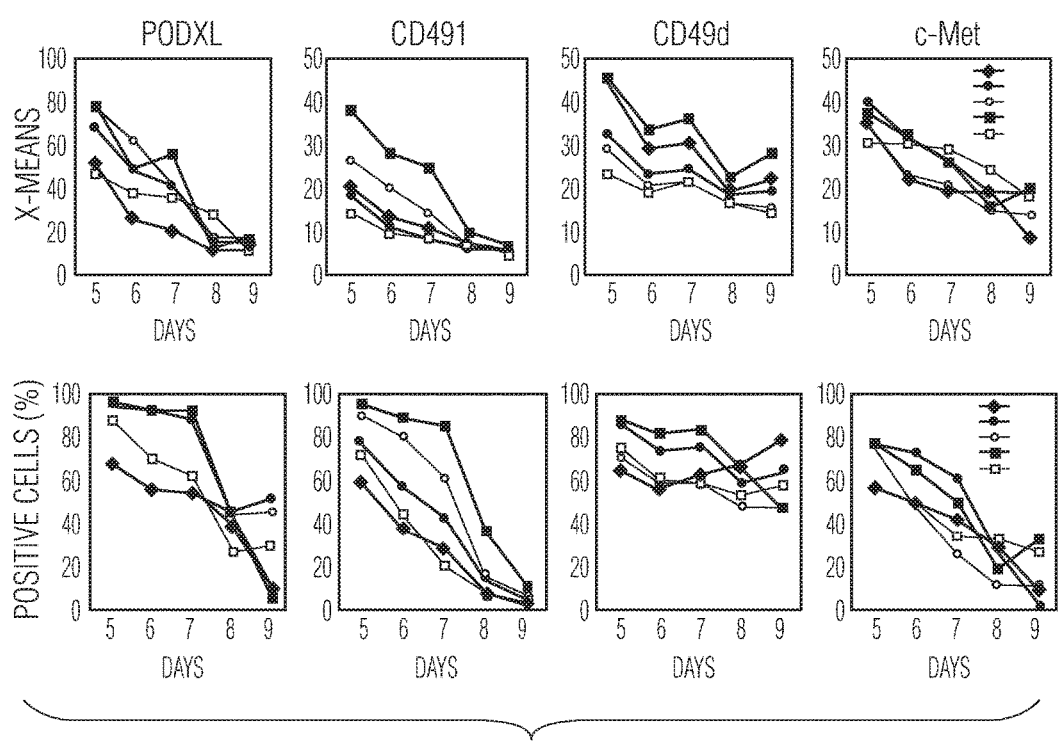
FIG. 3B shows data obtained with MSCs from 5 donors under conditions as in FIG. 3A. Values expressed either as mean fluorescence intensity (X-means) or % positive cells.
Figure 3C:
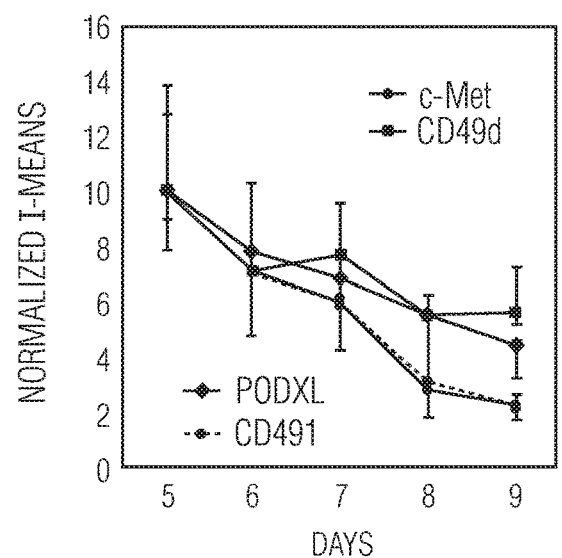
FIG. 3C shows X-mean values from FIG. 3B normalized to values for day 5.
Figure 3D:
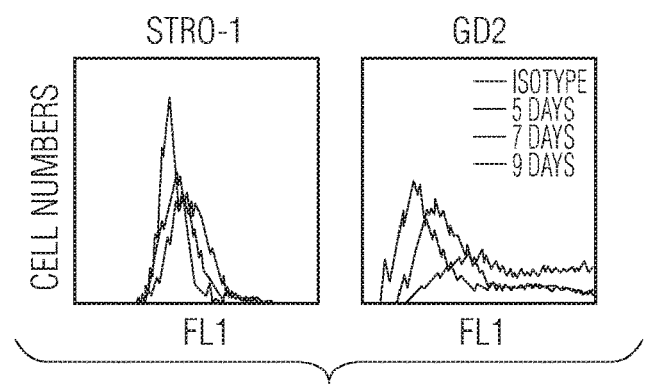
FIG. 3D shows FACScan from Passage 1/donor 1 MSCs incubated as in FIG. 3A and assayed for STRO-1 and GD2.
Figure 3E:
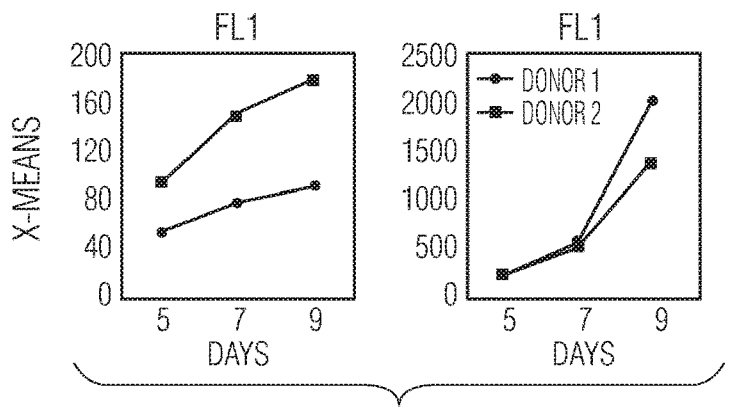
FIG. 3E shows X-means values from Passage 1/donor 1 and donor 7 MSCs.

As demonstrated in FIG. 3D, cultures of MSCs from some donors remained $PODXL^{hi}/CD49f^{hi}$ when plated at 100 cells/cm² and expanded for up to 7 days. In order to conveniently obtain adequate numbers of cells, 7 day cultures enriched for RS-MSCs from such selected donors were used for subsequent experiments. Unless otherwise noted, they are referred to simply as MSCs.

Example 3

Tissue Distribution of Infused hMSCs, Cancer Cells, and Human WBCs

After IV infusion into mice, hMSCs were cleared from the blood in less than 5 min (FIG. 5, Top Left). In confirmation of previous reports (Barbash et al., 2003; Gao et al., 2001b; Schrepfer et al., 2007), most of the infused cells were trapped in the lung (FIG. 5, Bottom Left). Similar observations were made with a human breast cancer cell line (MDA-MB-231) and with human WBCs, except a fraction of the human WBCs escaped trapping in the lung and were recovered in liver. hMSCs infused into the left ventricle of the heart (IC infused) were also cleared from the blood in less than 5 min (FIG. 5, Top Right), but compared to IV infusions larger numbers of hMSCs appeared in brain, heart, lung, liver, pancreas, spleen, kidney and bone marrow (FIG. 5, Bottom Right).

Alu sequences were assayed in blood, lung and seven tissues of mice for up to 4 days (100 hr) after IV infusions (FIG. 6, Top). There was no increase in human cells circulating in blood in the first 60 min, suggesting that few of the trapped cells were leaving the lung. Also, the recovery of the infused human DNA in the seven other tissues was less than a total of 0.2%, or fewer than 2,000 cells. The assays for Alu sequences in lung reflected live MSCs, since essentially same values were obtained by assays for human GAPDH mRNA (FIG. 6, Top Left). The number of MSCs trapped was decreased by immediate pretreatment of the mice with a vasodilator (sodium nitroprusside) (FIG. 6, Lower Left). There was no effect from pre-treatment of the cells with antibodies to α4-integrin or α6-integrin, or incubation with WBCs, all procedures reported to inhibit homing of hematopoietic stem cells to bone marrow (Qian et al. 2006; Chute, 2006). In addition, the proportion of hMSCs trapped in the lung was not decreased by reducing the number of cells infused to as little as $10^4$ (not shown). In mice with permanent MI produced one day before the IV infusions of hMSCs, there was a delayed appearance of a small number of hMSCs (<2,000) in heart (FIG. 6, Bottom, Lower Right).

Example 4

The Transcriptomes of Both Mouse Lung Cells and hMSCs Change after hMSCs are Trapped in the Lung To examine the effects of hMSCs being trapped in the lung, RNA was extracted from mouse lungs 10 hr after MSCs were IV infused and the RNA assayed on both mouse-specific and human-specific microarrays. As expected, there were major changes in the mouse transcriptome: 755 genes were up-regulated, and 347 genes were down-regulated two-fold or more (not shown). In addition, there were also major changes in the transcriptome of the hMSCs: 451 genes were up-regulated, and 1,001 genes were down-regulated two-fold or more. The results, therefore, indicated that the hMSCs responded to cross-talk with the mouse lung containing emboli of hMSCs.

Figure 7:
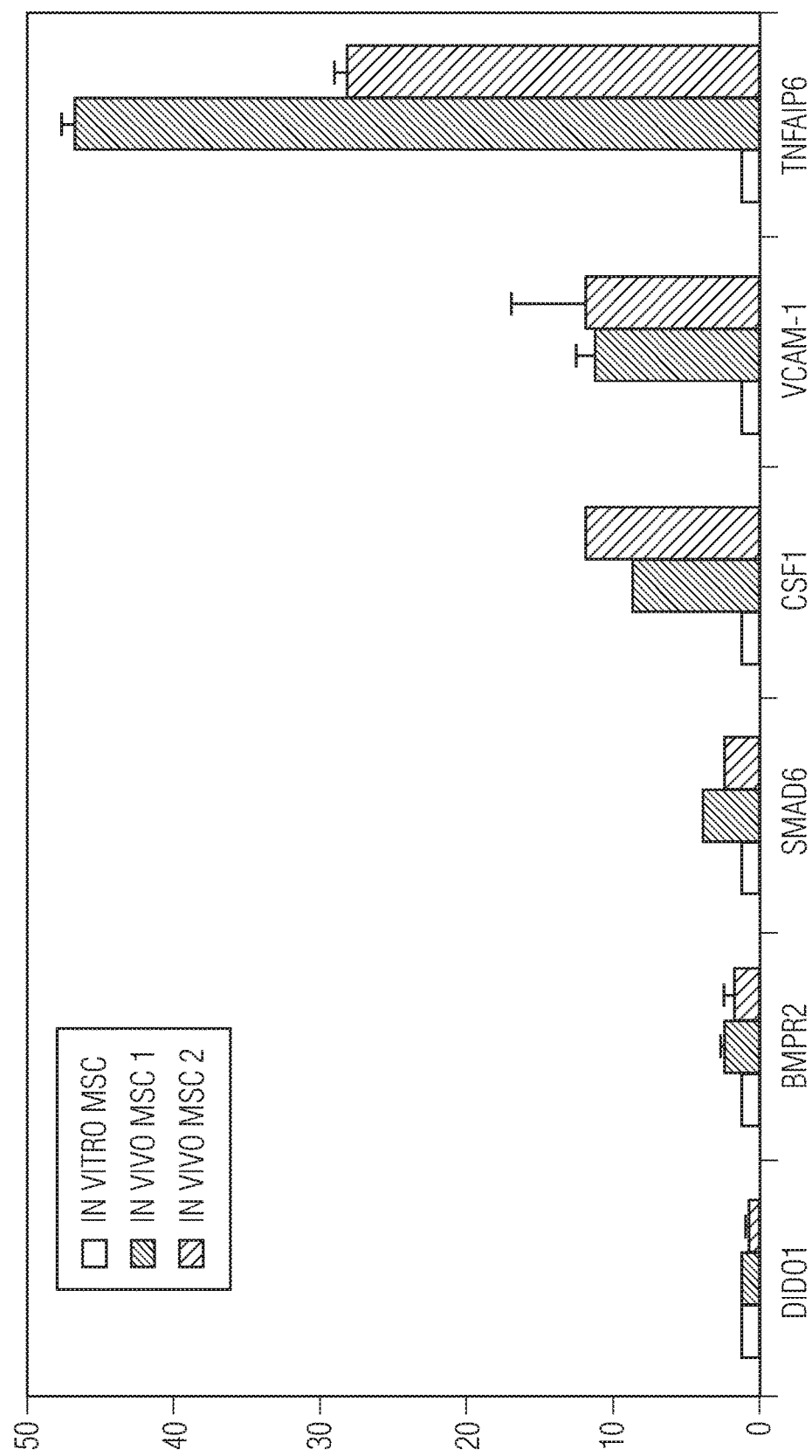
FIG. 7 shows results from real-time RT-PCR assays for human-specific mRNAs. Symbols: "In vitro MSC" refers to RNA for hMSCs before IV infusion to mice; "In vivo MSC 1" and "In vivo MSC 2" refer to RNA from lungs of two separate mice (mouse one and mouse two) 10 hr after IV infusion of hMSCs ($10^6$). Values are fold increases over levels observed in in vitro MSCs (set to value=1).

Subjective analysis of the several hundred human genes that were up-regulated two-fold or more in the hMSCs provided an interesting list of candidates for confirming the data by human-specific real-time RT-PCR assays (FIG. 7). The largest increase was a 30-fold or more increase in the transcript for TNF-α stimulated gene 6 (TNFAIP6 or TSG-6). The increase in TSG-6 was of particular interest because the protein was previously shown to be a powerful anti-inflammatory factor (Getting et al. 2002; Wisniewski and Vilcek 2004; Forteza et al., 2007; Milner et al., 2006). The 30 kDa protein was demonstrated to reduce inflammation by several actions: (i) it binds to and blocks the pro-inflammatory effects of fragments of hyaluronan; (ii) it forms a stable complex with inter-α-inhibitor and thus produces a 100-fold increase in the inhibition of serine proteases that are essential components of most inflammatory responses; (iii) it inhibits neutrophil chemotaxis; and (iv) in animal models of arthritis, it protects joint cartilage from degradation.

Example 5 hMSCs can be Activated to Express High Levels of TSG-6

To examine TSG-6 synthesis by hMSCs, hMSCs were incubated with the pro-inflammatory cytokine TNF-α. The hMSCs were activated to express 60- to 120-fold levels of the TSG-6 transcript (FIG. 8, Top Left). Unstimulated hMSCs did not secrete measurable amounts of the protein but hMSCs activated by TNF-α secreted large amounts (FIG. 8, Middle Panels). Knock down of the gene with siRNAs decreased both the level of the transcript and the secretion of the protein (FIG. 8, Bottom Panels). Surprisingly, the response of hMSCs to TNF-α far exceeded the response of human fibroblasts, even though TSG-6 was first discovered in fibroblasts incubated with TNF-α (Wisniewski and Vilcek 2004).

Example 6

Figure 9A:
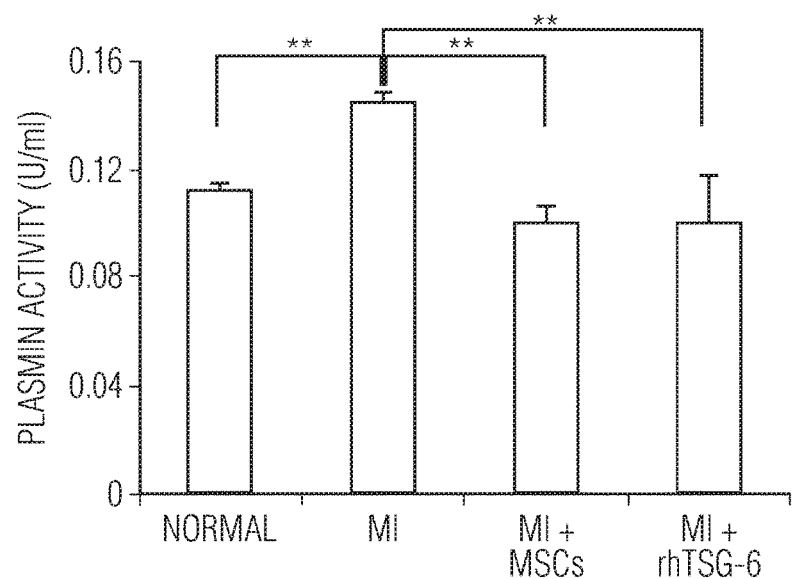
FIG. 9A shows serum plasmin activity by chromozym PL (Roche Applied Science). Values are ±SD; ** $p<0.01$ with n=3.
Figure 9B:
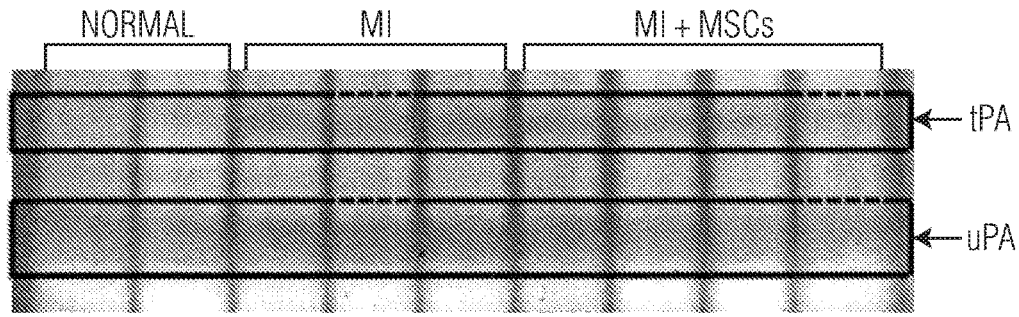
FIG. 9B shows the results of hearts assayed for tissue plasminogen activator (tPA) and urokinase (uPA) on a casein zymogen gel (Invitrogen).
Figure 9C:
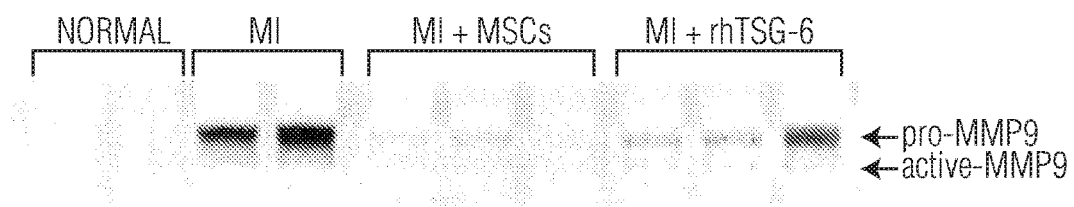
FIG. 9C shows the results of hearts assayed for pro- and active-matrix metalloprotease on a gelatin zymogen gel (Invitrogen).

Both IV MSCs and Recombinant TSG-6 Decrease Pro-Inflammatory Proteases in Serum and Heart in Mice with MI Permanent MI was produced in immunodeficient mice, and hMSCs were then infused into a tail vein under conditions that the inventors previously observed to improve left ventricular ejection fraction (Iso et al., 2007). Assays of serum demonstrated that plasmin activity was increased in mice with MI and that IV administration of hMSCs one hour later decreased the activity (FIG. 9A). Also, the effect of hMSCs was reproduced by a singe IV infusion of human recombinant TSG-6. Assays of heart demonstrated that levels of tissue plasminogen activator (tPA), urokinase (uPA), pro-matrix metalloproteinase 9 (pro-MMP9) and active MMP9 were increased in mice with MI (FIGS. 9B and 9C).

The results are of special interest because of the known anti-inflammatory effects of TSG-6 and the evidence that activation of proteinases, including MMP9 (Moshal et al., 2007), contributes to the inflammatory responses and deleterious effects of cardiac diseases (Ovechkin et al., 2005; Paolocci et al., 2006; Carvalho et al., 2006).

Example 7

Supplemental Methods
Data Obtained Using the Following Methods are Described Below.

A. Preparations of MSCs:

The hMSCs were obtained from the Center for Preparation and Distribution of Adult Stem Cells. The cells consistently differentiated into three lineages in culture, were negative for hematopoietic markers (CD34, CD36, CD117 and CD45), and positive for CD29 (95%), CD44 (>93%), CD49c (99%), CD49f (>70%), CD59 (>99%), CD90 (>99%), CD105 (>99%) and CD166 (>99%). Vials of about 1 million cells (passage 1 or 2) were thawed, plated on a 174 cm² dish (Nunc) in 25 ml of complete culture medium (CCM), and incubated at 37° C. in 5% $CO_2$. The CCM was α-MEM (GIBCO/BRL) containing 17% FBS (lot-selected for rapid growth of hMSCs; Atlanta Biologicals, Lawrenceville, Ga.); 100 units/ml of penicillin; 100 µg/ml of streptomycin; and 2 mM L-glutamine (GIBCO/BRL). After 1 day, the medium was replaced, the cultures were washed with PBS to remove non-adherent cells, and then they were incubated with 0.25% trypsin/1 mM EDTA (GIBCO/BRL) for 5 min at 37° C. to recover viable cells. The cells were concentrated by centrifugation at 800×g for 10 min, suspended in CCM, replated at 100 cells/cm² in a 174 cm² dish, and incubated for 6 to 7 days until 70% confluent so that about 50% of the cells were positive for the anti-cell adhesion protein PODOXL (Lee et al., 2009). Mouse (C57/Bl6) MSCs from bone marrow were also obtained from the Center and expanded to passage 5 as described (Peister et al., 2004).

Human breast carcinoma cells (MDA-MB 231; American Type Culture Collection) from frozen vials were plated at 10,000 cells/cm² and expanded to 80% confluency through two passages. Culture medium for MDA-MB 231 cells contained high glucose DMEM (GIBCO/BRL) supplemented with 10% FBS (Atlanta Biologicals); 100 units/ml of penicillin; 100 μg/ml of streptomycin; and 2 mM L-glutamine (GIBCO/BRL). Human skin fibroblasts (gift from Dr. Carl Gregory, Institute for Regenerative Medicine) from the same donor who provided the hMSCs were expanded under the same conditions. Human white blood cells (hWBCs) were prepared from fresh samples of heparinized peripheral blood, isolated by density gradient centrifugation (Ficoll Hypaque; Pharmacia Biotechnology), and washed with PBS. The carcinoma cells and hWBCs were infused into mice under the same conditions as the hMSCs.

Figure 10:
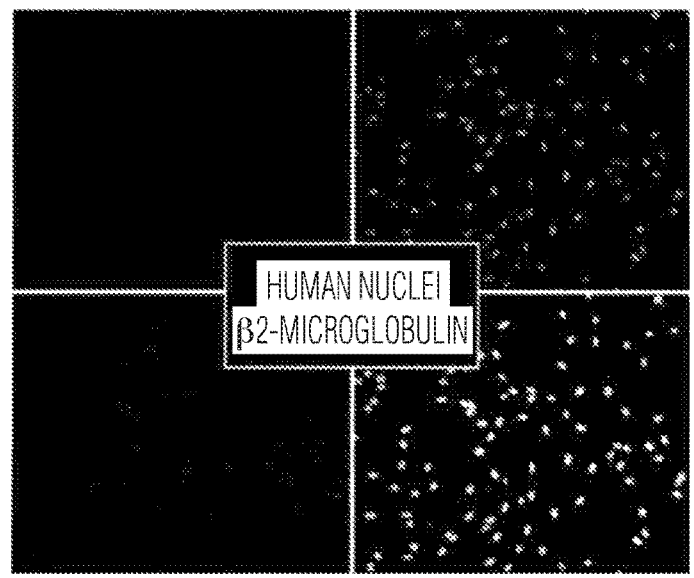
FIG. 10. Circulating hMSCs after Intravenous Administration. CFU-f assay from mouse blood 15 min after intravenous administration of hMSCs. Colonies were labeled with anti-human nuclei, β2-microglobulin and DAPI.
Figure 11A:
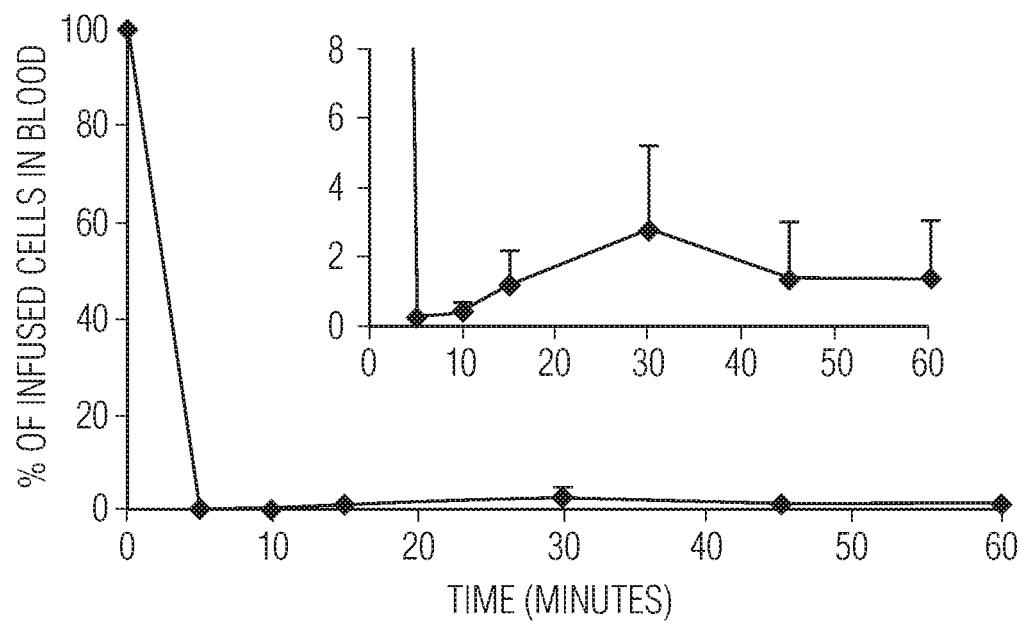
FIG. 11. Circulating hMSCs and Tissues Distribution after Intracardiac Administration. A. Clearance of human Alu sequences from blood after intracardiac infusion of about $2 \times 10^6$ hMSCs into mice. Values are means+/−S.D; n=6. B. Tissues distribution of human Alu sequences 15 min after intracardiac infusion of about $2 \times 10^6$ hMSCs into mice. Values are means+/−S.D; n=6.
Figure 11B:
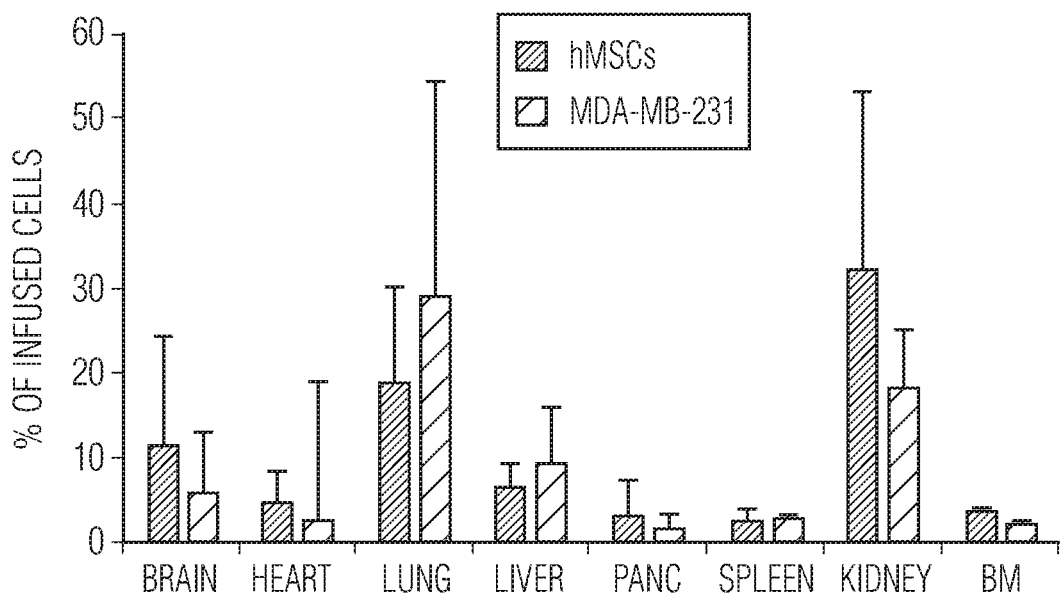
Figure 12A:
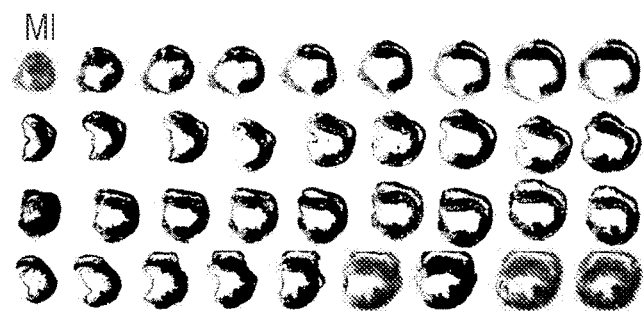
FIG. 12. Histology Sections from Heart 3 wk after MI. The heart was cut from the apex through base into 5 μm sections and stained with Masson Trichrome. Every $20^{th}$ section covering the infarct is shown. Symbols as in FIG. 16 B; n=3 or 4 hearts.
Figure 12B:
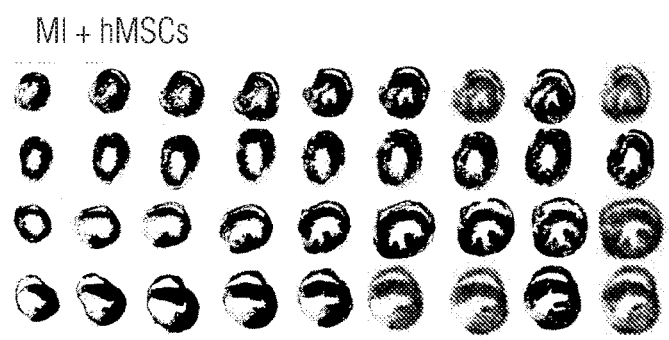
Figure 12C:
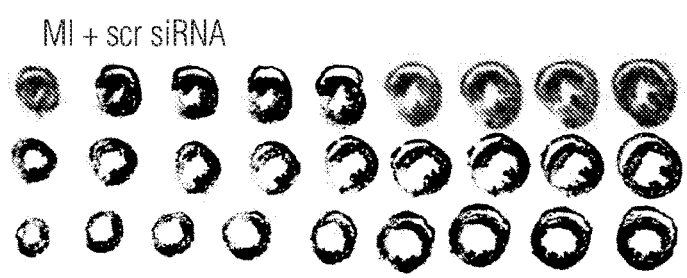
Figure 12D:
Figure 12E:
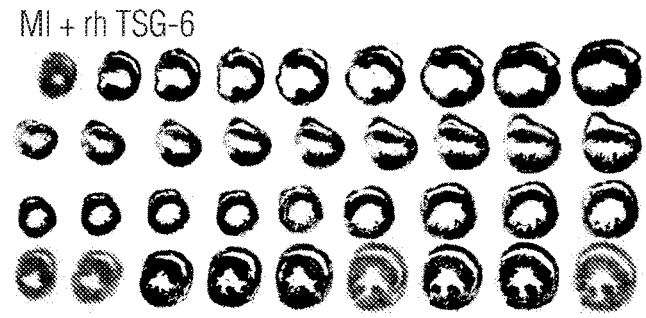

B. Detection of hMSCs in Blood:

For detection of hMSCs in mouse blood 15 min after IV infusion, 50 μl of blood was plated on a 10 cm dish in CCM. After 1 day, cells were washed with PBS, covered with 10 ml CCM and incubated 14 days with changes of medium every 3 to 4 days. Colonies (FIG. 10) were fixed with 4% paraformaldehyde for 20 min, labeled with anti-human nuclei antigen (1:200; clone 235-1; Chemicon) and anti-human β2-microglobulin (1:200; Roche) and mounted with DAPI (VECTASHIELD® Mounting Medium with DAPI; Vector Laboratories).

C. Incubations of hMSCs and Fibroblasts:

hMSCs, mouse MSCs and fibroblasts were plated at 50,000 cells/well in CCM in 6-well plates and incubated for 18 hours. The medium was removed without washing to retain some FBS on the cells and replaced with serum-free CCM containing 10 ng/ml of recombinant human TNF-α (R&D Systems). After incubation for 0 to 48 hours, total RNA was extracted (RNeasy Mini Kit; QIAGEN) for RT-PCR assays and medium was recovered for ELISAs.

D. Cardiac Troponin—ELISA:

Cardiac troponin I concentrations were determined on serum from mice on 2 days after LAD ligation using the murine troponin I ELISA kit (Life Diagnostics Inc.) according to the directions of the manufacturer.

E. Plasmin Activity:

Two million of Passage 2 MSCs were infused IV into mice 1 hr after MI and serum and hearts were collected after 48 hr. Plasmin activity from mice serum was assayed using a chromozym PL (Roche Applied Science) as a chromogenic substrate in 50 mM Tris, pH 7.4 and 0.9% NaCl. Reaction mixtures were incubated at 37° C. and assayed spectrophotometrically at 405 nm every 2 min for 30 min. The values were expressed as average change in absorbance per min.

F. Zymograms:

Heart tissue was homogenized on ice in lysis buffer (1% Triton X-100, 0.1% of SDS, 0.1% sodium azide in 1×PBS pH 7.2) and incubated with rotation for 1 hr at 4° C. Lysates were cleared by centrifugation at 12,000 g for 10 min at 4° C. Five-microliter aliquots of heart extracts were analyzed by zymography using precast gelatin gels (10% Zymogram Gelatin Gels; Invitrogen/Novex). With constant gentle agitation, gels were renatured for 30 minutes at room temperature, developed overnight at 37° C., stained with Colloidal Blue (Novex technical bulletin IM-6025), and extensively washed (>20 hours) to yield uniform background signal. Digital images of stained wet gels were captured using a scanner.

G. Assays of mRNAs in Lung by Microarrays:

RNA was isolated from lungs of control mice, lungs of mice 10 hr after IV infusion of about 2 million hMSCs and lungs to which 1 million hMSCs were added just before homogenization. About 8 μg of total RNA was used for assay on either the mouse (MG-430 2.0) or human (HG-U133 Plus 2.0) microarrays (Affymetrix). The data analyzed using Microarray Suite 5.0 (MASS 5.0; Affymetrix) and dChip 1.3+ programs (Schadt et al., 2001). Values were expressed as fold-changes relative to the signal intensities on either control mouse lung, control mouse lung with hMSCs added before homogenization or mouse lung after IV infusion of hMSCs. The data were filtered for cross-hybridization (CV>0.5 and call >33%), analyzed with the Microarray Suite 5.0 program, and normalized to a value of 1 and variance of 3 SD (+3, red; 3, blue) as described (Ohtaki et al., 2008).

Example 8

Upregulated and Downregulated Transcripts of hMSCs Up-Regulated in Lung after IV Infusion

TABLE 1

The top 100 transcripts of hMSCs up-regulated in lung after IV infusion versus control hMSCs.

| probe set | NAME | FOLD CHANGE |
|---|---|---|
| 238410_x_at | Transcribed locus | 48.21 |
| 1554963_at | CDNA clone IMAGE: 5310797 | 33.22 |
| 1555938_x_at | VIM: vimentin | 28.23 |
| 207361_at | HBP1: HMG-box transcription factor 1 | 28.2233 |
| 242237_at | Hs.15546.1 | 25.81 |
| 224533_s_at | IFI6: Interferon, alpha-inducible protein 6 | 23.34921 |
| 213213_at | DIDO1: death inducer-obliterator 1 | 23.16949 |
| 204084_s_at | CLN5: ceroid-lipofuscinosis, neuronal 5 | 18.01663 |
| 227489_at | SMURF2: SMAD specific E3 ubiquitin protein ligase 2 | 17.27481 |
| 1557512_at | Full length insert cDNA YQ02G04 | 16.64667 |
| 232791_at | MRNA; cDNA DKFZp761E2423 (from clone DKFZp761E2423) | 14.07853 |
| 1553148_a_at | SNX13: sorting nexin 13 | 13.74566 |
| 240760_at | CDRT15: CMT1A duplicated region transcript 15 | 12.67 |
| 1555124_at | MGC40574: hypothetical protein MGC40574 | 12.00258 |
| 201341_at | ENC1: ectodermal-neural cortex (with BTB-like domain) | 11.30631 |
| 223547_at | C14orf100: chromosome 14 open reading frame 100 | 11.07843 |
| 221485_at | B4GALT5: UDP-Gal:betaGlcNAc beta 1,4-galactosyltransferase, polypeptide 5 | 11.06061 |
| 218723_s_at | C13orf15: chromosome 13 open reading frame 15 | 11.00441 |
| 1565644_at | LOC143286: Hypothetical protein LOC143286 | 10.50617 |
| 216898_s_at | COL4A3: collagen, type IV, alpha 3 (Goodpasture antigen) | 10.49 |

TABLE 1-continued

The top 100 transcripts of hMSCs up-regulated in lung after IV infusion versus control hMSCs.

| probe set | NAME | FOLD CHANGE |
|---|---|---|
| 204495_s_at | C15orf39: chromosome 15 open reading frame 39 | 10.39 |
| 201638_s_at | CPSF1: cleavage and polyadenylation specific factor 1, 160 kDa | 10.35407 |
| 238277_at | Hs.270736.0 | 10.23377 |
| 207876_s_at | FLNC: filamin C, gamma (actin binding protein 280) | 10.22951 |
| 216809_at | CYLC1: cylicin, basic protein of sperm head cytoskeleton 1 | 9.735043 |
| 244440_at | Hs.132639.0 | 9.581967 |
| 218371_s_at | PSPC1: paraspeckle component 1 | 8.958084 |
| 208166_at | MMP16: matrix metallopeptidase 16 (membrane-inserted) | 8.888031 |
| 1563687_a_at | FRYL: FRY-like | 8.089494 |
| 1567377_at | DNAH1: dynein, axonemal, heavy chain 1 | 7.935123 |
| 234375_x_at | Hs.248068.0 | 7.871502 |
| 214319_at | FRY: furry homolog (Drosophila) | 7.626556 |
| 225266_at | ZNF652: Zinc finger protein 652 | 7.558789 |
| 214214_s_at | C1QBP: complement component 1, q subcomponent binding protein | 7.543278 |
| 206026_s_at | TNFAIP6: tumor necrosis factor, alpha-induced protein 6 | 7.542601 |
| 204419_x_at | HBG2: hemoglobin, gamma G | 7.489239 |
| 244660_at | ELAVL1: ELAV (embryonic lethal, abnormal vision, Drosophila)-like 1 (Hu antigen R) | 7.270169 |
| 201940_at | CPD: carboxypeptidase D | 7 |
| 225981_at | C17orf28: chromosome 17 open reading frame 28 | 6.984326 |
| 210580_x_at | SULT1A3 /// SULT1A4: sulfotransferase family, cytosolic, 1A, phenol-preferring, member 3 /// sulfotransferase family, cytosolic, 1A, phenol-preferring, member 4 | 6.9245 |
| 223385_at | CYP2S1: cytochrome P450, family 2, subfamily S, polypeptide 1 | 6.793651 |
| 239409_at | Transcribed locus | 6.776163 |
| 1560631_at | CALCOCO2: calcium binding and coiled-coil domain 2 | 6.495642 |
| 214414_x_at | HBA2: Hemoglobin, alpha 2 | 6.22943 |
| 242311_x_at | Transcribed locus | 6.122634 |
| 1569434_at | C14orf105: chromosome 14 open reading frame 105 | 6.116935 |
| 238909_at | S100A10: S100 calcium binding protein A10 | 6.111111 |
| 208690_s_at | PDLIM1: PDZ and LIM domain 1 (elfin) | 6.047536 |
| 243705_at | DDHD1: DDHD domain containing 1 | 5.90131 |
| 215217_at | Hs.306357.0 | 5.880654 |
| 231872_at | LRRCC1: leucine rich repeat and coiled-coil domain containing 1 | 5.853448 |
| 237263_at | Full length insert cDNA clone YI54D04 | 5.829268 |
| 209328_x_at | HIGD2A: HIG1 domain family, member 2A | 5.725146 |
| 230701_x_at | KIF9: kinesin family member 9 | 5.479769 |
| 234423_x_at | CDNA clone IMAGE: 4814259 | 5.297945 |
| 228203_at | B3GNT1: UDP-GlcNAc:betaGal beta-1,3-N-acetylglucosaminyltransferase 1 | 5.232283 |
| 1565920_at | MRNA from chromosome 5q21-22, clone: LI26 | 5.222717 |
| 221667_s_at | HSPB8: heat shock 22 kDa protein 8 | 5.2 |
| 231482_at | MRNA; cDNA DKFZp781G0123 (from clone DKFZp781G0123) | 5.159578 |
| 216440_at | ERC1: ELKS/RAB6-interacting/CAST family member 1 | 5.04886 |
| 240031_at | Hs.98908.0 | 5.04497 |
| 1555122_at | GPR125: G protein-coupled receptor 125 | 4.981132 |
| 1559257_a_at | MAGI1: membrane associated guanylate kinase, WW and PDZ domain containing 1 | 4.89898 |
| 217916_s_at | FAM49B: family with sequence similarity 49, member B | 4.852612 |
| 221002_s_at | TSPAN14: tetraspanin 14 | 4.834464 |
| 1566437_at | LOC283475: Hypothetical protein LOC283475 | 4.661017 |
| 242464_at | Transcribed locus | 4.643432 |
| 232198_at | CDNA FLJ12676 fis, clone NT2RM4002383 | 4.570205 |
| 201925_s_at | CD55: CD55 molecule, decay accelerating factor for complement (Cromer blood group) | 4.536667 |
| 1556151_at | ITFG1: Integrin alpha FG-GAP repeat containing 1 | 4.521212 |
| 235629_at | Transcribed locus, strongly similar to XP_516072.1 similar to fibronectin 1 isoform 2 preproprotein; cold-insoluble globulin; migration-stimulating factor (Pan troglodytes) | 4.513873 |
| 222835_at | THSD4: thrombospondin, type I, domain containing 4 | 4.482496 |
| 241197_at | Transcribed locus | 4.48 |
| 242413_at | Hs.272102.0 | 4.464191 |
| 208138_at | GAST: gastrin | 4.4228 |
| 228793_at | JMJD1C: jumonji domain containing 1C | 4.419421 |
| 236404_at | Transcribed locus | 4.375405 |
| 243999_at | SLFN5: schlafen family member 5 | 4.352612 |
| 1554423_a_at | FBXO7: F-box protein 7 | 4.330941 |
| 203868_s_at | VCAM1: vascular cell adhesion molecule 1 | 4.31831 |
| 244396_at | G3BP1: GTPase activating protein (SH3 domain) binding protein 1 | 4.311978 |
| 206748_s_at | SPAG9: sperm associated antigen 9 | 4.309241 |
| 238644_at | MYSM1: myb-like, SWIRM and MPN domains 1 | 4.29351 |
| 240089_at | Transcribed locus | 4.285714 |
| 210718_s_at | ARL17P1: ADP-ribosylation factor-like 17 pseudogene 1 | 4.226876 |
| 1553181_at | DDX31: DEAD (Asp-Glu-Ala-Asp) box polypeptide 31 | 4.208333 |

TABLE 1-continued

The top 100 transcripts of hMSCs up-regulated in lung after IV infusion versus control hMSCs.

| probe set | NAME | FOLD CHANGE |
|---|---|---|
| 201941_at | CPD: carboxypeptidase D | 4.208217 |
| 48030_i_at | C5orf4: chromosome 5 open reading frame 4 | 4.17192 |
| 241656_at | Transcribed locus | 4.165379 |
| 1558308_at | FLJ33297: hypothetical gene supported by AK090616 | 4.134809 |
| 215643_at | CDNA FLJ11740 fis, clone HEMBA1005500 | 4.053021 |
| 239201_at | ALS2CR7: amyotrophic lateral sclerosis 2 (juvenile) chromosome region, candidate 7 | 4.034933 |
| 233839_at | FLJ23588: CAP-binding protein complex interacting protein 1 | 4.00428 |
| 212730_at | DMN: desmuslin | 3.998357 |
| 1563509_at | MRNA; cDNA DKFZp313O229 (from clone DKFZp313O229) | 3.994979 |
| 226465_s_at | SON: SON DNA binding protein | 3.980122 |
| 227099_s_at | LOC387763: hypothetical LOC387763 | 3.950474 |
| 1558128_at | LOC730202: hypothetical protein LOC730202 | 3.92766 |
| 218640_s_at | PLEKHF2: pleckstrin homology domain containing, family F (with FYVE domain) member 2 | 3.903145 |
| 1560449_at | CDNA FLJ32886 fis, clone TESTI2004255 | 3.877614 |

TABLE 2

The top 100 transcripts of hMSCs down-regulated in lung after IV infusion versus control hMSCs.

| probe set | NAME | FOLD CHANGE |
|---|---|---|
| 222486_s_at | ADAMTS1: ADAM metallopeptidase with thrombospondin type 1 motif, 1 | 69.67 |
| 201528_at | RPA1: replication protein A1, 70 kDa | 60.39 |
| 236808_at | FGFR1OP2: FGFR1 oncogene partner 2 | 43.32 |
| 209101_at | CTGF: connective tissue growth factor | 41.86895 |
| 220299_at | SPATA6: spermatogenesis associated 6 | 41.41538 |
| 231470_at | ZNF493: Zinc finger protein 493 | 37.03 |
| 205060_at | LOC727726 /// PARG: poly (ADP-ribose) glycohydrolase /// similar to poly (ADP-ribose) glycohydrolase | 35.23 |
| 1557419_a_at | ACSL4: Acyl-CoA synthetase long-chain family member 4 | 34.64516 |
| 229057_at | SCN2A: sodium channel, voltage-gated, type II, alpha subunit | 33.35 |
| 203637_s_at | MID1: midline 1 (Opitz/BBB syndrome) | 31.63115 |
| 213899_at | METAP2: methionyl aminopeptidase 2 | 28.48 |
| 1557521_a_at | CDNA clone IMAGE: 5311184 | 28.01667 |
| 219049_at | ChGn: chondroitin beta1,4 N-acetylgalactosaminyltransferase | 27.86 |
| 234210_x_at | ACTR2: ARP2 actin-related protein 2 homolog (yeast) | 27.63 |
| 235418_at | LOC285014: hypothetical protein LOC285014 | 25.40152 |
| 234826_at | MRNA; cDNA DKFZp434A2111 (from clone DKFZp434A2111) | 25.024 |
| 226836_at | SFT2D1: SFT2 domain containing 1 | 21.57 |
| 206100_at | CPM: carboxypeptidase M | 20.57 |
| 1558315_s_at | HOOK3: Hook homolog 3 (*Drosophila*) | 20.35965 |
| 218392_x_at | SFXN1: sideroflexin 1 | 19.86164 |
| 227814_at | WDR53: WD repeat domain 53 | 16.99 |
| 203690_at | TUBGCP3: tubulin, gamma complex associated protein 3 | 16.47 |
| 215450_at | Hs.1066.2 | 14.78 |
| 221245_s_at | FZD5: frizzled homolog 5 (*Drosophila*) | 14.12575 |
| 201924_at | AFF1: AF4/FMR2 family, member 1 | 13.03114 |
| 1569294_at | RNF187: Ring finger protein 187 | 11.68 |
| 1563055_at | CDNA clone IMAGE: 5312112 | 11.41 |
| 220014_at | PRR16: proline rich 16 | 11.28704 |
| 231202_at | ALDH1L2: aldehyde dehydrogenase 1 family, member L2 | 11.27632 |
| 212140_at | SCC-112: SCC-112 protein | 10.10993 |
| 202865_at | DNAJB12: DnaJ (Hsp40) homolog, subfamily B, member 12 | 9.997279 |
| 217622_at | RHBDD3: rhomboid domain containing 3 | 9.95283 |
| 207102_at | AKR1D1: aldo-keto reductase family 1, member D1 (delta 4-3-ketosteroid-5-beta-reductase) | 9.9437 |
| 201109_s_at | THBS1: thrombospondin 1 | 9.916224 |
| 224810_s_at | ANKRD13A: ankyrin repeat domain 13A | 9.011029 |
| 223391_at | SGPP1: sphingosine-1-phosphate phosphatase 1 | 8.503165 |
| 202516_s_at | DLG1: discs, large homolog 1 (*Drosophila*) | 8.309904 |
| 237973_at | Transcribed locus | 7.989865 |
| 229003_x_at | FAM69B: Family with sequence similarity 69, member B | 7.69086 |
| 218197_s_at | OXR1: oxidation resistance 1 | 7.446215 |
| 207678_s_at | SOX30: SRY (sex determining region Y)-box 30 | 7.177885 |
| 1566966_at | CDNA: FLJ20864 fis, clone ADKA01825 | 6.959402 |
| 209094_at | DDAH1: dimethylarginine dimethylaminohydrolase 1 | 6.955416 |

TABLE 2-continued

The top 100 transcripts of hMSCs down-regulated in lung after IV infusion versus control hMSCs.

| probe set | NAME | FOLD CHANGE |
|---|---|---|
| 206157_at | PTX3: pentraxin-related gene, rapidly induced by IL-1 beta | 6.835649 |
| 224714_at | MKI67IP: MKI67 (FHA domain) interacting nucleolar phosphoprotein | 6.738727 |
| 212530_at | NEK7: NIMA (never in mitosis gene a)-related kinase 7 | 6.681952 |
| 227627_at | SGK3: serum/glucocorticoid regulated kinase family, member 3 | 6.588785 |
| 220166_at | CNNM1: cyclin M1 | 6.53833 |
| 1552797_s_at | PROM2: prominin 2 | 6.405797 |
| 1559930_at | CDNA clone IMAGE: 5278137 | 6.365385 |
| 208123_at | KCNB2: potassium voltage-gated channel, Shab-related subfamily, member 2 | 6.329289 |
| 231830_x_at | RAB11FIP1: RAB11 family interacting protein 1 (class I) | 6.28496 |
| 218468_s_at | GREM1: gremlin 1, cysteine knot superfamily, homolog (*Xenopus laevis*) | 6.255372 |
| 1560692_at | LOC285878: hypothetical protein LOC285878 | 6.180556 |
| 223824_at | C10orf59: chromosome 10 open reading frame 59 | 6.115869 |
| 214705_at | INADL: InaD-like (*Drosophila*) | 6.09291 |
| 234985_at | LDLRAD3: low density lipoprotein receptor class A domain containing 3 | 5.938416 |
| 201250_s_at | SLC2A1: solute carrier family 2 (facilitated glucose transporter), member 1 | 5.912568 |
| 1562894_at | *Homo sapiens*, clone IMAGE: 4716286, mRNA | 5.839771 |
| 202912_at | ADM: adrenomedullin | 5.809269 |
| 214198_s_at | DGCR2: DiGeorge syndrome critical region gene 2 | 5.72076 |
| 224960_at | SCYL2: SCY1-like 2 (*S. cerevisiae*) | 5.579832 |
| 219078_at | GPATCH2: G patch domain containing 2 | 5.475036 |
| 240418_at | Transcribed locus | 5.339073 |
| 228822_s_at | USP16: ubiquitin specific peptidase 16 | 5.326316 |
| 1557672_s_at | CDNA FLJ32851 fis, clone TESTI2003432 | 5.316832 |
| 220305_at | MGC3260: hypothetical protein MGC3260 | 5.314 |
| 238519_at | RSC1A1: regulatory solute carrier protein, family 1, member 1 | 5.283186 |
| 228562_at | Transcribed locus | 5.233962 |
| 241834_at | Full-length cDNA clone CS0DC013YI04 of Neuroblastoma Cot 25-normalized of *Homo sapiens* (human) | 5.187683 |
| 209469_at | GPM6A: glycoprotein M6A | 5.087657 |
| 214836_x_at | IGKC /// IGKV1-5: immunoglobulin kappa constant /// immunoglobulin kappa variable 1-5 | 5.076484 |
| 216489_at | TRPM3: transient receptor potential cation channel, subfamily M, member 3 | 5.071739 |
| 244863_at | Transcribed locus | 5.060403 |
| 209895_at | PTPN11: protein tyrosine phosphatase, non-receptor type 11 (Noonan syndrome 1) | 5.045392 |
| 243982_at | KLHL28: Kelch-like 28 (*Drosophila*) | 4.974937 |
| 210762_s_at | DLC1: deleted in liver cancer 1 | 4.914197 |
| 1554351_a_at | TIPRL: TIP41, TOR signalling pathway regulator-like (*S. cerevisiae*) | 4.824107 |
| 243488_at | GPRIN3: GPRIN family member 3 | 4.783493 |
| 235410_at | NPHP3: nephronophthisis 3 (adolescent) | 4.783217 |
| 211170_s_at | PDE10A: phosphodiesterase 10A | 4.778784 |
| 233770_at | CDNA FLJ12077 fis, clone HEMBB1002453 | 4.754414 |
| 224862_at | GNAQ: Guanine nucleotide binding protein (G protein), q polypeptide | 4.628492 |
| 202738_s_at | PHKB: phosphorylase kinase, beta | 4.616261 |
| 218130_at | C17orf62: chromosome 17 open reading frame 62 | 4.565367 |
| 213664_at | SLC1A1: solute carrier family 1 (neuronal/epithelial high affinity glutamate transporter, system Xag), member 1 | 4.554664 |
| 1556768_at | CDNA FLJ35829 fis, clone TESTI2006460 | 4.429213 |
| 212930_at | ATP2B1: ATPase, Ca++ transporting, plasma membrane 1 | 4.395189 |
| 1560485_at | HIVEP1: human immunodeficiency virus type I enhancer binding protein 1 | 4.393759 |
| 231199_at | Transcribed locus, weakly similar to NP_001909.2 branched chain transacylase precursor (*Homo sapiens*) | 4.383821 |
| 211615_s_at | LRPPRC: leucine-rich PPR-motif containing | 4.334266 |
| 218258_at | POLR1D: polymerase (RNA) I polypeptide D, 16 kDa | 4.300474 |
| 229398_at | RAB18: RAB18, member RAS oncogene family | 4.25042 |
| 222433_at | ENAH: enabled homolog (*Drosophila*) | 4.238413 |
| 218847_at | IGF2BP2: insulin-like growth factor 2 mRNA binding protein 2 | 4.236473 |
| 238283_at | LOC151658: hypothetical protein LOC151658 | 4.215447 |
| 210986_s_at | TPM1: tropomyosin 1 (alpha) | 4.201766 |
| 204337_at | RGS4: regulator of G-protein signalling 4 | 4.197537 |
| 218343_s_at | GTF3C3: general transcription factor IIIC, polypeptide 3, 102 kDa | 4.158664 |
| 219479_at | KDELC1: KDEL (Lys-Asp-Glu-Leu) containing 1 | 4.136832 |

Example 9

Echocardiographic Data 3 wk after MI

TABLE 3

Echocardiographic Data 3 wk after MI.

|  | LV fractional shortening (% LVFS) | LV ejection fraction (% LVEF) | LV diameter in end-diastole (LVDd) | LV diameter in end-systole (LVSd) |
|---|---|---|---|---|
| MI | 27.4 | 60 | 0.44 | 0.32 |
|  | 31.5 | 66.6 | 0.34 | 0.23 |
|  | 35.2 | 71.4 | 0.39 | 0.26 |
|  | 45.2 | 81.4 | 0.39 | 0.21 |
|  | 33.3 | 68.8 | 0.42 | 0.28 |
| MI + hMSCs | 46.3 | 84 | 0.33 | 0.18 |
|  | 46.8 | 84.1 | 0.31 | 0.17 |
|  | 43.5 | 80.8 | 0.41 | 0.23 |
|  | 47.2 | 84.3 | 0.37 | 0.2 |
|  | 48.7 | 85.6 | 0.36 | 0.18 |
|  | 42.1 | 79.6 | 0.31 | 0.18 |
|  | *p < 0.05 | *p < 0.05 | **N.S. | *p < 0.05 |
| MI + hMSCs transduced with scr siRNA | 42.8 | 80.2 | 0.35 | 0.2 |
|  | 41.1 | 78.4 | 0.39 | 0.23 |
|  | 50.1 | 86.6 | 0.41 | 0.2 |
|  | 45.6 | 83 | 0.32 | 0.18 |
|  | 42.7 | 80.2 | 0.33 | 0.19 |
|  | *p < 0.05 | *p < 0.05 | **N.S. | *p < 0.05 |
| MI + hMSCs transduced with TSG-6 siRNA | 33.1 | 68.7 | 0.37 | 0.25 |
|  | 40.8 | 78.2 | 0.35 | 0.21 |
|  | 39.8 | 76.8 | 0.42 | 0.26 |
|  | 35.4 | 71.5 | 0.43 | 0.28 |
|  | 47.5 | 84.5 | 0.41 | 0.21 |
|  | **N.S. | **N.S. | **N.S. | **N.S. |

*P values are compared to MI;
**N.S. = not significant.

Example 10

PCR Primer Sequences

TABLE 4

PCR Primer Sequences.

| Primer name | Sequences |
|---|---|
| Alu Forward Primer (SEQ ID NO: 1) | 5'-CAT GGT GAAACC CCG TCT CTA-3' |
| Alu Reverse Primer (SEQ ID NO: 2) | 5'-GCC TCA GCC TCC CGA GTA G-3' |
| Alu Probe (SEQ ID NO: 3) | 5'-FAM-ATT AGC CGG GCG TGG TGG CG-TAMRA-3' |
| h/mGAPDH Forward Primer (SEQ ID NO: 4) | 5'-CAG CGA CAC CCA CTC CTC CAC CTT-3' |
| h/mGAPDH Reverse Primer (SEQ ID NO: 5) | 5'-CAT GAG GTC CAC CAC CCT GTT GCT-3' |
| TSG-6 Forward Primer (SEQ ID NO: 6) | 5'-AAG CAC GGT CTG GCA AAT ACA AGC-3' |
| TSG-6 Reverse Primer (SEQ ID NO: 7) | 5'-ATC CAT CCA GCA GCA CAG ACA TGA-3' |
| TSG-6 Probe (SEQ ID NO: 8) | 5'-FAM-TTT GAA GGC GGC CAT CTC GCA ACT T-TAMRA-3' |
| DIDO1 Forward Primer (SEQ ID NO: 9) | 5'-ATG GTT TCA TGG CGA TTG TGT GGG-3' |
| DIDO1 Reverse Primer (SEQ ID NO: 10) | 5'-ACT TGC AGA ATG GTG CAG TTT GGG-3' |
| BMPR2 Forward Primer (SEQ ID NO: 11) | 5'-ACA GAG GTT GGA AAC CAT CCC ACT-3' |
| BMPR2 Reverse Primer (SEQ ID NO: 12) | 5'-AGT GAC CTC ACT GCC AGG CTA TTT-3' |
| SMAD6 Forward Primer (SEQ ID NO: 13) | 5'-ACA AGC CAC TGG ATC TGT CCG ATT-3' |
| SMAD6 Reverse Primer (SEQ ID NO: 14) | 5'-AGA ATT CAC CCG GAG CAG TGA TGA-3' |
| CSF1 Forward Primer (SEQ ID NO: 15) | 5'-TCA GAT GGA GAC CTC GTG CCA AAT-3' |
| CSF1 Reverse Primer (SEQ ID NO: 16) | 5'-TAT CTC TGA AGC GCA TGG TGT CCT-3' |
| VCAM1 Forward Primer (SEQ ID NO: 17) | 5'-TTG CTC AGA TTG GTG ACT CCG TCT-3' |
| VCAM1 Reverse Primer (SEQ ID NO: 18) | 5'-TTC GTC ACC TTC CCA TTC AGT GGA-3' |

Example 11

Supplemental Methods

Data obtained using the following methods are shown in FIGS. 13-18.

A. Preparations:

hMSCs and mouse MSCs from bone marrow were obtained from the Center for the Preparation and Distribution of Adult Stem Cells. The Center has supplied standardized preparations of MSCs enriched for early progenitor cells to over 250 laboratories under the auspices of an NIH/NCRR grant (P40 RR 17447-06). The hMSCs were expanded to passage 3 and 70% confluency and the mouse MSCs cultures as indicated in Example 7-10. Source and conditions for culture of human breast carcinoma cells and fibroblasts are also presented in Examples 7-10.

B. IV Infusion of hMSCs:

Mice were anesthetized, and 150 μl of a suspension of about 1 or $2\times10^6$ hMSCs was infused with a 28 gauge needle either through a tail vein or through the chest wall into the left ventricle. Successful IV infusion was monitored by lack of extravasation at the site and recoveries of about 80% of the Alu sequences in lung within the first hour of infusion (FIG. 13 C). Prior to infusion, the cells were maintained at 4° C. and they were gently re-suspended with a pipette to ensure they were not aggregated before infusion.

C. Isolations of DNA and RNA:

Blood samples of 50 μl were withdrawn with a needle and syringe from the left ventricle of the heart and adjusted to 2 mM EDTA. The mice were then perfused through the left ventricle with 20 ml of PBS and then through the right ventricle with 5 ml of PBS. Brain, heart, lung, liver, pancreas, spleen, kidney tissues and bone marrow were isolated by dissection and stored at −80° C. To extract DNA, the samples were thawed and added to in 5 ml buffer (10 mM Tris HCl, (pH 8.0) containing 20 μl proteinase K (10 mg/ml), 0.1 mM EDTA (pH 8.0), 0.5% SDS and 20 ug/ml RNase A] was added to each sample. The samples were homogenized (PowerGen Model 125 Homogenizer; Fisher Scientific) and incubated in a shaker at 200 rpm and 50° C. overnight. DNA was extracted by mixing 0.5 ml of sample with 0.5 ml phenol/chloroform solution (pH 6.7) and centrifugation at 15,300 g for 5 min in 2 ml phase lock gel tubes (Phase Lock Gel; Eppendorf/Brinkmann Instruments, Inc). DNA was precipitated with half volume of 2.5 M ammonium acetate and same volume of 100% ethanol overnight at 4° C. The precipitates were washed with ice cold 75% ethanol and re-suspended in sterile water. RNA was isolated from the same mouse tissues and from cell cultures using a Trizol (Invitrogen) and cleaned by RNeasy Mini Kit (Qiagen).

D. Real-Time PCR Assays for Alu Sequences:

Because assays by UV absorbance of DNA extracts from several tissues did not provide values accurate enough for the PCR assays, DNA concentration was measured by diphenylamine reaction (BURTON, 1956). Samples of 40 μl were digested for 1 h at 37° C. with 3 μl DNase I (Fisher Scientific) in 5 μl DNase buffer and 2 μl of sterile water. Each sample was diluted with 50 μl of sterile water and 200 μl of a stock solution of diphenylamine reagent was added (1 g diphenylamine (Fisher Scientific) in 100 ml glacial acetic acid (Fisher Scientific) and 2.75 ml $H_2SO_4$ (Sigma)]. The samples were incubated for 21 min at 100° C. and absorbance was measured at 595 nm. Standard curves were prepared with 0.039 to 1.25 mg/ml calf thymus DNA (Sigma).

Real-time PCR assays for Alu sequences (McBride et al., 2003) were performed in a volume of 50 μl that contained 25 μl Taqman Universal PCR Master Mix (Applied Biosystems), 900 nM each of the forward and reverse primers, 250 nM TaqMan probe, and 200 ng target template (See Example 10 for sequences of primers and probes). Reactions were incubated at 50° C. for 2 min and at 95° C. for 10 min followed by 40 cycles at 95° C. for 15 sec and 60° C. for 1 min. Standard curves were generated by adding serial dilutions of hMSCs into mouse tissue samples just prior to homogenization. Real-time PCR assays for human and mouse genes for GAPDH were performed in a volume of 50 μl that contained 25 μl SYBR Green Master Mix (Applied. Biosystems), 200 nM each of the forward and reverse primers and 200 ng target template. All real-time PCR assays were performed in duplicate or triplicate and average values are presented. The final value for total DNA in the sample was corrected by parallel real-time PCR assays with primers that amplified both the human and mouse gene for GAPDH (NCBI home page; Examples 7-10).

E. Real-Time RT-PCR Assays for mRNA for Human GAPDH:

Standard curves were generated by adding serial dilutions of hMSCs to mouse tissue samples just prior to homogenization. About 200 ng of total RNA was used to synthesize double-stranded cDNA by reverse transcription (SuperScript III; Invitrogen). cDNA was analyzed by real time PCR (ABI 7900 Sequence Detector, Applied Biosystems) with human specific GAPDH primers and probe (TaqMan® Gene Expression Assays ID, Hs00266705_g1) using Taqman Universal PCR Master Mix (Applied Biosystems). The final value for total cDNA in the sample was corrected by parallel real-time PCR assays with primers that amplified both the human and mouse gene for GAPDH (see Examples 7-10).

F. Assays of mRNAs in Lung by Microarrays:

RNA was isolated from lungs of mice, assayed on both mouse (MG-430 2.0) and human (HG-U133 Plus 2.0) microarrays (Affymetrix, Santa Clara, Calif.), and the data filtered as described in Examples 7-10.

G. Real Time RT-PCR Analysis for Selected mRNAs:

About 200 ng of total RNA was used to synthesize double-stranded cDNA by reverse transcription (SuperScript III; Invitrogen). cDNA was analyzed by real time PCR using Taqman Universal PCR Master Mix (Applied Biosystems). For the assays, reactions were incubated at 50° C. for 2 min, 95° C. for 10 min, and then 40 cycles at 95° C. for 15 s followed by 60° C. for 1 min. For relative quantitation of gene expression, human specific GAPDH primers and probe (TaqMan® Gene Expression Assays ID, Hs00266705_g1) were used. All other PCR primer and probe sequences were listed in Example 10.

H. Transfections with TSG-6 siRNA:

Target hMSCs for the transfections were prepared with viable passage 1 hMSCs that were plated at 50,000 cells/well in CCM in 6-well plates. After incubation for 1 day, cells were transfected with 10 nM or 20 nM siRNA for TSG-6 (sc-39819; Santa Cruz Biotechnology, Santa Cruz, Calif.) or RNAi negative control (Stealth™ RNAi negative Control; Invitrogen) using a commercial kit (Lipofectamine™ RNAiMAX reagent; Invitrogen). Six hrs later, the medium was replaced with 3 ml per well of CCM lacking antibiotics and hMSCs were incubated for 16 to 20 hrs.

I. TSG-6 ELISA:

TSG-6 protein levels in medium from TNF-α treated MSCs were determined by ELISA. A 96-well plate (Maxisorp™; Nunc) was coated overnight at 4° C. with 50 μl of 10 μg/ml monoclonal antibody specific for TSG-6 (clone A38.1.20; Santa Cruz Biotechnology, Inc.) in 0.2 M sodium bicarbonate buffer (pH 9.2). The plate were washed with PBS and blocked with 0.25% (wt/vol) BSA and 0.05% (vol/vol) Tween-20 in PBS for 30 min at room temperature. Plates were again washed with PBS. Samples of 50 μl or standards of recombinant human TSG-6 protein (R&D Systems) in blocking buffer were added. After 2 hr at room temperature, wells were washed with PBS followed by 50 µl/well of 0.5 µg/ml biotinylated anti-human TSG-6 (TSG-6 Biotinylated PAb Detection Antibody; R&D Systems). After 2 hr, plates were washed with PBS. Fifty pit streptavidin-HRP (R&D Systems) was added to each well. The plate was covered and incubated for 20 min at room temperature. One hundred µL substrate solution (R&D Systems) was added and the sample was incubated for 10 min at room temperature. Absorbance was read at 450 nm (Fluostar Optima; BMG Labtechnologies).

Figure 16A:
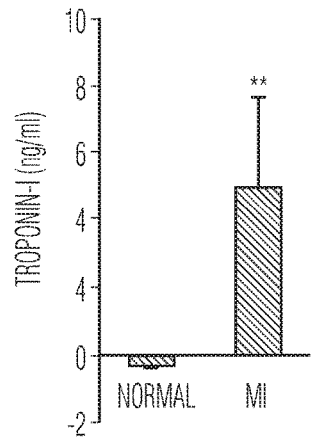
FIG. 16. Assays of Serum and Heart. A. Assay for cardiac troponin I in serum 48 hr after MI. Values are +/−SD;  p<0.01 with n=3 (Normal) or 6 mice (MI) per group. B. Plasmin activity in serum 48 hr after MI. Symbols: Normal, naïve mice; -, MI only; hMSCs, 2×10$^6$ hMSCs infused IV 1 hr after MI; scr siRNA, 2×10$^6$ hMSCs transduced with scrambled siRNA infused IV 1 hr after MI; TSG-6 siRNA, 2×10$^6$ hMSCs transduced with TSG-6 siRNA infused IV 1 hr after MI; rhTSG-6, 30 µg rhTSG-6 protein infused IV 1 hr and again 24 hr after MI. Values are +/−SD;  p<0.01 with n=3 mice per group. N.S.=not significant. C. Hearts assayed for pro- and active-matrix MMP9 on a gelatin zymogen gel 48 hr after MI. Image is reversed. Symbols: as in B. D and E. Granulocyte and monocyte infiltration in the heart 48 hr after MI. Sections stained with anti-Ly-6G and Ly-6C. Symbols: as in B except 100 µg rhTSG-6 protein was infused IV 1 hr and again 24 hr after MI. Magnification ×4. Scale bars, 250 µm. Values are +/−SD; n=3 or 4 for each group. ** p<0.001; N.S.=not significant.
Figure 16B:
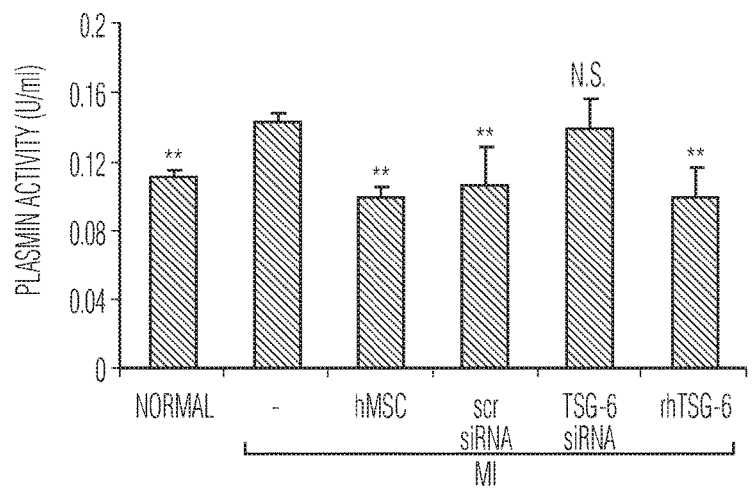

J. Permanent Ligation of the Anterior Descending Coronary Artery (LAD):

Male immunodeficient NOD/scid mice (NOD.CB17-Prkdc$^{scid}$/J; The Jackson Laboratory) 7 to 8 weeks of age were ventilated mechanically under anesthesia with isoflourine, the chest was opened, the left anterior descending coronary artery was ligated, and the chest was closed. The effectiveness of the LAD was established in preliminary experiments by the demonstration that serum cardiac troponin I levels were elevated in 7 mice 48 hr after the surgery (FIG. 16A).

K. Other Assays:

As indicated in Examples 7-10, commercial kits were used to assay mouse cardiac troponin I in serum (ELISA kit; Life Diagnostics, Inc.), plasmin activity in serum (Roche Applied Science) and MMPs in heart by zymography (10% Zymogram Gelatin Gels; Invitrogen/Novex).

L. Leukocyte Infiltration Assay in Heart:

Frozen heart sections of 5 µm from MI-induced mice were stained with anti-Ly-6G and Ly-6C (RB6-8C5, BD Biosciences) and Ly-6G and Ly-6C positive cells were counted with a software program (ImageJ, NIH Image).

M. Microscopic Examination of the Myocardium:

Paraffin-embedded heart samples at 21 days after MI were cut into over 400 sequential 5 µm sections and stained with Masson Trichrome. Quantitative assays for infarct size were performed as described by (Takagawa et al., 2007). In brief, images of every 10$^{th}$ section covering the region of infarct (total of 20 sections per heart) were examined with a spinning disc microscopy (Olympus) using a X4 objective and captured with Stereo Investigator software (Stereo Investigator ver7; MBF Bioscience). Stereological quantification software was used to measure midline infarct length of heart.

N. Echocardiography:

Echocardiography (Acuson Sequoia C512 echocardiography system, Siemens Medical Solutions USA, Inc.) was performed 21 days after MI.

O. Statistical Analyses:

Comparisons between two groups were made with the use of unpaired and two-tailed Student's t-tests. P<0.05 was considered significant.

Example 12

Clearance from Blood and Trapping of Systemically Infused hMSCs

Figure 13A:
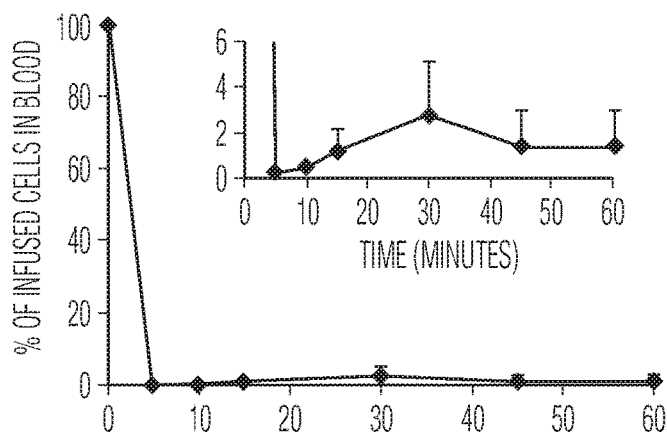
FIG. 13. Assays for Fate of hMSCs Infused into Mice. A. Clearance of human Alu sequences from blood after IV infusion of about $2 \times 10^6$ hMSCs into mice. Values are means+/−S.D; n=6. B. Standard curves for real time PCR assays of human Alu sequences in 7 organs. Values indicate $\Delta\Delta C_t$ for primers for mouse/human GAPDH genes and Alu sequences on same samples. C. Tissue distribution of human Alu sequences 15 min after IV infusion of about $2 \times 10^6$ hMSCs into mice. Values are means+/−S.D; n=6. D. Standard curves for real time RT-PCR assays of human mRNA for GAPDH. Values indicate $\Delta\Delta C_t$ for primers for mouse/human GAPDH genes and cDNA for human specific GAPDH on same samples. E. Kinetics of hMSCs in lung and 6 other tissues after IV infusion of about $2 \times 10^6$ hMSCs. Values are means+/−S.D; n=6. F. Appearance of hMSCs in heart after IV infusion of about $1 \times 10^6$ hMSCs 1 day after permanent ligation of the left anterior descending coronary artery.
Figure 13B:
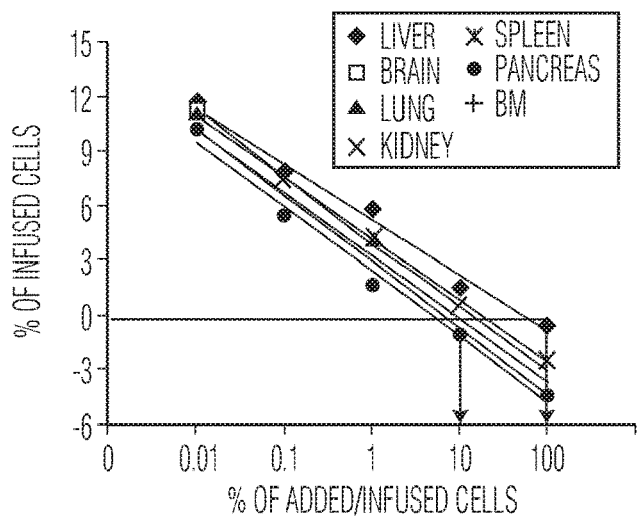
Figure 13C:
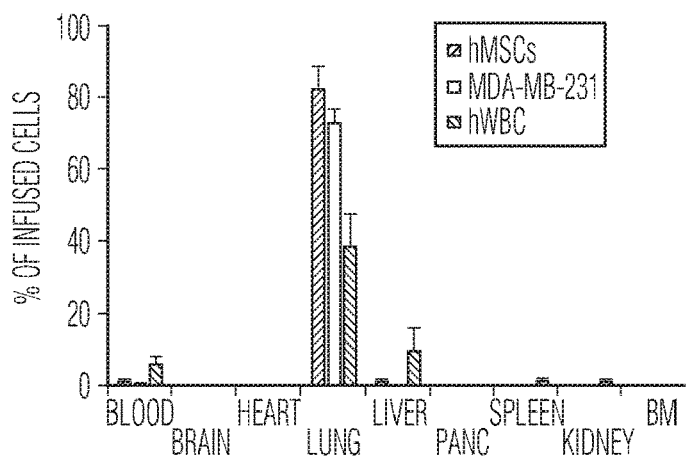

To follow the fate of hMSCs infused IV into mice, the inventors used real time PCR assays for human-specific Alu sequences (McBride et al., 2003). After IV infusion of 2×10$^6$ human MSCs, the Alu assay indicated that 99%+/−1.07 SD of the cells were cleared from the circulation within 5 min (FIG. 13A). From 2 to 3% of the cells (4 to 6×10$^4$) re-appeared in the circulation after a lag period of about 10 min, apparently after release from the lung. To verify that the small number of Alu sequences detected in blood reflected hMSCs, 50 µl of peripheral blood recovered after 15 min was plated on plastic culture dishes in hMSCs medium and incubated for 14 days. The cultures generated typical colonies of spindle-shaped hMSCs that were labeled with antibodies to both human nuclei antigen and human β2-microglobulin (Supplemental FIG. 13). To follow the distribution of the cells in tissues, individual standard curves were developed for each tissue by adding varying numbers of hMSCs to the tissues from naïve mice just before homogenization (FIG. 13B). The use of tissue-specific standard curves minimized variations introduced by differences in yields of extracted DNA, cell numbers of the organs, or efficiencies of the PCR reactions. The sensitivity of the assay was about 100 human cells per mouse organ assayed. To facilitate the assay, a quantitative colorimetric assay for DNA in extracts (BURTON, 1956) was used instead of UV absorbance to select appropriate aliquots for the PCR reactions. As expected (Gao et al., 2001; Schrepfer et al., 2007; Lee et al., 2009), most of the cells cleared from the circulation were trapped in the lung. In mice sacrificed after 15 min, 83%+/−6.3 SD of the human DNA was recovered in lung and only trace amounts were recovered in other tissues (FIG. 13C). Similar results were obtained in control experiments with IV infusions of a line of metastatic breast carcinoma cells (MDA-MB-231 in FIG. 13C). After infusion IV of human white blood cells, a smaller fraction was recovered in lung after 15 min and larger numbers both remained in circulation and appeared in liver (FIG. 13C). The fraction of hMSCs trapped in the lung was not significantly reduced by decreasing the number of infused MSCs to a little as 10,000 in the same volume of vehicle (150 µl), pre-treating the cells with antibodies to integrin-α4 or integrin-α6 (Qian et al., 2006), or pre-incubating the cells with rat white blood cells (Chute, 2006). To examine effects of arterial infusion, 2×10$^6$ hMSCs were infused into the left ventricle of the heart. Most of the cells were again cleared from the blood in 5 min (Supplementary FIG. 14A) but there again was a small re-circulation of about 1.72%+/−1.81 SD of the infused cells for 15 to 60 min (Supplemental FIG. 14A). Also, in comparison to IV infusions, larger numbers of the cells were recovered in organs such as brain, heart, lung, liver and kidney 15 min after the infusions (Supplemental FIG. 14B). Control experiments with breast metastatic cancer cells produced a similar pattern of tissue distribution (Supplemental FIG. 14B).

Figure 13D:
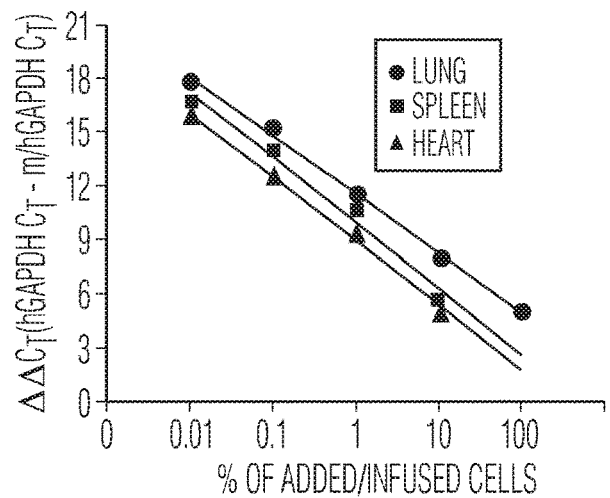

For a semi-quantitative assay for viable cells (Nishida et al., 2006), a similar strategy was used to develop a quantitative RT-PCR assay specific for human GAPDH mRNA (FIG. 13D). The assay had about the same sensitivity as the Alu assay but required more manipulation of the samples. Data developed with the assay indicated that the distribution of Alu sequences largely reflected live cells (FIGS. 13E and F).

Example 13

Kinetics and Redistribution of hMSCs Trapped in Lung

Figure 13E:
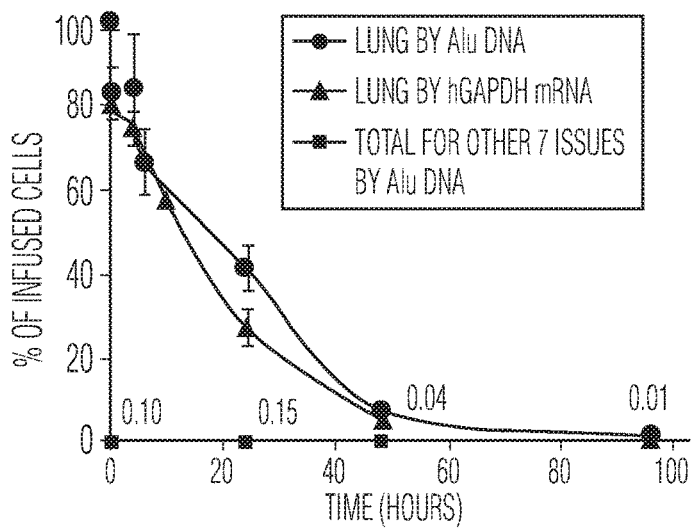

To examine the redistribution with time of the cells from lung, 2×10$^6$ hMSCs were infused IV and 7 tissues of mice were assayed for up to 4 days (FIG. 13E). Assays for Alu sequences indicated that the cells initially trapped in lung disappeared with a half-life of about 24 hr. Similar values were obtained by assays for viable human cells by the levels of human mRNA for GAPDH (FIG. 13E). Histological sections of lung demonstrated that the human MSCs trapped in lung formed emboli in afferent blood vessels (Lee et al., 2009) with many of the cells undergoing apoptosis (not shown). The cells that disappeared from lung did not appear in any significant numbers in the 6 other tissues: a total of 0.04% of the infused Alu sequences (equivalent to about 4,000 cells) were recovered in the 6 tissues after 48 hr and 0.01% after 96 hr (FIG. 13E).

Example 14

Trapping of hMSCs in Infarcted Heart

Figure 13F:
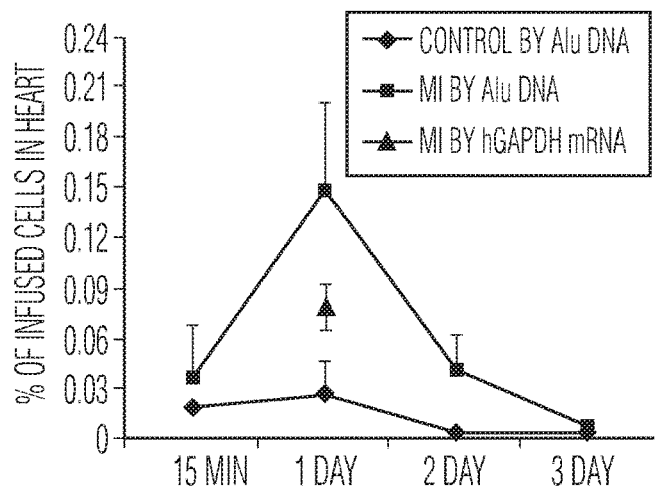

To determine whether larger numbers of IV infused hMSCs appeared in the heart after MI, hMSCs were infused into the tail veins for NOD/scid mice 1 day after MIs were produced by permanent ligation of the anterior descending coronary artery (LAD). Assays for Alu sequences indicated that 0.04%+/−0.03 SD of the infused cells (400 cells+/−300 SD; n=5) were recovered in the infracted hearts 15 min after the infusion (FIG. 13F). One day after IV infusions, the Alu sequences in heart increased about 5-fold to 0.148%+/−0.053 SD, equivalent to about 1,480 cells+/−530 SD (n=5). Similar values were obtained by assays for human GAPDH mRNA (792 cells+/−140 SD; n=5) 1 day after the infusions.

Example 15

Changes in the Mouse and Human Transcriptome Produced by Embolization

Figure 14A:
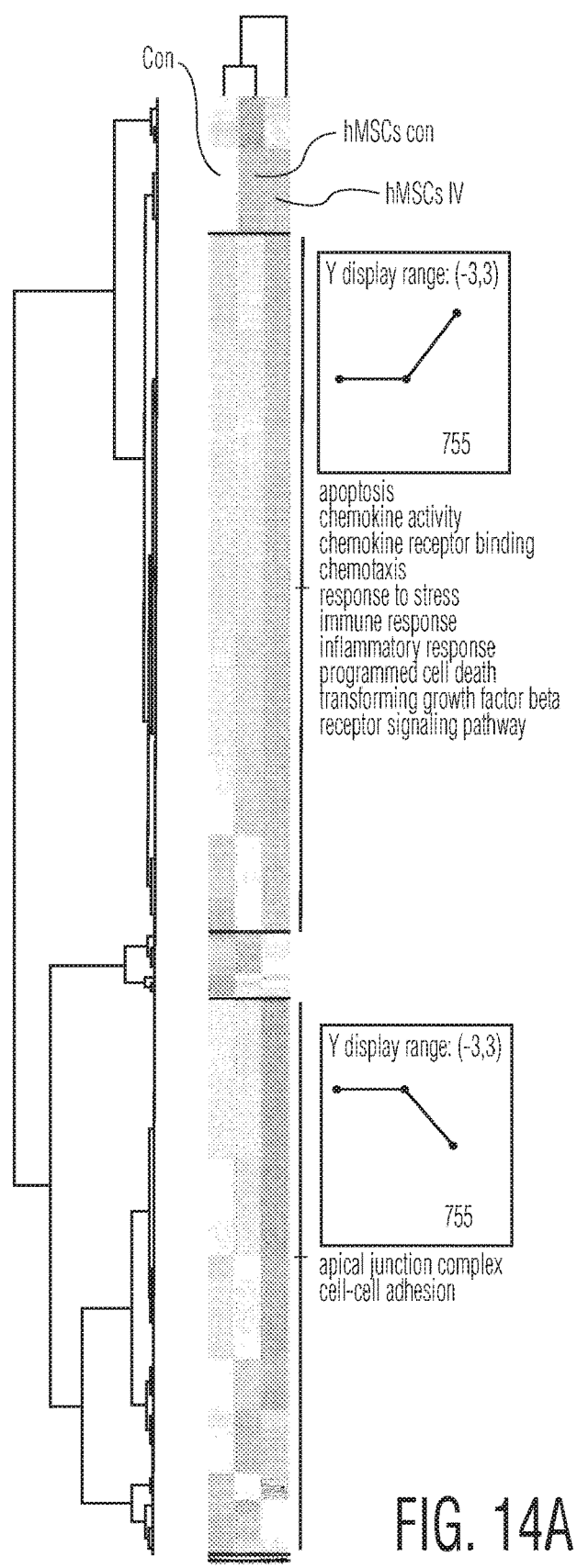
FIG. 14. Heat Map of Microarray Assays of Mouse Lungs after IV Infusion of hMSCs. About $2 \times 10^6$ hMSCs were infused IV and lung RNA was recovered 10 hr later for assays on both mouse-specific and human-specific microarrays (Affymetrix, Santa Clara, Calif.). Data were filtered for cross-hybridization (CV>0.5 and call >33%), analyzed with the Microarray Suite 5.0 program, and normalized to a value of 1 and variance of 3 SD (+3, red; 3, blue). Gene ontology categories of genes are indicated. The number of genes with expression differences is indicated in the boxes. A. Assay on mouse specific chip. B. Assay of same RNA on human specific chip. Symbols: con, lung from control mouse; hMSCs con, sample of hMSCs added to lung from control mouse before extraction of RNA; hMSCs IV, sample from mouse lung 10 hr after IV infusion of hMSCs.
Figure 14B:
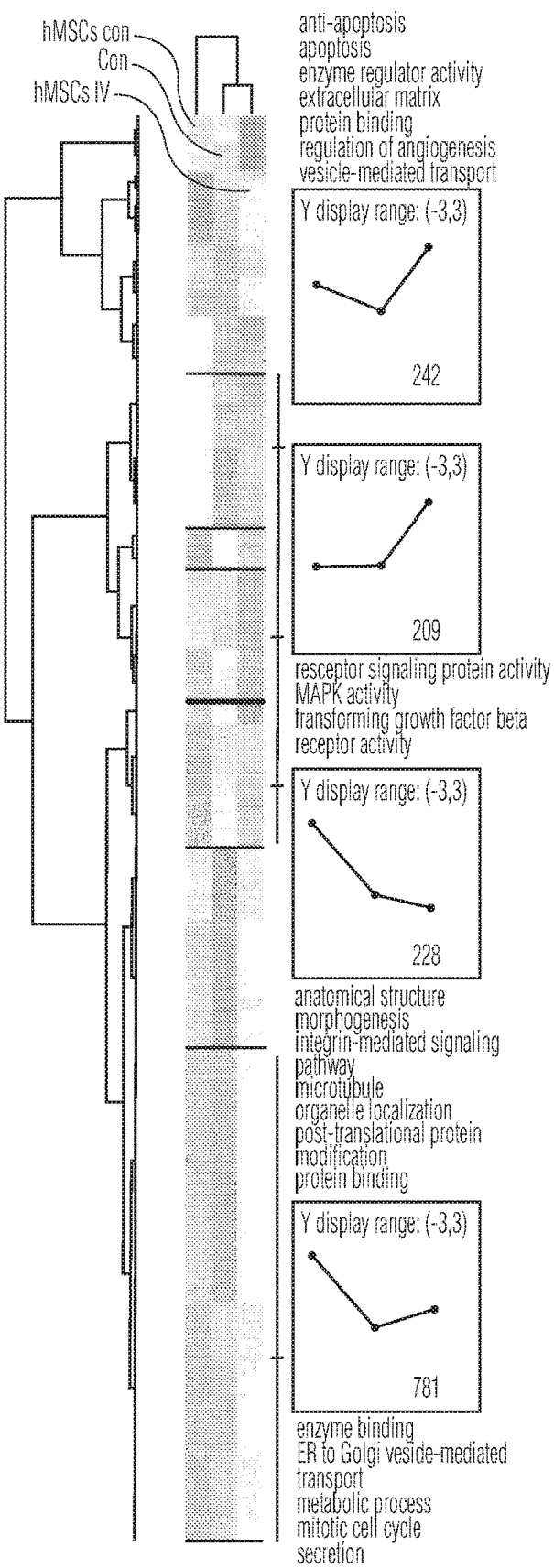

To assay both transcriptomes, about $2 \times 10^6$ hMSCs were infused into the tail veins of mice and RNA was extracted from lung 10 hr later, a time at which assays for human GAPDH mRNA indicated there were adequate amounts of human mRNA for assays (FIG. 13E). After filtering for cross-hybridization with human mRNA (see Supplemental Materials), the data indicated that embolization with the hMSCs up-regulated expression of 755 mouse transcripts and down-regulated expression of 347 mouse transcripts 2-fold or more (FIG. 14A). Also, the data indicated that after embolization in lung, 451 human transcripts were up-regulated and 1,009 transcripts were down-regulated (FIG. 14B).

Figure 15A:
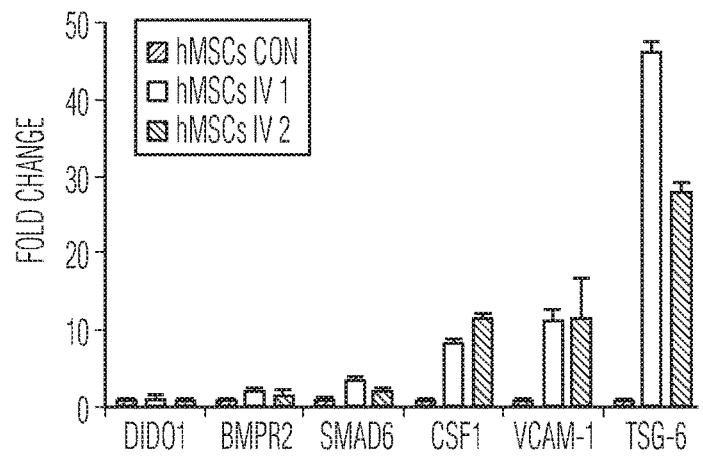
FIG. 15. Activation of hMSCs to Express TSG-6. A. Real-time RT-PCR assays for human-specific mRNAs in lung 10 hr after IV infusion of $2 \times 10^6$ hMSCs. Values are fold increase over values for cultured hMSCs, normalized by $\Delta\Delta C_t$ for hGAPDH. Symbols: hMSCs con, sample of hMSCs added to lung from control mouse before extraction of RNA; hMSCs IV 1 and 2, samples from lungs of 2 mice 10 hr after IV infusion of hMSCs. B. Real-time RT-PCR assays for human TSG-6 in mouse lung. About $2 \times 10^6$ hMSCs were infused IV into naïve mice (IV-nor) or mice at 1 h after MI (IV-MI) and lungs were recovered 0.25 hr to 24 hr after the infusions. Values are +/−SD; n=2 or 3 for normal mice; n=6 for MI mice. C. Real-time RT-PCR assays for TSG-6 in hMSCs and human fibroblasts from the same donor incubated in serum-free medium with 10 ng/ml TNF-α for 24 or 48 hr. Results with two passages of the same cells are shown. Values are +/−SD; n=3. D. ELISA assays for TSG-6 in medium from hMSCs and human fibroblasts incubated in serum-free medium with 10 ng/ml TNF-α for 48 hr. Values are +/−SD; n=3. E. Real-time RT-PCR assays TSG-6 of control hMSCs (Con), hMSCs treated with transfection reagents only (no siRNA), hMSCs transfected with a scrambled siRNA (scr siRNA) or hMSCs transduced with TSG-6 siRNA (TSG-6 siRNA). Cells were incubated with or without 10 ng/ml TNF-α for 6 hr. Values are +/−SD; n=3. F. ELISA assays for TSG-6 in medium after incubation of cells with or without TNF-α for 48 hr. Symbols: as in E. Values are +/−SD; n=3.

The up-regulated 451 human transcripts were subjectively examined for candidate genes of interest and human-specific real-time RT-PCR assays were used to confirm the microarray data (FIG. 15A). The results confirmed 2-fold or greater increases in the transcripts for SMAD6, CSF1, VCAM-1 and TNFAIP6 (TSG-6). The increases in TSG-6 were 28-fold and 47-fold or considerably larger than the 7.5-fold increase detected by the microarrays (Supplemental Table 1). As recently reported (Ylostalo et al., 2008), real-time RT-PCR assays frequently demonstrated larger changes in transcripts than microarray assays with the system employed here.

Example 16

MSCs In Vitro are Activated to Secret TSG-6

Figure 15B:
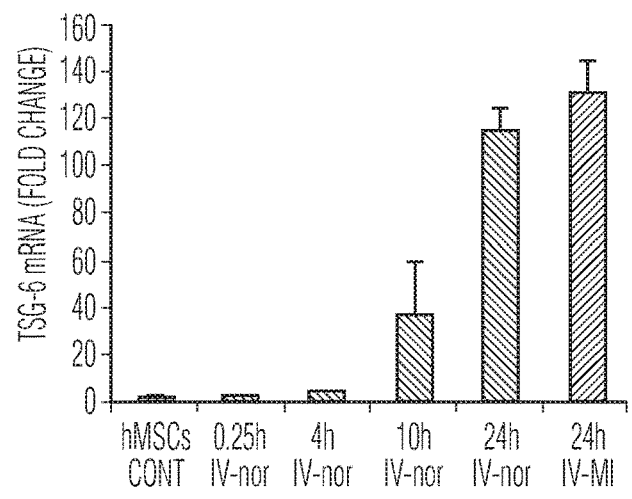
Figure 15C:
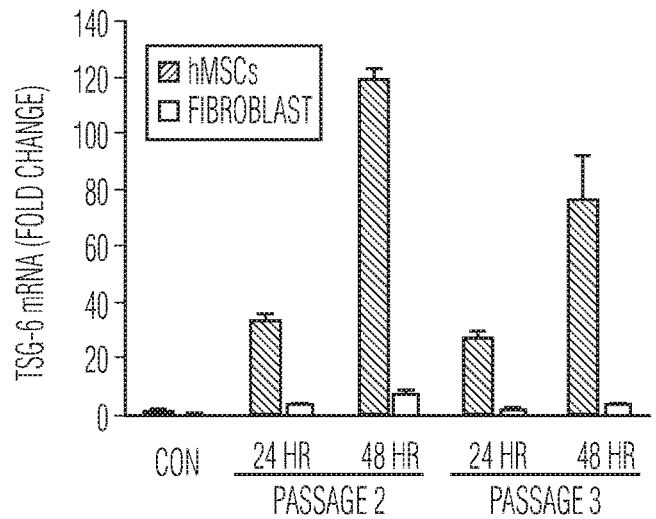
Figure 15D:
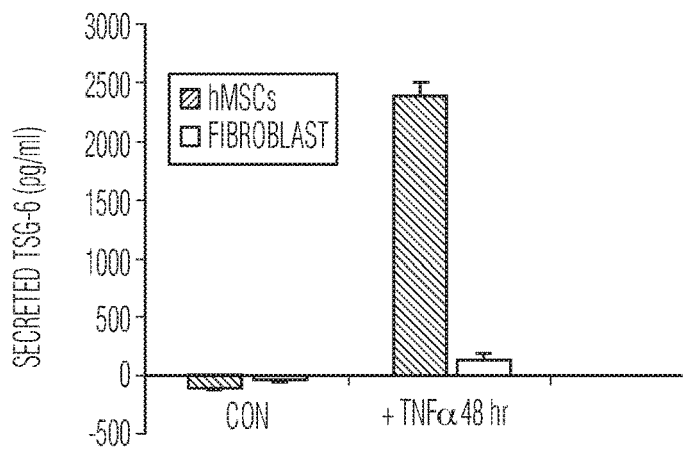

The increase in TSG-6 was of particular interest because the protein was previously shown to be a powerful anti-inflammatory factor (Forteza et al., 2007; Getting et al., 2002; Wisniewski and Vilcek, 2004; Milner et al., 2006). Real-time RT-PCR assays demonstrated that human TSG-6 mRNA in lung was increased at 10 hr and further increased at 24 hr after IV infusions of hMSCs (FIG. 15B). There was no difference in expression of TSG-6 in lungs from naïve mice and mice with MIs (FIG. 15B). TSG-6 was discovered by analysis of cDNA clones from skin fibroblasts that were incubated with TNF-α (Lee et al., 1992). Therefore, hMSCs and fibroblasts from same donor were incubated with TNF-α and the mRNAs were assayed by real-time RT-PCR. The transcript for TSG-6 in hMSCs was increased about 120-fold after incubation with 10 ng/ml TNF-α for 48 hr and increased about 80-fold with a further passage of the hMSCs (FIG. 15C). ELISAs indicated that incubation with TNF-α for 48 hr increased the secretion of TSG-6 protein from undetectable levels to over 2,000 pg/ml/$10^5$ cells/48 hr (FIG. 15D). Surprisingly, the response of hMSCs to TNF-α far exceeded the response of human fibroblasts. In parallel experiments, mouse MSCs incubated with TNF-α under the same conditions up-regulated expression of the transcript for TSG-6 3.94-fold (+/−0.49 SD; n=4).

Transient transduction of hMSCs with TSG-6 siRNA abrogated the effects of TNF-α on TSG-6 transcription (FIG. 15E) and secretion (FIG. 3F). Expression of TSG-6 was partially reduced by a mock transduction or transduction with a scrambled siRNA.

Example 17

Both IV MSCs and rhTSG-6 Decrease Pro-Inflammatory Proteases in Mice with MI

Acute MI produces an acute inflammatory response in which infiltrating neutrophils generate MMPs that degrade the myocardium (Fang et al., 2007; Lindsey et al., 2001). The permanent LAD increased serum levels of both cardiac troponin I (FIG. 16A), a biomarker for myocardial injury (Chapelle, 1998; Pervaiz et al., 1997), and plasmin activity (FIG. 16B), a marker for inflammatory responses (Heymans et al., 1999; Griffin et al., 2005). The plasmin activity was decreased by two infusions of rhTSG-6, an observation consistent with its known inhibitory effects (Bardos et al., 2001; Milner et al., 2006). The plasmin activity was also decreased by IV infusion of hMSCs and hMSCs with a scrambled siRNA but not hMSCs transduced with siRNA for TSG-6.

Figure 16C:
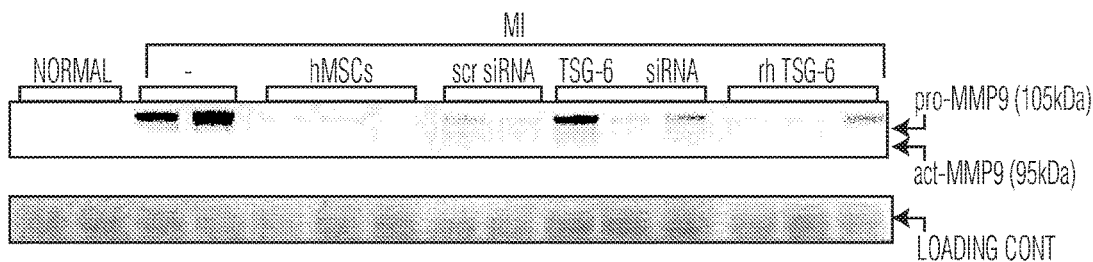
Figure 16D:
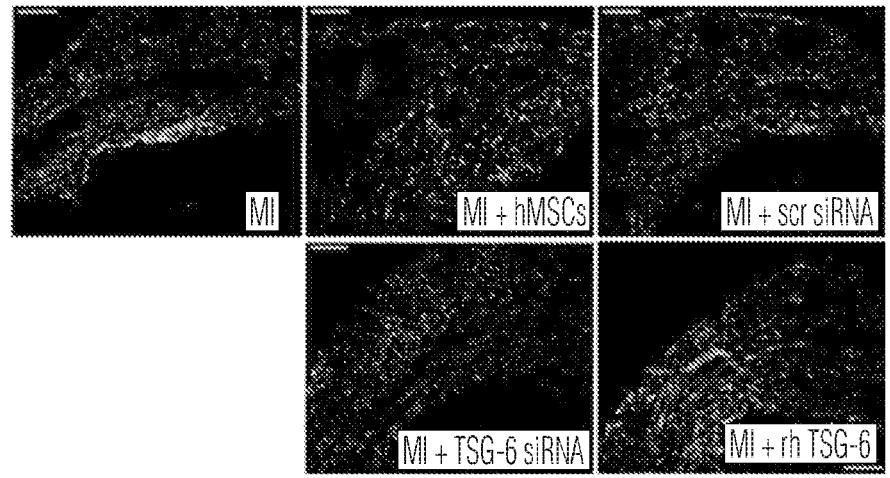
Figure 16E:
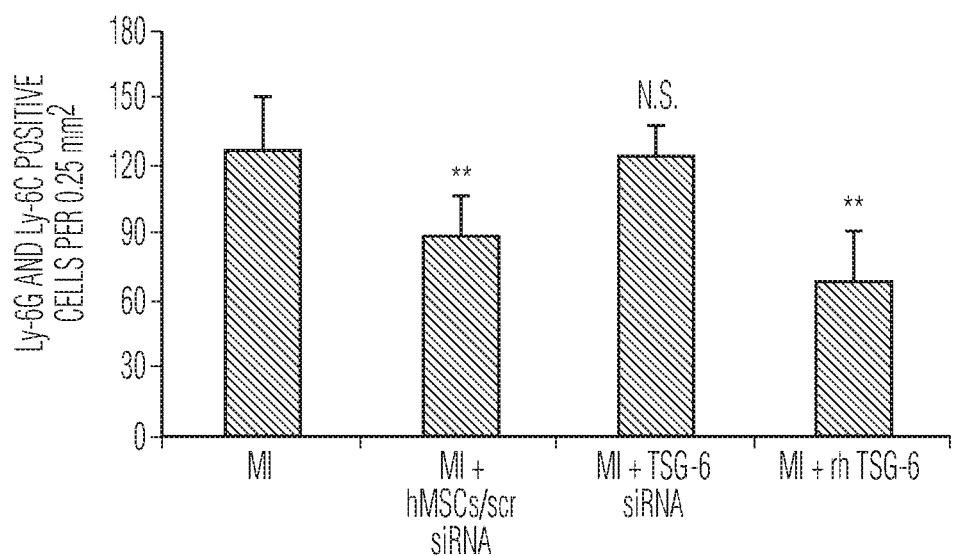

As expected (Fang et al., 2007), the enzymic activities of both pro-MMP9 and active MMP9 were increased in heart 2 days after MI (FIG. 16C). IV infusion of hMSCs or hMSCs transduced with a scrambled siRNA decreased both activities (FIG. 16C). The effects of hMSCs were partially negated by knock down of the TSG-6 gene prior to infusion of the cells. Also, the effects of hMSCs were partially duplicated by the two infusions of human recombinant TSG-6. The decreases in pro-MMP activities were reflected in decreases in granulocyte and monocyte infiltration in the heart (FIGS. 16D and E).

Example 18

Effects of TSG-6 on Infarct Size and Heart Function in MI

Figure 15E:
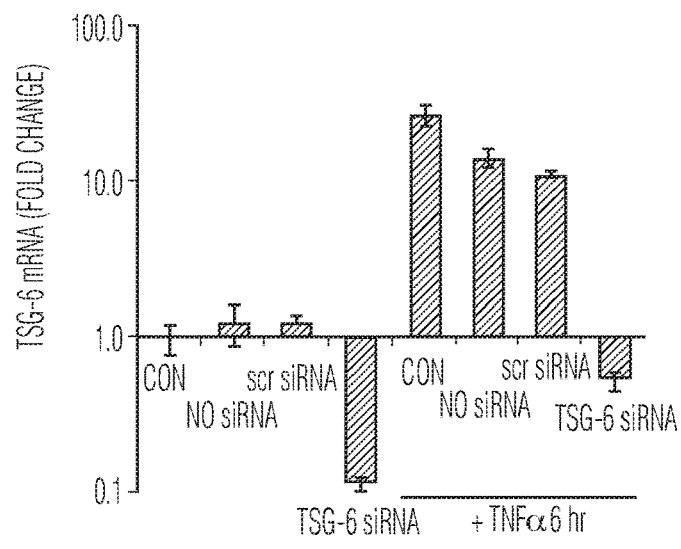
Figure 15F:
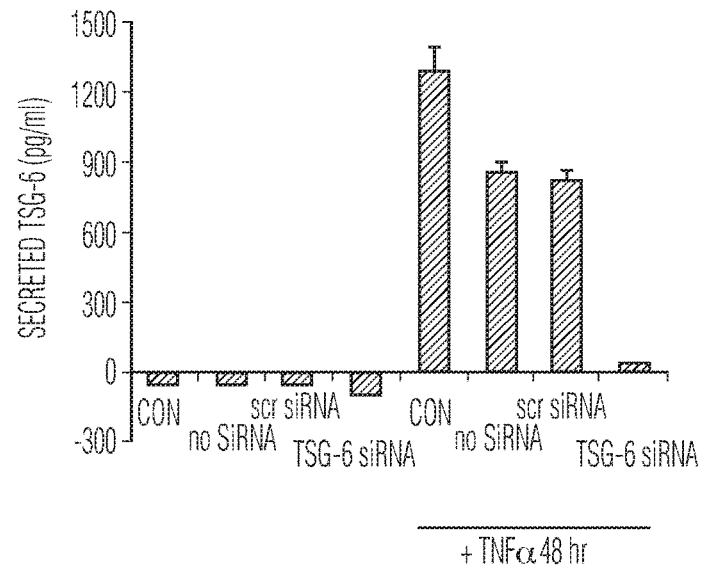
Figure 17A:
FIG. 17. Assays of Infarct Size. Each heart was cut from the apex through base into over 400 sequential 5 um sections and stained with Masson Trichrome. Every 20$^{th}$ section is shown. Additional heart samples shown in FIG. 12. A. to E. Symbols as in FIG. 16B except 100 µg rhTSG-6 protein was infused IV 1 hr and again 24 hr after MI. F. Infarct size measurements (%) obtained by midline length measurement from 10$^{th}$ section of the infarct area for a total of 20 sections per heart (Takagawa et al., 2007). Values are +/−SD; n=3 or 4 mice in each group; ***p<0.0001 compared to MI controls; N.S.=not significant compared to MI controls; * p<0.05 for MI+MSCs versus MI+rhTSG-6.
Figure 17B:
Figure 17C:
Figure 17D:
Figure 17E:
Figure 17F:
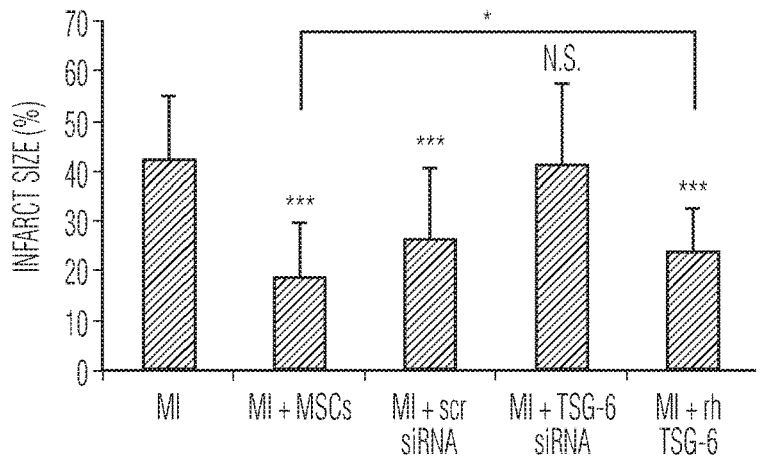

As reported previously (Iso et al., 2007), IV infusion of hMSCs decreased infarct size examined 3 wk after MI (FIGS. 17A, B and F and FIG. 12). hMSCs with an siRNA knock down of the TSG-6 gene had no effect on infarct size (FIGS. 17D and F). hMSCs transduced with the scrambled siRNA produced an intermediate effect on infarct size (FIGS. 17C and F), apparently because the scrambled siRNA had a partial effect on TSG-6 secretion (FIGS. 15E and F). In addition, IV infusion of 100 µg of rhTSG-6 immediately following the surgery and at 24 hr also decreased infarct size (FIGS. 17E and F and FIG. 12). However, the effect the rhTSG-6 was somewhat less than the decrease in infarct size following administration of the hMSCs (p<0.05).

Figure 18A:
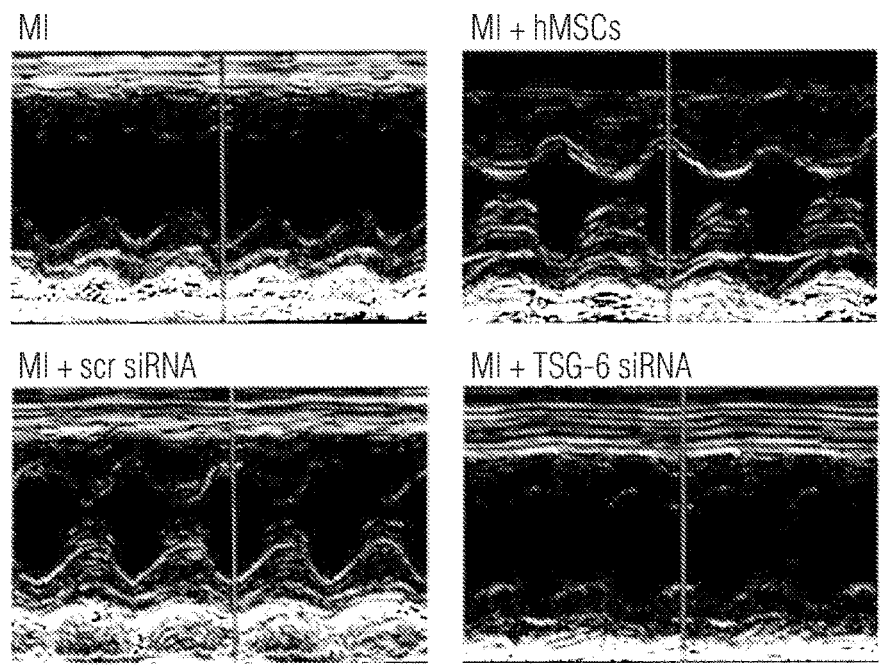
FIG. 18. Echocardiographic Assays 3 Wk after MI. A. Representative M-mode echocardiograms. Symbols: as in FIG. 16B. B. Left ventricular fractional shortening (LVFS) and left ventricular ejection fraction (LVEF) from echocardiographic data. Values are +/−SD; n=5 or 6 for each group; *p<0.05 versus MI; N.S.=not significant.
Figure 18B:
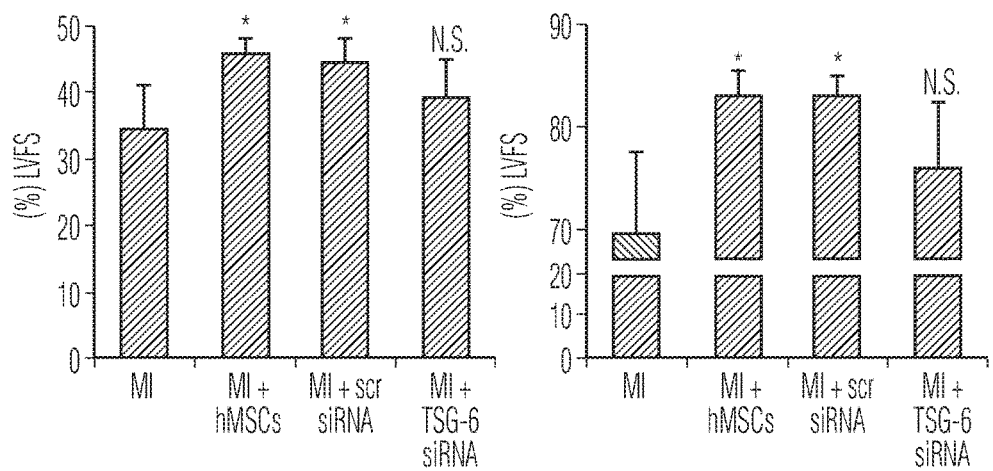

Assays by echocardiography demonstrated comparable effects on heart function. IV infusions of $2 \times 10^6$ hMSCs or hMSCs with a scrambled siRNA 1 hr after MI produced significant improvements in % left ventricular fractional shortening and left ventricular ejection fraction in hearts assayed 3 wk later (FIG. 18 and Table 3). Infusions of hMSCs with a knock-down of TSG-6 had no effect.

REFERENCES

The following references, to the extent that they provide exemplary procedural or other details supplementary to those set forth herein, are specifically incorporated herein by reference: Aggarwal S, Pittenger M F. (2005) Human mesenchymal stem cells modulate allogeneic immune cell responses. Blood 105, 1815-1822; Akiyama Y, Radtke C, Honmou O, Kocsis J D. (2002). Remyelination of the spinal cord following intravenous delivery of bone marrow cells. Glia.; 39:229-236; Anjos-Afonso F, Bonnet D. (2007) Non-hematopoietic/endothelial SSEA-1+ cells define the most primitive progenitors in the adult murine bone marrow mesenchymal compartment. Blood; 109:1298-1306; Barbash, I M, P Chouraqui, J Baron, M S Feinberg, S Etzion, A Tessone, L Miller, E Guetta, D Zipori, L H Kedes, R A Kloner, J Leor, 2003, Systemic delivery of bone marrow-derived mesenchymal stem cells to the infarcted myocardium: feasibility, cell migration, and body distribution: Circulation, v. 108, p. 863-868; Battula V L, Bareiss P M, Treml S, Conrad S, Albert I, Hojak S, Abele H, Schewe B, Just L, Skutella T, Bühring H J. (2007) Human placenta and bone marrow derived MSC cultured in serum-free, b-FGF-containing medium express cell surface frizzled-9 and SSEA-4 and give rise to multilineage differentiation. Differentiation 75:279-291; Burt R K, Loh Y, Pearce W, Beohar N, Barr W G, Craig R, Wen Y, Rapp J A, Kessler J. Clinical applications of blood-derived and marrow-derived stem cells for nonmalignant diseases. JAMA. 2008 Feb. 27; 299(8):925-36; Caplan A I, Dennis J E. (2006) Mesenchymal stem cells as trophic mediators. J Cell Biochem 98(5): 1076-84; Caplan A I. (2005) Review: mesenchymal stem cells: cell-based reconstructive therapy in orthopedics. Tissue Eng. July-August; 11(7-8):1198-211; Caplan A I. (1990) Review. Stem cell delivery vehicle. Biomaterials. July; 11:44-6; Castro-Malaspina H, Gay R E, Resnick G, Kapoor N, Meyers P, Chiarieri D, McKenzie S, Broxmeyer H E, Moore M A. (1980) Characterization of human bone marrow fibroblast colony-forming cells (CFU-F) and their progeny. Blood. August; 56(2):289-301; Charwat S, Gyöngyösi M, Lang I, Graf S, Beran G, Hemetsberger R, Nyolczas N, Sochor H, Glogar D. Role of adult bone marrow stem cells in the repair of ischemic myocardium: Current state of the art. Exp Hematol. 2008 June; 36(6):672-80. Epub 2008 Mar. 20; Chen J, Li Y, Katakowski M, Chen X, Wang L, Lu D, Lu M, Gautam S C, Chopp M. (2003) Intravenous bone marrow stromal cell therapy reduces apoptosis and promotes endogenous cell proliferation after stroke in female rat. J Neurosci Res. September 15; 73(6):778-86; Colter D C, Sekiya I, Prockop D J. (2001) Identification of a subpopulation of rapidly self renewing and multipotential adult stem cells in colonies of human marrow stromal cells. Proc Natl Acad Sci USA. 98:7841-7845; De Bari C, Dell'Accio F, Vandenabeele F, Vermeesch J R, Raymackers J M, Luyten F P. (2003) Skeletal muscle repair by adult human mesenchymal stem cells from synovial membrane. J Cell Biol. March 17; 160(6):909-18; Deng W, Obrocka M, Fischer I, Prockop D J. (2001) In vitro differentiation of human marrow stromal cells into early progenitors of neural cells by conditions that increase intracellular cyclic AMP. Biochem Biophys Res Commun. March 23; 282(1):148-52; Dimmeler S, Burchfield J, Zeiher A M. Arterioscler Thromb Vasc Biol. 2008 February; 28(2):208-16. Epub 2007 Oct. 19; Dimmeler S & Leri A. Aging and disease as modifiers of efficacy of cell therapy. Circ Res. 2008 Jun. 6; 102(11):1319-30; Dooner M, Cerny J, Colvin G, Demers D, Pimentel J, Greer D, Abedi M, McAuliffe C, Quesenberry P. (2004) Homing and conversion of murine hematopoietic stem cells to lung. Blood Cells Mol Dis.; 32:47-51; Eaves C, Glimm H, Eisterer W, Audet J, Maguer-Satta V, Piret J. (2001) Characterization of human hematopoietic cells with short-lived in vivo repopulating activity. Ann N.Y. Acad Sci. June; 938:63-70; Forteza R, Casalino-Matsuda S M, Monzon M E, Fries E, Rugg M S, Milner C M, Day A J. TSG-6 potentiates the antitissue kallikrein activity of inter-alpha-inhibitor through bikunin release. Am J Respir Cell Mol Biol. 2007 January; 36(1): 20-31; Fukuda K, Yuasa S. (2006) Stem cells as a source of regenerative cardiomyocytes. Circ. Res. 98:1002-1013; Furness S G, McNagny K. (2006) Beyond mere markers: functions for CD34 family of sialomucins in hematopoiesis. Immunol Res.; 34:13-32; Gang E J, Bosnakovski D, Figueiredo C A, Visser J W, Perlingeiro R C. (2007) SSEA-4 identifies mesenchymal stem cells from bone marrow. Blood; 109:1743-1751; Gao J, Dennis J E, Muzic R F, Lundberg M, Caplan A I. (2001) The dynamic in vivo distribution of bone marrow-derived mesenchymal stem cells after infusion. Cells Tissues Organs; 169:12-20; Gao J, J E Dennis, R F Muzic, M Lundberg, A I Caplan, 2001b, The dynamic in vivo distribution of bone marrow-derived mesenchymal stem cells after infusion: Cells Tissues. Organs, v. 169, p. 12-20; Getting S J, Mahoney D J, Cao T, Rugg M S, Fries E, Milner C M, Perretti M, Day A J. The link module from human TSG-6 inhibits neutrophil migration in a hyaluronan- and inter-alpha-inhibitor-independent manner. J Biol Chem. 2002 Dec. 27; 277(52):51068-76; Gerdoni E, Gallo B, Casazza S, Musio S, Bonanni I, Pedemonte E, Mantegazza R, Frassoni F, Mancardi G, Pedotti R, Uccelli A. (2007) Mesenchymal stem cells effectively modulate pathogenic immune response in experimental autoimmune encephalomyelitis. Ann Neurol. Machr; 61(3):219-27; Gregory C A, Ylostalo J, Prockop D J. (2005) Adult bone marrow stem/progenitor cells (MSCs) are preconditioned by microenvironmental "niches" in culture: a two-stage hypothesis for regulation of MSC fate. Sci STKE. July 26 (294) pe37; Gronthos S, Zannettino A C, Hay S J, Shi S, Graves S E, Kortesidis A, Simmons P J. (2003) Molecular and cellular characterisation of highly purified stromal stem cells derived from human bone marrow. J Cell Sci.; 116: 1827-1835; Guilak F, Awad H A, Fermor B, Leddy H A, Gimble J M. (2004) Adipose-derived adult stem cells for cartilage tissue engineering. Biorheology. 41(3-4):389-99; Gupta N, Su X, Popov B, Lee J W, Serikov V, Matthay M A. Intrapulmonary delivery of bone marrow-derived mesenchymal stem cells improves survival and attenuates endotoxin-induced acute lung injury in mice. J Immunol. 2007 Aug. 1; 179(3):1855-63; Haynesworth S E, Baber M A, Caplan A I. (1992) Cell surface antigens on human marrow derived mesenchymal cells are detected by monoclonal antibodies. Bone; 13:69-80; Hogg J C, Coxson H O, Brumwell M L, Beyers N, Doerschuk C M, MacNee W, Wiggs B R. (1994) Erythrocyte and polymorphonuclear cell transit time and concentration in human pulmonary capillaries. J Appl Physiol.; 77:1795-1800; Horwitz E M, Gordon P L, Koo W K, Marx J C, Neel M D, McNall R Y, Muul L, Hofmann T. (2002) Isolated allogeneic bone marrow-derived mesenchymal cells engraft and stimulate growth in children with osteogenesis imperfecta: Implications for cell therapy of bone. Proc Natl Acad Sci USA 99:8932-8937; Horwitz E M, Prockop D J, Fitzpatrick L A, Koo W W, Gordon P L, Neel M, Sussman M, Orchard P, Marx J C, Pyeritz R E, Brenner M K. (1999) Transplantability and therapeutic effects of bone marrow-derived mesenchymal cells in children with osteogenesis imperfecta. Nat Med.; 5:309-313; Iso Y, Spees J L, Serrano C, Bakondi B, Pochampally R, Song Y H, Sobel B E, Delafontaine P, Prockop D J. (2007) Multipotent human stromal cells improve cardiac function after myocardial infarction in mice without long-term engraftment.

Biochem. Biophys. Res. Commun. 354:700-706; Kim S, Honmou O, Kato K, Nonaka T, Houkin K, Hamada H, Kocsis J D. (2006) Neural differentiation potential of peripheral blood- and bone-marrow-derived precursor cells. Brain Res. December 6; 1123(1):27-33; Koc O N, Day J, Nieder M et al. (2002) Allogeneic mesenchymal stem cell infusion for treatment of metachromatic leukodystrophy (MLD) and Hurler syndrome (MPS-IH). Bone Marrow Transplant. 30:215-222; Krampera M, Marconi S, Pasini A, Galiè M, Rigotti G, Mosna F, Tinelli M, Lovato L, Anghileri E, Andreini A, Pizzolo G, Sbarbati A, Bonetti B. (2007) Induction of neural-like differentiation in human mesenchymal stem cells derived from bone marrow, fat, spleen and thymus. Bone. February; 40(2):382-90; Kuznetsov S A, Mankani M H, Gronthos S, Satomura K, Bianco P, Robey P G. (2001) Circulating skeletal stem cells. J Cell Biol. May 28; 153(5):1133-40; Le Blanc K, Ringdén O. (2007) Immunomodulation by mesenchymal stem cells and clinical experience. J Intern Med. November; 262(5):509-25; Lee R H, Seo M J, Reger R L, Spees J L, Pulin A A, Olson S D, Prockop D J. (2006a) Multipotent stromal cells from human marrow home to and promote repair of pancreatic islets and renal glomeruli in diabetic NOD/scid mice. *Proc Natl Acad Sci USA* 103:17438-17443; Lipscomb E A, Mercurio A M. (2005) Mobilization and activation of a signaling competent alpha6beta4integrin underlies its contribution to carcinoma progression. Cancer Metastasis Rev.; 24:413-423; MacDonald I C, Groom A C, Chambers A F. (2002) Cancer spread and micrometastasis development: quantitative approaches for in vivo models. Bioessays.; 24:885-893; Mareschi K, Novara M, Rustichelli D, Ferrero I, Guido D, Carbone E, Medico E, Madon E, Vercelli A, Fagioli F. (2006) Neural differentiation of human mesenchymal stem cells: Evidence for expression of neural markers and eag K+ channel types. Exp Hematol. November; 34(11):1563-72; Martinez C, Hofmann T J, Marino R, Dominici M, Horwitz E M. (2007) Human bone marrow mesenchymal stromal cells express the neural ganglioside GD2: a novel surface marker for the identification of MSCs. Blood. 109:4245-4248; McGeer E G, McGeer P L. The role of anti-inflammatory agents in Parkinson's disease. CNS Drugs. 2007; 21(10):789-97; Mets T, Verdonk G. (1981) In vitro aging of human bone marrow derived stromal cells. Mech Ageing Dev. 16:81-89; Milner C M, Higman V A, Day A J (2006). "TSG-6: a pluripotent inflammatory mediator?". *Biochem. Soc. Trans.* 34 (Pt 3): 446-50; Mishra P K. (2008) Bone marrow-derived mesenchymal stem cells for treatment of heart failure: is it all paracrine actions and immunomodulation? J Cardiovasc Med (Hagerstown). February; 9(2):122-128; Muñoz J R, Stoutenger B R, Robinson A P, Spees J L, Prockop D J (2005) Human stem/progenitor cells from bone marrow promote neurogenesis of endogenous neural stem cells in the hippocampus of mice. Proc. Natl. Acad. Sci. U.S.A. 102, 18171-18176; Nomura T, Honmou O, Harada K, Houkin K, Hamada H, Kocsis J D. (2005) I.V. infusion of brain-derived neurotrophic factor gene-modified human mesenchymal stem cells protects against injury in a cerebral ischemia model in adult rat. Neuroscience 136(1):161-9; Ohtaki H, Ylostalo J, Foraker J E, Robinson A P, Reger R L, Shioda S, & Prockop D J (2008) Human stem/progenitor cells from bone marrow (hMSCs) decrease neural cell death in transient global ischemia by modulation of the inflammatory and immune responses. Proceedings of the National Academy of Sciences, in press; Owen M, Friedenstein A J. (1988) Stromal stem cells: marrow-derived osteogenic precursors. Ciba Found. Symp. 136:42-60; Ortiz L A, Dutreil M, Fattman C, Pandey A C, Torres G, Go K, Phinney D G. (2007) Interleukin 1 receptor antagonist mediates the antiinflammatory and antifibrotic effect of mesenchymal stem cells during lung injury. Proc Natl Acad Sci USA. 104:11002-7; Pereira R F, O'Hara M D, Laptev A V, Halford K W, Pollard M D, Class R, Simon D, Livezey K, Prockop D J. (1998) Marrow stromal cells as a source of progenitor cells for nonhematopoietic tissues in transgenic mice with a phenotype of osteogenesis imperfecta. Proc Natl Acad Sci USA 95:1142-1147; Penolazzi L, Lambertini E, Tavanti E, Torreggiani E, Vesce F, Gambari R, Piva R. (2007) Evaluation of chemokine and cytokine profiles in osteoblast progenitors from umbilical cord blood stem cells by BIO-PLEX technology. Cell Biol Int. September 7; (Epub ahead of print]; Piersma A H, Ploemacher R E, Brockbank K G. (1983) Transplantation of bone marrow fibroblastoid stromal cells in mice via the intravenous route. Br J Haematol. June; 54(2):285-90; Pochampally R R, Smith J R, Ylostalo J, Prockop D J. Serum deprivation of human marrow stromal cells (hMSCs) selects for a sub-population of early progenitor cells with enhanced expression of Oct-4 and other embryonic genes. Blood 103: 1647-1652 (2004); Prockop D J. (2007) "Stemness" does not explain the repair of many tissues bymesenchymal stem/multipotent stromal cells (MSCs). Clinical Pharmacology and Therapeutics 82:241-243; Prockop D J, Gregory C A, Spees J L. (2003) One strategy for cell and gene therapy: harnessing the power of adult stem cells to repair tissues. Proc Natl Acad Sci USA 100 Suppl 1:11917-11923; Prockop D J. (1997) Marrow stromal cells as stem cells for nonhematopoietic tissues. Science 276:71-74; Prockop D J, Kivirikko K I. (1995) Collagen: Molecular Biology, Diseases and Potentials for Therapy. Annual Review of Biochemistry 64:403-434; Prockop D J. (1985) Mutation in collagen genes. Consequences for rare and common diseases. Journal of Clinical Investigation 75:783-787; Qian H, Tryggvason K, Jacobsen S E, Ekblom M. (2006) Contribution of alpha6 integrins to hematopoietic stem and progenitor cell homing to bone marrow and collaboration with alpha4 integrins. Blood 107:3503-3510; Ren G, Zhang L, Zhao X, Xu G, Zhang Y, Roberts A I, Zhao R C, Shi Y. Mesenchymal stem cell-mediated immunosuppression occurs via concerted action of chemokines and nitric oxide. Cell Stem Cell. 2008 Feb. 7; 2(2):141-50; Ringden O, Uzunel M, Rasmusson I, Remberger M, Sundberg B, Lönnies H, Marschall H U, Dlugosz A, Szakos A, Hassan Z, Omazic B, Aschan J, Barkholt L, LeBlanc K. (2006) Mesenchymal stem cells for treatment of therapy-resistant graft-versus-host disease. Transplantation 81:1390-1397; Rosada C, Justesen J, Melsvik D, Ebbesen P, Kassem M. (2003) The human umbilical cord blood: a potential source for osteoblast progenitor cells. Calcif Tissue Int. February; 72(2):135-42; Schinköthe T, Bloch W, Schmidt A. (2008) In Vitro Secreting Profile of Human Mesenchymal Stem Cells. Stem Cells Dev. January 22; (Epub ahead of print]; Schrepfer S, Deuse T, Reichenspurner H, Fishbein M P, Robbins R C, Pelletier M P. (2007) Stem cell transplantation: the lung barrier. Transplant Proc 39:573-576; Schwab J M, Chiang N, Arita M, Serhan C N. Resolvin E1 and protectin D1 activate inflammation-resolution programmes. Nature. 2007 Jun. 14; 447(7146):869-

74; Segers V F, Lee R T. Stem-cell therapy for cardiac disease. Nature. 2008 Feb. 21; 451(7181):937-42; Serhan C N, Chiang N, Van Dyke T E. Resolving inflammation: dual anti-inflammatory and pro-resolution lipid mediators. Nat Rev Immunol. 2008 May; 8(5):349-61; Shoelson S E, Herrero L, Naaz A. Obesity, inflammation, and insulin resistance. Gastroenterology. 2007 May; 132(6):2169-80; Seo B M, Miura M, Sonoyama W, Coppe C, Stanyon R, Shi S. (2005) Recovery of stem cells from cryopreserved periodontal ligament. J Dent Res. October; 84(10):907-12; Simmons P J, Torok-Storb B. (1991) Identification of stromal cell precursors in human bone marrow by a novel monoclonal antibody, STRO-1. Blood 78:55-62; Smith J R, Pochampally R R, Perry A, Hsu S-C, Prockop D J. Isolation of a Highly Clonogenic and Multipotential Subfraction of Adult Stem Cells from Bone Marrow Stroma. Stem Cells 22: 823-831 (2004); Spees J L, Olson S D, Whitney M J, Prockop D J. (2006) Mitochondrial transfer between cells can rescue aerobic respiration. Proc Natl Acad Sci USA 103:1283-1288; Tansey M G, McCoy M K, Frank-Cannon T C. Neuroinflammatory mechanisms in Parkinson's disease: potential environmental triggers, pathways, and targets for early therapeutic intervention. Exp Neurol. 2007 November; 208(1):1-25; Theuma P, Fonseca V A. Inflammation, insulin resistance, and atherosclerosis. Metab Syndr Relat Disord. 2004 June; 2(2):105-13; Wakitani S, Saito T, Caplan A I. (1995) Myogenic cells derived from rat bone marrow mesenchymal stem cells exposed to 5-azacytidine. Muscle Nerve. December 18(12):1417-26; Wisniewski H G, Vilcek J. Cytokine-induced gene expression at the crossroads of innate immunity, inflammation and fertility: TSG-6 and PTX3/TSG-14. Cytokine Growth Factor Rev. 2004 April-June; 15(2-3):129-46; Woodbury D, Schwarz E J, Prockop D J, Black I B. (2000) Adult rat and human bone marrow stromal cells differentiate into neurons. J Neurosci Res. August 15; 61(4):364-70; Wu J, Sun Z, Sun H, Wu J, Weisel R D, Keating A, Li Z H, Feng Z P, Li R K. (2008) Intravenously administered bone marrow cells migrate to damaged brain tissue and improve neural function in ischemic rats. Cell Transplantation, 16(10):993-1005; Zacharek A, Chen J, Cui X, Li A, Li Y, Roberts C, Feng Y, Gao Q, Chopp M. (2007) Angiopoietin1/Tie2 and VEGF/Flk1 induced by MSC treatment amplifies angiogenesis and vascular stabilization after stroke. J Cereb Blood Flow Metab. October; 27(10):1684-91; Akiyama et al. (2002). Glia 39, 229-236; Baddoo et al. 2003) J. Cell Biochem. 89, 1235-1249; Bai, L., Lennon, D. P., Eaton, V., Maier, K., Caplan, A. I., Miller, S. D., and Miller, R. H. (2009). Human bone marrow-derived mesenchymal stem cells induce Th2-polarized immune response and promote endogenous repair in animal models of multiple sclerosis. Glia; Bardos, T., Kamath, R. V., Mikecz, K., and Glant, T. T. (2001). Anti-inflammatory and chondroprotective effect of TSG-6 (tumor necrosis factor-alpha-stimulated gene-6) in murine models of experimental arthritis. Am. J. Pathol. 159, 1711-1721; Bergsbaken, T., Fink, S. L., and Cookson, B. T. (2009). Pyroptosis: host cell death and inflammation. Nat. Rev. Microbiol. 7, 99-109; Block, G. J., Ohkouchi, S., Fung, F., Frenkel, J., Gregory, C., Pochampally, R., Dimattia, G., Sullivan, D. E., and Prockop, D. J. (2009). Multipotent stromal cells are activated to reduce apoptosis in part by upregulation and secretion of stanniocalcin-1. Stem Cells 27, 670-681; BURTON, K. (1956). A study of the conditions and mechanism of the diphenylamine reaction for the colorimetric estimation of deoxyribonucleic acid. Biochem. J. 62, 315-323; Caplan, A. I. (2007). Adult mesenchymal stem cells for tissue engineering versus regenerative medicine. J Cell Physiol 213, 341-347; Caplan, A. I. (2009). Why are MSCs therapeutic? New data: new insight. J. Pathol. 217, 318-324; Carvalho, R. F., Dariolli, R., Justulin Junior, L. A., Sugizaki, M. M., Politi, O. M., Cicogna, A. C., Felisbino, S. L., and Dal Pai-Silva, M. (2006). Heart failure alters matrix metalloproteinase gene expression and activity in rat skeletal muscle. Int. J. Exp. Pathol. 87, 437-443; Chapelle, J. P. (1998). (Troponin, a new myocardial infarction marker]. Rev. Med. Liege 53, 619-624; Chute, J. P. (2006). Stem cell homing. Curr. Opin. Hematol. 13, 399-406; Colter, D. C., Sekiya, I., and Prockop, D. J. (2001). Identification of a subpopulation of rapidly self-renewing and multipotential adult stem cells in colonies of human marrow stromal cells. Proc. Natl. Acad. Sci. U.S.A 98, 7841-7845; Dominici, M., Le Blanc, K., Mueller, I., Slaper-Cortenbach, I., Marini, F., Krause, D., Deans, R., Keating, A., Prockop, D., and Horwitz, E. (2006). Minimal criteria for defining multipotent mesenchymal stromal cells. The International Society for Cellular Therapy position statement. Cytotherapy. 8, 315-317; Dooner, M., Cerny, J., Colvin, G., Demers, D., Pimentel, J., Greer, D., Abedi, M., McAuliffe, C., and Quesenberry, P. (2004). Homing and conversion of murine hematopoietic stem cells to lung. Blood Cells Mol Dis 32, 47-51; Ezquer, F. E., Ezquer, M. E., Parrau, D. B., Carpio, D., Yanez, A. J., and Conget, P. A. (2008). Systemic administration of multipotent mesenchymal stromal cells reverts hyperglycemia and prevents nephropathy in type 1 diabetic mice. Biol. Blood Marrow Transplant. 14, 631-640; Fang, L., Gao, X. M., Moore, X. L., Kiriazis, H., Su, Y., Ming, Z., Lim, Y. L., Dart, A. M., and Du, X. J. (2007). Differences in inflammation, MMP activation and collagen damage account for gender difference in murine cardiac rupture following myocardial infarction. J. Mol. Cell Cardiol. 43, 535-544; Forteza, R., Casalino-Matsuda, S. M., Monzon, M. E., Fries, E., Rugg, M. S., Milner, C. M., and Day, A. J. (2007). TSG-6 potentiates the antitissue kallikrein activity of inter-alpha-inhibitor through bikunin release. Am. J. Respir. Cell Mol. Biol. 36, 20-31; Furlani, D., Ugurlucan, M., Ong, L., Bieback, K., Pittermann, E., Westien, I., Wang, W., Yerebakan, C., Li, W., Gaebel, R., Li, R. K., Vollmar, B., Ma, N., and Steinhoff, G. (2009). Is the intravascular administration of mesenchymal stem cells safe? Microvasc. Res; Gao, J., Dennis, J. E., Muzic, R. F., Lundberg, M., and Caplan, A. I. (2001). The dynamic in vivo distribution of bone marrow-derived mesenchymal stem cells after infusion. Cells Tissues. Organs 169, 12-20; Getting, S. J., Mahoney, D. J., Cao, T., Rugg, M. S., Fries, E., Milner, C. M., Perretti, M., and Day, A. J. (2002). The link module from human TSG-6 inhibits neutrophil migration in a hyaluronan- and inter-alpha-inhibitor-independent manner. J. Biol. Chem. 277, 51068-51076; Giordano, A., Galderisi, U., and Marino, I. R. (2007). From the laboratory bench to the patient's bedside: an update on clinical trials with mesenchymal stem cells. J Cell Physiol 211, 27-35; Gnecchi, M. and Melo, L. G. (2009). Bone marrow-derived mesenchymal stem cells: isolation, expansion, characterization, viral transduction, and production of conditioned medium. Methods Mol. Biol. 482, 281-294; Gnecchi, M., Zhang, Z., Ni, A., and Dzau, V. J. (2008). Paracrine mechanisms in adult stem cell signaling and therapy. Circ. Res. 103, 1204-1219; Gonzalez-Rey, E., Gonzalez, M. A., Rico, L., Buscher, D., and Delgado, M. (2009). Human adult stem cells derived from adipose tissue protect against experimental colitis and sepsis. Gut; Griffin, M. O., Jinno, M., Miles, L. A., and Villarreal, F. J. (2005). Reduction of myocardial infarct size by doxycycline: a role for plasmin inhibition. Mol. Cell Biochem. 270, 1-11; Halkos, M. E., Zhao, Z. Q., Kerendi, F., Wang, N. P., Jiang, R., Schmarkey, L. S., Martin, B. J., Quyyumi, A. A., Few, W. L., Kin, H., Guyton, R. A., and Vinten-Johansen, J. (2008). Intravenous infusion of mesenchymal stem cells enhances regional perfusion and improves ventricular function in a porcine model of myocardial infarction. Basic Res. Cardiol; Heng, B. C., Gribbon, P. M., Day, A. J., and Hardingham, T. E. (2008). Hyaluronan binding to link module of TSG-6 and to G1-domain of aggrecan is differently regulated by pH. J. Biol. Chem.; Heymans, S., Luttun, A., Nuyens, D., Theilmeier, G., Creemers, E., Moons, L., Dyspersin, G. D., Cleutjens, J. P., Shipley, M., Angellilo, A., Levi, M., Nube, O., Baker, A., Keshet, E., Lupu, F., Herbert, J. M., Smits, J. F., Shapiro, S. D., Baes, M., Borgers, M., Collen, D., Daemen, M. J., and Carmeliet, P. (1999) Inhibition of plasminogen activators or matrix metalloproteinases prevents cardiac rupture but impairs therapeutic angiogenesis and causes cardiac failure. Nat. Med. 5, 1135-1142; Horwitz, E. M., Prockop, D. J., Fitzpatrick, L. A., Koo, W. W., Gordon, P. L., Neel, M., Sussman, M., Orchard, P., Marx, J. C., Pyeritz, R. E., and Brenner, M. K. (1999). Transplantability and therapeutic effects of bone marrow-derived mesenchymal cells in children with osteogenesis imperfecta. Nat Med 5, 309-313; Hwang, N. S., Varghese, S., Lee, H. J., Zhang, Z., Ye, Z., Bae, J., Cheng, L., and Elisseeff, J. (2008). In vivo commitment and functional tissue regeneration using human embryonic stem cell-derived mesenchymal cells. Proc. Natl. Acad. Sci. U.S.A 105, 20641-20646; Iso, Y., Spees, J. L., Serrano, C., Bakondi, B., Pochampally, R., Song, Y. H., Sobel, B. E., Delafontaine, P., and Prockop, D. J. (2007). Multipotent human stromal cells improve cardiac function after myocardial infarction in mice without long-term engraftment. Biochem Biophys Res Commun 354, 700-706; Jolicoeur, E. M., Granger, C. B., Fakunding, J. L., Mockrin, S. C., Grant, S. M., Ellis, S. G., Weisel, R. D., and Goodell, M. A. (2007). Bringing cardiovascular cell-based therapy to clinical application: perspectives based on a National Heart, Lung, and Blood Institute Cell Therapy Working Group meeting. Am. Heart J. 153, 732-742; Khanna, C., Wan, X., Bose, S., Cassaday, R., Olomu, O., Mendoza, A., Yeung, C., Gorlick, R., Hewitt, S. M., and Helman, L. J. (2004). The membrane-cytoskeleton linker ezrin is necessary for osteosarcoma metastasis. Nat. Med. 10, 182-186; Koc, O. N., Day, J., Nieder, M., Gerson, S. L., Lazarus, H. M., and Krivit, W. (2002). Allogeneic mesenchymal stem cell infusion for treatment of metachromatic leukodystrophy (MLD) and Hurler syndrome (MPS-IH). Bone Marrow Transplant 30, 215-222; Koc, O. N., Peters, C., Aubourg, P., Raghavan, S., Dyhouse, S., DeGasperi, R., Kolodny, E. H., Yoseph, Y. B., Gerson, S. L., Lazarus, H. M., Caplan, A. I., Watkins, P. A., and Krivit, W. (1999). Bone marrow-derived mesenchymal stem cells remain host-derived despite successful hematopoietic engraftment after allogeneic transplantation in patients with lysosomal and peroxisomal storage diseases. Exp Hematol. 27, 1675-1681; Krause, U., Harter, C., Seckinger, A., Wolf, D., Reinhard, A., Bea, F., Dengler, T., Hardt, S., Ho, A., Katus, H. A., Kuecherer, H., and Hansen, A. (2007). Intravenous delivery of autologous mesenchymal stem cells limits infarct size and improves left ventricular function in the infarcted porcine heart. Stem Cells Dev. 16, 31-37; Le Blanc, K. and Ringden, O. (2006). Mesenchymal stem cells: properties and role in clinical bone marrow transplantation. Curr Opin Immunol. 18, 586-591; Le Blanc, K., Samuelsson, H., Gustafsson, B., Remberger, M., Sundberg, B., Arvidson, J., Ljungman, P., Lonnies, H., Nava, S., and Ringden, O. (2007). Transplantation of mesenchymal stem cells to enhance engraftment of hematopoietic stem cells. Leukemia 21, 1733-1738; Lee, R. H., Seo, M. J., Pulin, A. A., Gregory, C. A., Ylostalo, J., and Prockop, D. J. (2009). The CD34-like protein PODXL and alpha6-integrin (CD49f) identify early progenitor MSCs with increased clonogenicity and migration to infarcted heart in mice. Blood 113, 816-826; Lee, T. H., Wisniewski, H. G., and Vilcek, J. (1992). A novel secretory tumor necrosis factor-inducible protein (TSG-6) is a member of the family of hyaluronate binding proteins, closely related to the adhesion receptor CD44. J. Cell Biol. 116, 545-557; Lindsey, M., Wedin, K., Brown, M. D., Keller, C., Evans, A. J., Smolen, J., Burns, A. R., Rossen, R. D., Michael, L., and Entman, M. (2001). Matrix-dependent mechanism of neutrophil-mediated release and activation of matrix metalloproteinase 9 in myocardial ischemia/reperfusion. Circulation 103, 2181-2187; Lu, Z., Hu, X., Zhu, C., Wang, D., Zheng, X., and Liu, Q. (2009). Over-expression of CNTF in Mesenchymal Stem Cells reduces demyelination and induces clinical recovery in experimental autoimmune encephalomyelitis mice. J. Neuroimmunol. 206, 58-69; McBride, C., Gaupp, D., and Phinney, D. G. (2003). Quantifying levels of transplanted murine and human mesenchymal stem cells in vivo by real-time PCR. Cytotherapy. 5, 7-18; McCombe, P. A. and Read, S. J. (2008). Immune and inflammatory responses to stroke: good or bad? Int. J. Stroke 3, 254-265; Milner, C. M., Higman, V. A., and Day, A. J. (2006). TSG-6: a pluripotent inflammatory mediator? Biochem. Soc. Trans. 34, 446-450; Mindrescu, C., Dias, A. A., Olszewski, R. J., Klein, M. J., Reis, L. F., and Wisniewski, H. G. (2002). Reduced susceptibility to collagen-induced arthritis in DBA/1J mice expressing the TSG-6 transgene. Arthritis Rheum. 46, 2453-2464; Mindrescu, C., Thorbecke, G. J., Klein, M. J., Vilcek, J., and Wisniewski, H. G. (2000). Amelioration of collagen-induced arthritis in DBA/1J mice by recombinant TSG-6, a tumor necrosis factor/interleukin-1-inducible protein. Arthritis Rheum. 43, 2668-2677; Moshal, K. S., Rodriguez, W. E., Sen, U., and Tyagi, S. C. (2008). Targeted deletion of MMP-9 attenuates myocardial contractile dysfunction in heart failure. Physiol Res. 57, 379-384; Nishida, Y., Sugahara-Kobayashi, M., Takahashi, Y., Nagata, T., Ishikawa, K., and Asai, S. (2006). Screening for control genes in mouse hippocampus after transient forebrain ischemia using high-density oligonucleotide array. J. Pharmacol. Sci. 101, 52-57; Nomura, T., Honmou, O., Harada, K., Houkin, K., Hamada, H., and Kocsis, J. D. (2005). I.V. infusion of brain-derived neurotrophic factor gene-modified human mesenchymal stem cells protects against injury in a cerebral ischemia model in adult rat. Neuroscience 136, 161-169; Ohtaki, H., Ylostalo, J. H., Foraker, J. E., Robinson, A. P., Reger, R. L., Shioda, S., and Prockop, D. J. (2008). Stem/progenitor cells from bone marrow decrease neuronal death in global ischemia by modulation of inflammatory/immune responses. Proc. Natl. Acad. Sci. U.S.A 105, 14638-14643; Ovechkin, A. V., Tyagi, N., Rodriguez, W. E., Hayden, M. R., Moshal, K. S., and Tyagi, S. C. (2005). Role of matrix metalloproteinase-9 in endothelial apoptosis in chronic heart failure in mice. J. Appl. Physiol 99, 2398-2405; Owen, M. and Friedenstein, A. J. (1988). Stromal stem cells: marrow-derived osteogenic precursors. Ciba Found. Symp. 136, 42-60; Paolocci, N., Tavazzi, B., Biondi, R., Gluzband, Y. A., Amorini, A. M., Tocchetti, C. G., Hejazi, M., Caturegli, P. M., Kajstura, J., Lazzarino, G., and Kass, D. A. (2006). Metalloproteinase inhibitor counters high-energy phosphate depletion and AMP deaminase activity enhancing ventricular diastolic compliance in subacute heart failure. J. Pharmacol. Exp. Ther. 317, 506-513; Parr, A. M., Tator, C. H., and Keating, A. (2007). Bone marrow-derived mesenchymal stromal cells for the repair of central nervous system injury. Bone Marrow Transplant. 40, 609-619; Peister, A., Mellad, J. A., Larson, B. L., Hall, B. M., Gibson, L. F., and Prockop, D. J. (2004). Adult stem cells from bone marrow (MSCs) isolated from different strains of inbred mice vary in surface epitopes, rates of proliferation, and differentiation potential. Blood 103, 1662-1668; Pereira, R. F., O'Hara, M. D., Laptev, A. V., Halford, K. W., Pollard, M. D., Class, R., Simon, D., Livezey, K., and Prockop, D. J. (1998). Marrow stromal cells as a source of progenitor cells for nonhematopoietic tissues in transgenic mice with a phenotype of osteogenesis imperfecta. Proc Natl Acad Sci USA 95, 1142-1147; Pervaiz, S., Anderson, F. P., Lohmann, T. P., Lawson, C. J., Feng, Y. J., Waskiewicz, D., Contois, J. H., and Wu, A. H. (1997). Comparative analysis of cardiac troponin I and creatine kinase-MB as markers of acute myocardial infarction. Clin. Cardiol. 20, 269-271; Prockop, D. J. and Olson, S. D. (2007). Clinical trials with adult stem/progenitor cells for tissue repair: let's not overlook some essential precautions. Blood 109, 3147-3151; Qian, H., Tryggvason, K., Jacobsen, S. E., and Ekblom, M. (2006). Contribution of alpha6 integrins to hematopoietic stem and progenitor cell homing to bone marrow and collaboration with alpha4 integrins. Blood 107, 3503-3510; Sasportas, L. S., Kasmieh, R., Wakimoto, H., Hingtgen, S., van de Water, J. A., Mohapatra, G., Figueiredo, J. L., Martuza, R. L., Weissleder, R., and Shah, K. (2009). Assessment of therapeutic efficacy and fate of engineered human mesenchymal stem cells for cancer therapy. Proc. Natl. Acad. Sci. U.S.A; Schrepfer, S., Deuse, T., Reichenspurner, H., Fischbein, M. P., Robbins, R. C., and Pelletier, M. P. (2007). Stem cell transplantation: the lung barrier. Transplant Proc 39, 573-576; Schwab, J. M., Chiang, N., Arita, M., and Serhan, C. N. (2007). Resolvin E1 and protectin D1 activate inflammation-resolution programmes. Nature 447, 869-874; Shoelson, S. E., Lee, J., and Goldfine, A. B. (2006). Inflammation and insulin resistance. J. Clin. Invest 116, 1793-1801; Sung, J. H., Yang, H. M., Park, J. B., Choi, G. S., Joh, J. W., Kwon, C. H., Chun, J. M., Lee, S. K., and Kim, S. J. (2008). Isolation and characterization of mouse mesenchymal stem cells. Transplant. Proc. 40, 2649-2654; Szanto, S., Bardos, T., Gal, I., Glant, T. T., and Mikecz, K. (2004). Enhanced neutrophil extravasation and rapid progression of proteoglycan-induced arthritis in TSG-6-knockout mice. Arthritis Rheum. 50, 3012-3022; Takagawa, J., Zhang, Y., Wong, M. L., Sievers, R. E., Kapasi, N. K., Wang, Y., Yeghiazarians, Y., Lee, R. J., Grossman, W., and Springer, M. L. (2007). Myocardial infarct size measurement in the mouse chronic infarction model: comparison of area- and length-based approaches. J. Appl. Physiol 102, 2104-2111; Theuma, P. and Fonseca, V. A. (2004). Inflammation, insulin resistance, and atherosclerosis. Metab Syndr. Relat Disord. 2, 105-113; Tolar, J., Nauta, A. J., Osborn, M. J., Panoskaltsis, M. A., McElmurry, R. T., Bell, S., Xia, L., Zhou, N., Riddle, M., Schroeder, T. M., Westendorf, J. J., McIvor, R. S., Hogendoorn, P. C., Szuhai, K., Oseth, L., Hirsch, B., Yant, S. R., Kay, M. A., Peister, A., Prockop, D. J., Fibbe, W. E., and Blazar, B. R. (2007). Sarcoma derived from cultured mesenchymal stem cells. Stem Cells 25, 371-379; Uccelli, A., Moretta, L., and Pistoia, V. (2008). Mesenchymal stem cells in health and disease. Nat. Rev. Immunol. 8, 726-736; Wisniewski, H. G. and Vilcek, J. (2004). Cytokine-induced gene expression at the crossroads of innate immunity, inflammation and fertility: TSG-6 and PTX3/TSG-14. Cytokine Growth Factor Rev. 15, 129-146; Wolf, D., Reinhard, A., Krause, U., Seckinger, A., Katus, H. A., Kuecherer, H., and Hansen, A. (2007). Stem cell therapy improves myocardial perfusion and cardiac synchronicity: new application for echocardiography. J. Am. Soc. Echocardiogr. 20, 512-520; Wu, J., Sun, Z., Sun, H. S., Wu, J., Weisel, R. D., Keating, A., Li, Z. H., Feng, Z. P., and Li, R. K. (2008). Intravenously administered bone marrow cells migrate to damaged brain tissue and improve neural function in ischemic rats. Cell Transplant. 16, 993-1005; Ylostalo, J., Bazhanov, N., and Prockop, D. J. (2008). Reversible commitment to differentiation by human multipotent stromal cells in single-cell-derived colonies. Exp. Hematol. 36, 1390-1402.

All references, patents and patent publications cited in this specification are herein incorporated by reference as though each reference was specifically and individually indicated to be incorporated by reference. The citation of any reference is for its disclosure prior to the filing date and should not be construed as an admission that the present invention is not entitled to antedate such reference by virtue of prior invention.

It is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

It will be further understood that each of the elements described above, or two or more together may also find a useful application in other types of methods differing from the type described above. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention set forth in the appended claims. The foregoing embodiments are presented by way of example only.

Each and every publication and patent mentioned in the above specification is herein incorporated by reference in its entirety for all purposes.

We claim:

1. A method of reducing the size of a myocardial infarction in a mammalian subject, comprising:
   (a) administering to said mammalian subject, immediately after the occurrence of said myocardial infarction, tumor necrosis factor-alpha stimulating gene 6 (TSG-6) protein, wherein said TSG-6 protein is administered in an amount of about 100 µg; and
   (b) administering to said mammalian subject, at 24 hours after the occurrence of said myocardial infarction, said TSG-6 protein in an amount of about 100 µg.

2. The method of claim 1 wherein said mammalian subject is a human.

3. The method of claim 1 wherein said TSG-6 protein is administered intravenously.

* * * * *